United States Patent
Morrow et al.

(10) Patent No.: US 11,344,635 B2
(45) Date of Patent: May 31, 2022

(54) COMPOUNDS FOR USE AS IRON (III) MRI CONTRAST AGENTS CONTAINING ANIONIC PENDENTS AND ANCILLARY GROUPS

(71) Applicant: The Research Foundation for The State University of New York, Buffalo, NY (US)

(72) Inventors: Janet R. Morrow, Williamsville, NY (US); Zuiru Lin, Williamsville, NY (US); Didar Asik, Tonawanda, NY (US); Eric M. Snyder, Tonawanda, NY (US); Elizabeth A. Kras, Amherst, NY (US)

(73) Assignee: The Research Foundation for the State University of New York, Amherst, NY (US)

( * ) Notice: Subject to any disclaimer, the term of this patent is extended or adjusted under 35 U.S.C. 154(b) by 0 days.

(21) Appl. No.: 16/973,349

(22) PCT Filed: Nov. 18, 2019

(86) PCT No.: PCT/US2019/062077
§ 371 (c)(1),
(2) Date: Dec. 8, 2020

(87) PCT Pub. No.: WO2020/102820
PCT Pub. Date: May 22, 2020

(65) Prior Publication Data
US 2021/0260222 A1 Aug. 26, 2021

Related U.S. Application Data

(60) Provisional application No. 62/768,823, filed on Nov. 16, 2018.

(51) Int. Cl.
*A61K 49/10* (2006.01)
*C07F 9/6515* (2006.01)
*C07F 15/02* (2006.01)

(52) U.S. Cl.
CPC .......... *A61K 49/106* (2013.01); *C07F 9/6515* (2013.01); *C07F 15/025* (2013.01)

(58) Field of Classification Search
CPC .. A61K 49/00; A61K 49/106; A61K 2121/00; A61K 2123/00; A61K 49/10; C07F 9/6515; C07F 15/025; C07F 15/02
USPC ........ 424/1.11, 1.65, 9.1, 9.2, 9.6, 1.53, 9.3, 424/9.36, 9.363; 534/7, 10–16
See application file for complete search history.

(56) References Cited

U.S. PATENT DOCUMENTS

| 5,236,695 A | 8/1993 | Winchell et al. |
| 5,409,689 A | 4/1995 | Winchell et al. |
| 6,264,966 B1 | 7/2001 | Winchell et al. |
| 9,233,971 B2 | 1/2016 | Cui et al. |
| 10,960,088 B2 * | 3/2021 | Morrow ............... A61K 49/106 |
| 2005/0112066 A1 | 5/2005 | Winchell |
| 2016/0228581 A1 | 8/2016 | Morrow et al. |

FOREIGN PATENT DOCUMENTS

| CN | 104119402 B | 8/2016 |
| WO | 2013/060793 A1 | 5/2013 |
| WO | 2018/213853 A1 | 11/2018 |

OTHER PUBLICATIONS

Tsitovich et al, Inorganic Chemistry, Jun. 25, 2018, vol. 57, pp. 8364-8374. (Year: 2018).*
Cardona, University of New Hampshire, Thesis: Synthesis of 1, 4, 7-triazacyclononane pendant-armed chelators and their metal complexes, 125 pages. (Year: 2010).*
PubChem-CID-10641504, (S)-1-(1,4,7-Triazacyclononane-1-yl)propane-2-ol, Oct. 25, 2006, 8 pages.
Tsitovitch, P.B., et al., Low-Spin FE(III) Macrocyclic Compleses of Imidazole-Appended 1,4,7-Triazacyclononane as Paramagnetic Probes, Inorgic Chemistry, Jul. 2018, vol. 57, No. 14, pp. 8364-8374.
Simecek, J., et al., Tailored Gallium(III) chelator NOPO: Synthesis, Characterization, Bioconjugation, and Application in Preclinical Ga-68- PET Imaging, Molecular Phamraceutics, Dec. 10, 2013, vol. 11, pp. 3893-3903.
Simecek, J., et al., A Monoreactive Bifunctional Triazacyclononane Phosphinate Chelator with High Selectivity for Gallium-68, Chem Med Chem, 2012, vol. 7, pp. 1375-1378.
Cole, E., et al., 1,4,7-Triazacyclononane-1,4,7-triyltrimethylenetris-(phenylphosphinate) enforces Octahedral Geometry: Crystal and Solution Structures of its Metal Complexes and Comparative Biodistribution Studies of Radiolabelled Indium and Gallium Complexes, J. Chem. Soc. Dalotn Trans., 1994, pp. 1619-1629.
Bazakas, K., et al., Synthesis and Complexing Properties of Polyazamacrocycles with Pendant N-Methylenephosphinic Acid, J. Chem, Soc. Dalton Trans. 1995, vol. 7, pp. 1133-1138.
Ren, M., et al., A layered erbium phosphonate in pseudo-D5h symmetry exhibiting field-tunable magnetic relaxation and optical correlation, Chem Commun., 2014, vol. 50, pp. 7621-7624.
Ren, M., et al., Solvent Responsive Magnetic Dynamics of a Dinuclear Dysprosium Single-Molecule Magnet, Chemistry A European Journal, 2013, vol. 19, No. 29, pp. 9619-9628.
Ren, M., et al., A cryogenic luminescent ratiometric thermometer based on a lanthanide phosphonate dimer, J. Mater. Chem. C, 2015, vol. 3, pp. 8480-8484.
Broan, C.J., et al., Synthesis of New Macrocyclic Aminophosphinic Acid Complexing Agents and Their C- and P-Functionalised Derivatives for Protein Linkage, Synthesis, 1992, vol. 1-2, pp. 63-68.

* cited by examiner

*Primary Examiner* — D. L. Jones
(74) *Attorney, Agent, or Firm* — Hodgson Russ LLP

(57) ABSTRACT

Macrocyclic complexes and macrocyclic compounds. The macrocyclic complexes or macrocyclic compounds have a TACN moiety with one or more amine group(s) or a O- or S-substituted TACN moiety. The macrocyclic complexes have a high-spin Fe(III) atom coordinated to the TACN moiety. The macrocyclic complexes can be used in imaging methods.

8 Claims, 18 Drawing Sheets i methanol, heat to 60 °C, 4 h
ii propargyl alcohol, Cu(SO₄), ascorbate, 60 °C, 8-12 hours
iii 3 eq. PBr₃

COMPOUNDS FOR USE AS IRON (III) MRI CONTRAST AGENTS CONTAINING ANIONIC PENDENTS AND ANCILLARY GROUPS

CROSS-REFERENCE TO RELATED APPLICATIONS

This application claims priority to U.S. provisional patent application No. 62/768,823, filed Nov. 16, 2018, the disclosure of which is incorporated herein by reference.

STATEMENT REGARDING FEDERALLY SPONSORED RESEARCH

This invention was made with government support under Contract No. 1710224 awarded by the National Science Foundation and Contract No. EB025369 awarded by the National Institutes of Health. The government has certain rights in the invention.

FIELD OF THE DISCLOSURE

This disclosure relates generally to macrocyclic compounds. When complexed with iron(III), these compounds can be used as MRI contrast agents.

SUMMARY OF THE DISCLOSURE

It is an object of the present disclosure to provide macrocyclic compounds that can be complexed with Fe(III). It is also an object of the present disclosure to provide compositions and methods of making and using the compounds and complexes.

Disclosed are Fe(III) coordination complexes for use as $T_1$ MRI contrast agents. The disclosed Fe(III) $T_1$ MRI contrast agents contain macrocyclic ligands. The Fe(III) complexes may also be used as $T_2$ MRI contrast agents.

The present disclosure provides a macrocyclic compound or macrocycle having i) a macrocyclic core comprising at least two heteroatoms as ligand donors and ii) at least one pendent donor, which may be referred to as an anionic pendent, as a substituent of the macrocyclic core. The macrocyclic core has a ring structure comprising carbon atoms and at least one heteroatom (e.g. N atom, O atom, or S atom). The macrocyclic core may be a TACN moiety. The macrocyclic core may be a TACN moiety were one or more of the N atom(s) are substituted with an O atom or an S atom.

For example, the pendent donor can be an oxygen-containing group (e.g., alcohol, oxide (e.g., alkoxide or phenoxide), sulfonate, phosphinate, phosphonate and the like). Some pendent donors, such as, for example, alcohol, phosphinic acid, phosphonic acid or sulfonic acid may deprotonate when complexed with Fe(III) or at certain pHs.

The macrocyclic compound may comprise one or more ancillary pendent groups. The ancillary pendent group(s) may be one or more coordinating ancillary pendent groups and/or one or more non-coordinating ancillary pendent groups.

In an embodiment, the compounds of the present disclosure have more than one macrocyclic core tethered together via an aromatic (e.g., aryl) group, macrocycle, polymer, dendrimer, protein, or peptide.

For use in methods of the disclosure, the compounds or complexes described herein can be administered as pharmaceutical preparations. Thus, they can be provided in a variety of compositions, and can be combined with one or more pharmaceutically acceptable carriers.

In an aspect, the present disclosure provides imaging methods using the macrocyclic compounds described herein. The imaging methods use magnetic resonance imaging methods. Examples of such methods include, but are not limited to, magnetic resonance imaging (MRI). Specifically, macrocyclic compounds of the present disclosure, when complexed to Fe(III), can be used as $T_1$ MRI contrast agents. The imaging methods of the present disclosure can be used to image a cell, tissue, organ, vasculature, or a part thereof. The cell, tissue, organ, vasculature can be a part of an individual.

BACKGROUND OF THE DISCLOSURE

Contrast agents containing Fe(III), as trivalent iron, would provide an alternative to Gd(III) contrast agents. To date, nearly all clinically-used contrast agents contain gadolinium (Gd as trivalent Gd(III)) despite the fact that a substantial proportion of patients in the US population (ca 10%) are considered at risk for being given Gd(III) contrast agents. There are new concerns that Gd(III) based MRI contrast agents are leading to the deposition of Gd(III) into brain, bone and skin of all patients. Alternatives to Gd(III) contrast agents that involve biologically relevant transition metal ions such as high spin Fe(III) complexes would be valuable. Alternatives to Gd(III) contrast agents that involve biologically relevant transition metal ions include high spin Mn(II) and high spin Fe(III) complexes. Potential advantages of using Fe(III) include the extensive mechanisms in the human body for recycling and storage of iron, as the most abundant of the transition metal ions. Also, Fe(III) complexes are less prone towards dissociation than Mn(II). Notably, the redox potentials of both Mn(II) and Fe(III) complexes can be tuned to prevent reactive oxygen species (ROS) production. For example, certain ligands form redox-inactive Fe(III) complexes that do not produce hydroxyl radicals even under harsh conditions. The iron-based MRI contrast agents described herein (as trivalent Fe(III)) produce contrast by the same paramagnetic mechanism as Gd(III) agents and are in small molecule form as coordination complexes, i.e., they are NOT nanoparticles.

Most Fe(III) MRI contrast agents that have been reported to date contain simple linear chelates including those with an ethylene diamine backbone with a combination of phenol and carboxylate pendents such as EHBG (NN'-ethylenebis [(2-hydroxybenzyl)glycine). Another type contains polyaminocarboxylate ligands, such as Fe(III) complexes of EDTA. A third type contains the bacterial siderophore, desferrioxamine (DFO). All of these complexes have drawbacks including lack of exchangeable water ligands, reduction potentials that are amenable for ROS generation and/or difficulty of synthetic modification. Also, the aqueous solution chemistry of Fe(III) complexes is dominated by the formation of insoluble complexes with hydroxides and bridging oxide ligands. Improvements are needed to obtain Fe(III) complexes that are not effective catalysts for the production of ROS by tuning redox potential to stabilize Fe(III), and are desirable $T_1$ relaxivity agents. Further considerations are the overall charge of the complex. Anionic groups that bind to the Fe(III) as pendents or are attached more remotely as ancillary groups are an important to modulate the pharmacokinetics of the contrast agent and its elimination from the body.

Based on at least the foregoing, there is an ongoing and unmet need in the art for Fe(III) MRI contrast agents with improved properties.

DETAILED DESCRIPTION OF THE DISCLOSURE

Figure 1:
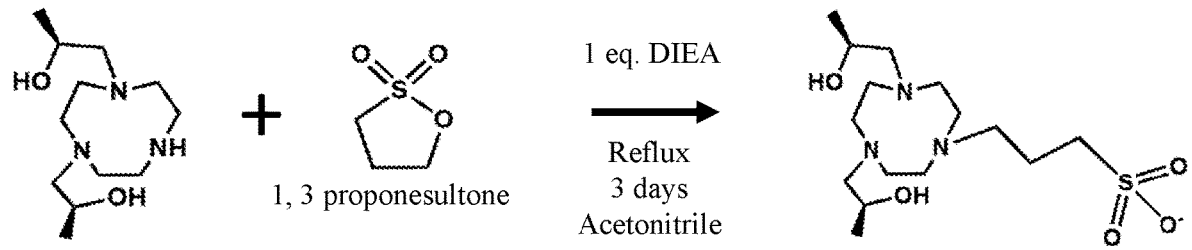
FIG. 1 shows a scheme for the synthesis of TASO ligand.

It is an object of the present disclosure to provide macrocyclic compounds that can be complexed with Fe(III). It is also an object of the present disclosure to provide compositions and methods of making and using the compounds and complexes.

High spin Fe(III) complexes with macrocyclic ligands may be developed as $T_1$ MRI contrast agents. Notably, high spin Fe(III) has favorable paramagnetic properties that shorten $T_1$ relaxation times of the protons of water for MRI contrast through both innersphere and outersphere interactions with water molecules.

Disclosed are Fe(III) coordination complexes for use as $T_1$ MRI contrast agents. The disclosed Fe(III) $T_1$ MRI contrast agents contain macrocyclic ligands. Without intending to be bound by any particular theory, it is considered that the macrocyclic ligands control of spin and oxidation state and anionic groups control of overall charge of the complex. The Fe(III) complexes may also be used as $T_2$ MRI contrast agents.

When complexed with Fe(III), the macrocyclic compounds of the present disclosure (as ligands) have advantages towards accomplishing control over spin and oxidation state and also interactions with innersphere and outersphere water. The cavities of these macrocyclic ligands are suitable for stabilization of Fe(III) in high spin form. Also, control of aqueous solution chemistry can be accomplished with these macrocyclic compounds. The macrocyclic complexes described here nearly encapsulate the Fe(III), but in some cases, have a coordination site for water ligands that enhances their efficacy as $T_1$ MRI contrast agents. In some cases, the innersphere water ligand may produce $T_1$ relaxivity of bulk water protons through second-sphere interactions. The iron-based MRI contrast agents described herein (macrocycles complexed with high spin, trivalent Fe(III)) produce contrast by the same paramagnetic mechanism as Gd(III) agents and are in small molecule form as coordination complexes, i.e., they are not nanoparticles.

As used herein, unless otherwise indicated, the term "group" or "moiety" refers to a chemical entity that is monovalent (i.e., has one terminus that can be covalently bonded to other chemical species), divalent, or polyvalent (i.e., has two or more termini that can be covalently bonded to other chemical species). Examples of groups include, but are not limited to:

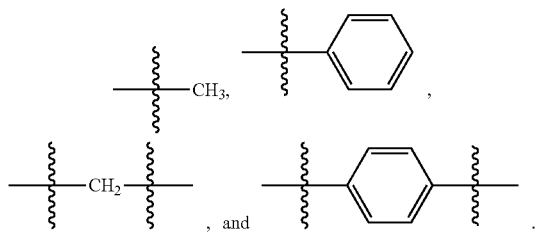

As used herein, unless otherwise indicated, the term "alkyl" or "alkyl group" refers to branched or unbranched saturated hydrocarbon groups. Examples of alkyl groups include, but are not limited to, methyl groups, ethyl groups, n- and isopropyl groups, n-, iso-, sec-, and tert-butyl groups, and the like. For example, the alkyl group can be a $C_1$ to $C_{12}$, including all integer numbers of carbons and ranges of numbers of carbons therebetween. The alkyl group can be unsubstituted or substituted with one or more substituents. Examples of substituents include, but are not limited to, various substituents such as, for example, halogens (—F, —Cl, —Br, and —I), aliphatic groups (e.g., alkyl groups, alkenyl groups, and alkynyl groups), aryl groups, alkoxide groups, thioalkoxide groups, carboxylate groups, carboxylic acids, ether groups, and the like, and combinations thereof.

As used herein, unless otherwise indicated, the term "aryl" or "aryl group" refers to $C_5$ to $C_{12}$, including all integer numbers of carbons and ranges of numbers of carbons therebetween, aromatic or partially aromatic carbocyclic groups. An aryl group can also be referred to as an aromatic group. The aryl groups can comprise polyaryl groups such as, for example, fused ring or biaryl groups. The aryl group can be unsubstituted or substituted with one or more substituent. Examples of substituents include, but are not limited to, substituents such as, for example, halogens (—F, —Cl, —Br, and —I), aliphatic groups (e.g., alkenes, alkynes, and the like), aryl groups, alkoxides, thioalkoxides, carboxylates, carboxylic acids, ether groups, and the like, and combinations thereof. Examples of aryl groups include, but are not limited to, phenyl groups, biaryl groups (e.g., biphenyl groups and the like), and fused ring groups (e.g., naphthyl groups and the like).

As used herein, unless otherwise indicated, the term "aralkyl" refers to any group derived from an alkyl group by replacing one or more hydrogen atoms on the alkyl group with one or more aryl groups.

As used herein, unless otherwise indicated, the term "heterocyclic group" refers to $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$) cyclic groups containing one or more heteroatoms (e.g., N, O, S, or the like) as part of the ring structure. The heterocyclic groups may be substituted or unsubstituted and/or have additional degrees of unsaturation. The heterocyclic group can be a fused ring (e.g., pyrrolizidinyl groups and the like). Non-limiting examples of heterocyclic groups include furanyl groups, oxazolyl groups, isothiazolyl groups, thiazolyl groups, tetrahydropyranyl groups, piperazinyl groups, dioxanyl groups, pyrrolidinyl groups, tetrahydrothiophenyl groups, tetrahydrofuranyl groups, quinuclidinyl groups, azaadamantanyl groups, decahydroquinolinyl groups, and the like.

The present disclosure provides a macrocyclic compound or macrocycle having i) a macrocyclic core comprising at least two heteroatoms as ligand donors and ii) at least one pendent donor as a substituent of the macrocyclic core. The macrocyclic core has a ring structure comprising carbon atoms and at least one heteroatom (e.g. N atom, O atom, or S atom). As used herein, "macrocycle donor" refers to a heteroatom with an available lone pair of electrons to donate to the Fe(III) center when present in the macrocyclic core of the compound. For example, the macrocycle donor can be a nitrogen atom (e.g. a tertiary amine, a secondary amine), or an oxygen atom (e.g., an ether). As used herein, "pendent donor", which includes anionic pendents and ancillary pendents, refers to a heteroatom with an available lone pair of electrons to donate to the Fe(III) center when present in a substituent on the macrocyclic core of the compound. For example, the pendent donor can be an oxygen-containing group (e.g., alcohol, oxide (e.g., alkoxide or phenoxide), sulfonate, phosphinate, phosphonate and the like). Some pendent donors, such as, for example, alcohol, phosphinic acid, phosphonic acid or sulfonic acid may deprotonate when complexed with Fe(III) or at certain pHs. Such protonated and deprotonated forms are within the scope of the present disclosure. In some embodiments, the macrocyclic compounds are complexed to Fe(III) to provide a stabilized trivalent state ($E_o$<0 mV versus NHE). In certain embodiments of Schemes I and II, $R_1$ may be an ancillary group that does not bond to the Fe(III). Anionic groups may be added to ancillary groups that do not bond to the Fe(III), including sulfonate, phosphinate, phosphate, phosphonate or carboxylate groups.

The macrocyclic core may be a TACN moiety. The macrocyclic core may be a TACN moiety were one or more of the N atom(s) are substituted with an O atom or an S atom.

In certain embodiments, the macrocycles have the following structure (Scheme 1):

SCHEME I

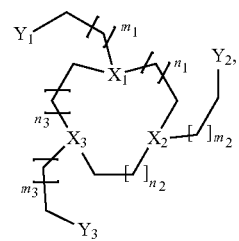

A

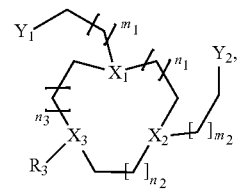

B

C

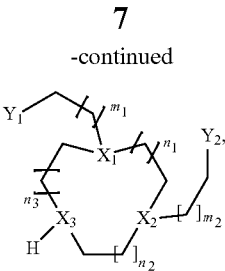

D

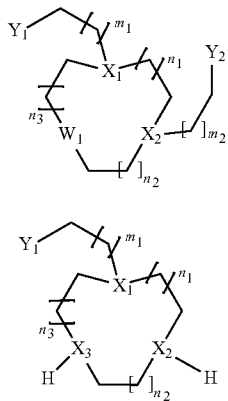

E where $X_1$, $X_2$, $X_3$, are N; $W_1$ is O or S; $Y_1$, $Y_2$, $Y_3$ are each independently i) pendent donors comprising O, where O has at least one lone pair of electrons but preferably two or three lone pairs (e.g., ketone, alcohol, alkoxide, phenol or phenoxide, sulfonic acid, phosphinic acid or phosphonic acid or a deprotonated form of the foregoing, such as, for example, an oxide, including an alkoxide or a phenoxide); or ii) pendent donors comprising N, where N has a least one lone pair of electrons such as, for example, triazole; $m_1$, $m_2$ and $m_3$ are each independently 1, 2 or 3; $n_1$, $n_2$, and $n_3$ are each independently 1 or 2 or 3; and $R_1$ is a substituted or unsubstituted aryl, a substituted or unsubstituted heterocyclic group or substituted or unsubstituted alkyl, and where the alkyl segment of the alkyl-Y chain (alkyl-$Y_1$, alkyl-$Y_2$, and/or alkyl-$Y_3$) may each independently be substituted or unsubstituted. In another embodiment, any or all of alkyl-$Y_1$, alkyl-$Y_2$, alkyl-$Y_3$, may each independently be any of Structures 1-9 as defined in Scheme III.

In certain embodiments, $R_1$ is not substituted by a pendent donor.

In some embodiments, the macrocycle may have the structure (Scheme II):

SCHEME II (I)

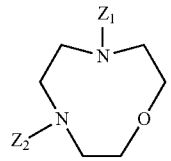

(II)

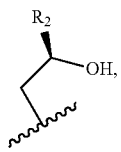

(III)

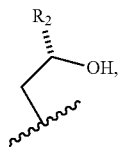

where $R_1$ is a substituted or unsubstituted aryl, substituted or unsubstituted heteroaryl or a substituted or unsubstituted alkyl and where when the macrocycle has Structure I, $Z_1$ is H or one of the pendent groups in Scheme III and $Z_2$ and $Z_3$ each independently are one of the pendent groups in Scheme III; when the macrocycle has Structure II or III, $Z_1$ and $Z_2$ each independently are one of the pendent groups in Scheme III; and where for all Structures I-III, each of $Z_1$, $Z_2$, $Z_3$, as applicable, are selected independently of each other. This paragraph is hereinafter referred to as "Scheme II."

In some embodiments, when the macrocycles of Scheme II are complexed with Fe(III), $R_1$ does not coordinate to the Fe(III).

In an embodiment, the macrocycles defined herein or according to Schemes I or II have at least one pendent donor on the macrocyclic core. For example, said pendent donor can have the following structure (Scheme III).

Scheme III

1A

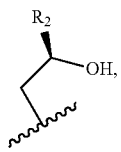

1B

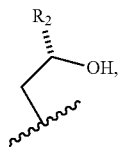

2

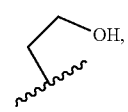

3

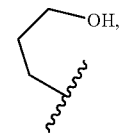

4

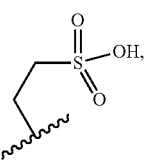

5

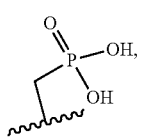

-continued

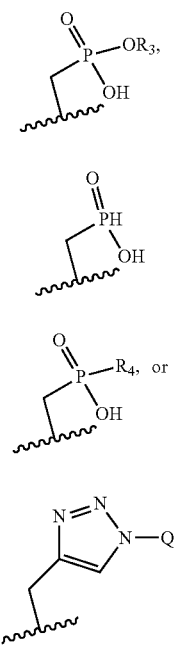

where $R_2$ is a substituted or unsubstituted alkyl group, a substituted or unsubstituted aromatic group, which may be an aryl group, or a substituted ether; $R_3$ is a substituted or unsubstituted alkyl or a substituted or unsubstituted aryl group and $R_4$ is a substituted alkyl (e.g., substituted with a hydroxyl or a carboxylate group, or the like) or unsubstituted alkyl or a substituted or unsubstituted aryl group. Some pendent donors, such as, for example, alcohol, phosphinic acid, phosphonic acid or sulfonic acid may deprotonate when complexed with Fe(III) or at certain pH values. Such protonated and deprotonated forms are within the scope of the present disclosure. For example, the pendent donor may be an alkoxide, phosphinate, phosphonate or sulfonate as shown in Scheme IV.

SCHEME IV - ionized groups

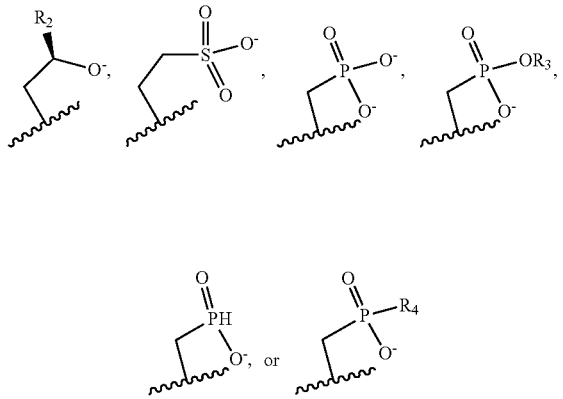

In certain embodiments, the $R_1$ group (which may be coordinating ancillary groups or non-coordinating ancillary groups) of said macrocycles in Schemes I and II may be a structure according to Scheme V,

SCHEME V

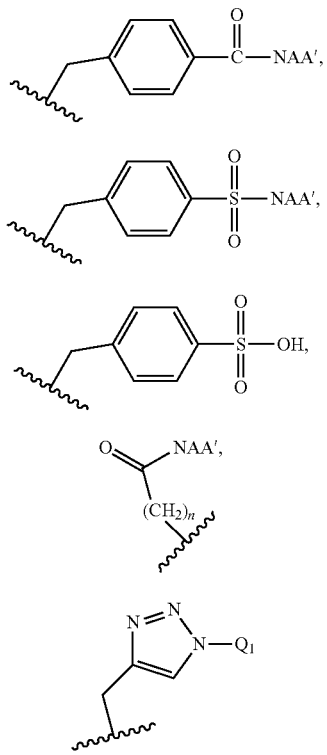

where A and A' are each independently a substituted or unsubstituted $C_1$ to $C_{12}$ alkyl group of linear or branched structure or a proton and $Q_1$ is aryl substituted with an anionic group (such as, for example, a carboxylate, sulfonate, phosphonate, phosphate ester or phosphinate), an alkyl group substituted with an anionic group (such as, for example, a carboxylate, sulfonate, phosphonate, phosphate ester or phosphinate) or an aralkyl group substituted with an anionic group (such as, for example, a carboxylate, sulfonate, phosphonate, phosphate ester or phosphinate); where at least one of A or A' is an alkyl group substituted with an anionic group (e.g., an amino acid, especially glycine, serine or aspartic acid). Amino phosphinic acids and phosphate esters are preferred.

In one embodiment, $Q_1$ is aralkyl and the alkyl portion of said aralkyl group is methyl ($C_1$).

In some embodiments, the pendent donors of Scheme V (e.g., $R_1$ in Schemes I and II) do not coordinate the Fe(III) center. Without intending to be bound by any particular theory, it is considered these pendents serve to modulate the charge on the complex and to promote binding to serum albumin. In other embodiments, the pendent donors of Scheme V (e.g., $R_1$ in Schemes I and II) coordinate the Fe(III) center.

As previously noted, some pendent donors, such as, for example, alcohol, sulfonic acid, phosphinic acid, or phosphonic acid may be deprotonated when complexed with Fe(III) or in solution as the pH is made more basic. Their corresponding alkoxides, sulfonates, phosphinates, phosphonates are within the scope of the present disclosure.

Certain pendents may have more than one N or O donor atom (e.g., triazole or phosphonate or phosphinate) although generally only one is coordinated to metal ion.

When more than one pendent donor is present, they may be the same or different. In various examples, when more than one pendent donor is present, the individual pendents may be the same or different.

The macrocyclic compound may comprise one or more ancillary pendent groups. The ancillary pendent group(s) may be one or more coordinating ancillary pendent groups and/or one or more non-coordinating ancillary pendent groups.

A non-coordinating ancillary pendent group does not have a heteroatom that can bind to the Fe(III) metal ion to form a five-membered or six-membered chelate. Non-limiting examples of non-coordinating ancillary pendent groups include benzyl groups, phenyl groups, and other aromatic (e.g., aryl) groups that have one or more methylene group attached to aromatic group or no methylene groups), alkyl groups (both branched and linear groups), and the like. Other non-limiting examples of non-coordinating ancillary pendent groups include biphenyl, napthyl, anthracenyl, pyridyl, quinolyl, methyl, ethyl, isopropyl, n-propyl, ethyl methoxyether, PEG derivatives (polyethylene glycol) and the like.

Non-limiting examples of coordinating ancillary pendent groups (e.g., a third pendent group when two are hydroxyl propyl, phosphinate or phosphonate) include oxygen or nitrogen donors that form five or six-membered chelates such as, for example, amides, carboxylates, alcohols or phenols, or derivatives of triazole, imidazole, pyrazole, picolyl, pyridine, alkylamines, aminopyridine, aminophenol, aniline, and the like. Some of these groups may deprotonate when bound to Fe(III).

A macrocyclic complex comprising one or more non-coordinating ancillary pendent groups may have one or more open coordination site(s) (have open coordination), which may be an innersphere water molecule(s), hydroxide(s), or a combination thereof. A macrocyclic complex comprising one or more coordinating ancillary pendent group may not have an open coordination site (have closed coordination). In the case of closed coordination or open coordination, the macrocyclic complex may have second sphere water molecule(s).

In various examples, the macrocyclic core can have 2 or 3 nitrogen atoms, 0 or 1 oxygen atoms, and/or 0 or 1 sulfur atoms. For example, the macrocyclic core can have 6, 7, 8, or 9 carbons. For example, the macrocyclic core may have 9 to 12 atoms, including all ranges and integers there between, where at least one of the atoms in the macrocyclic core is a heteroatom, such as, for example, N. In another embodiment, at least two of the atoms in the macrocyclic core are heteroatoms, such as, for example, N. In various examples, there are 2, or 3 carbon atoms separating the heteroatoms in the macrocyclic core. The one or more carbons in the macrocyclic core can be unsubstituted (e.g., $-CH_2-$) or substituted (e.g., $-CHR-$ or $-CHRR-$), provided that at least one carbon in the macrocyclic core is substituted with a pendent donor. For example, they can be substituted with the substituents disclosed herein. In another embodiment, the macrocyclic core comprises at least two heteroatoms, each of which is independently N or O, which are separated from each other by at least two carbon atoms.

In some embodiments, the pendent groups are covalently attached to a macrocyclic core (e.g. at a nitrogen): especially for TACN (I).

Non-limiting examples of the macrocyclic compounds are depicted in Schemes VI and VII below:

SCHEME VI

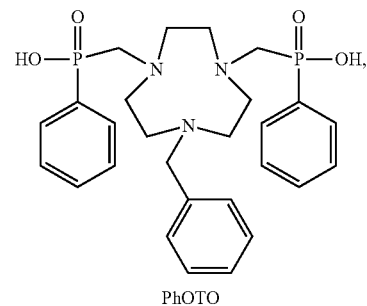

PhOTO

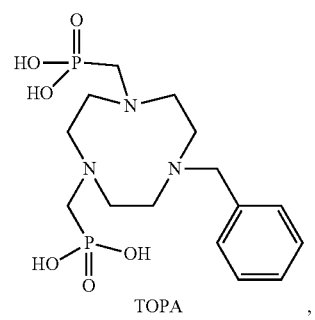

TOPA

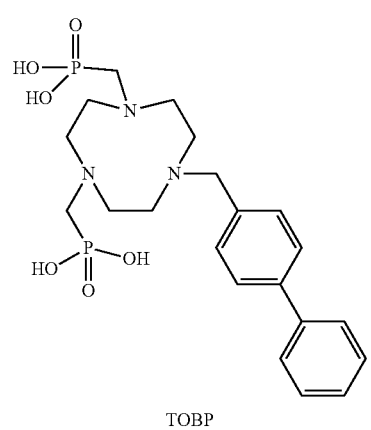

TOBP

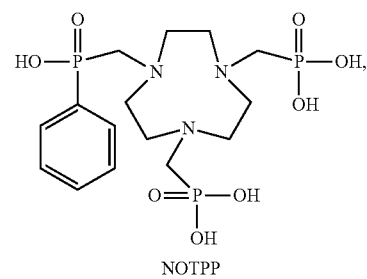

NOTPP

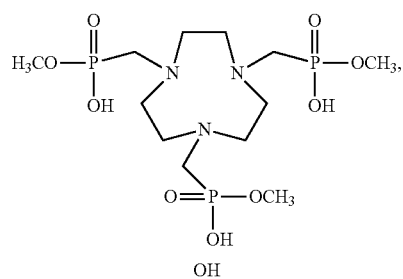

-continued
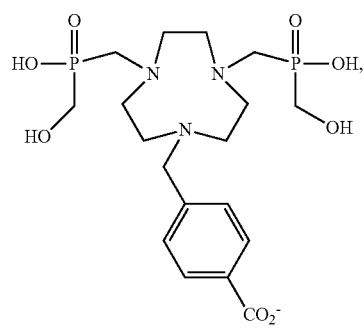
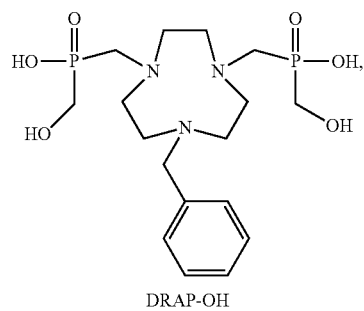
DRAP-OH
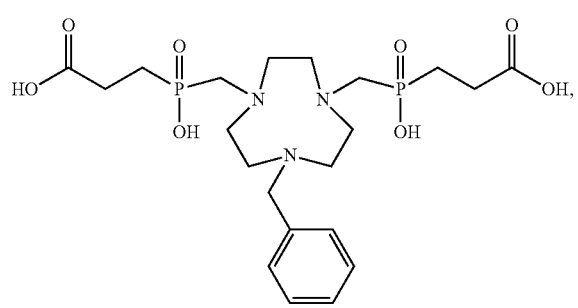
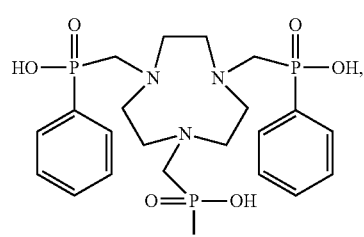
TRAP-POP
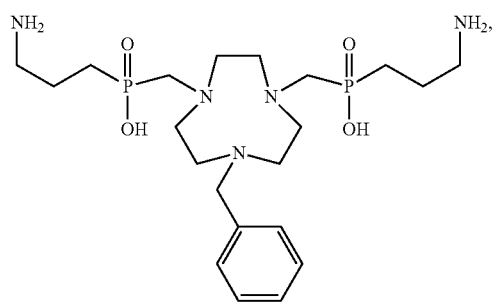
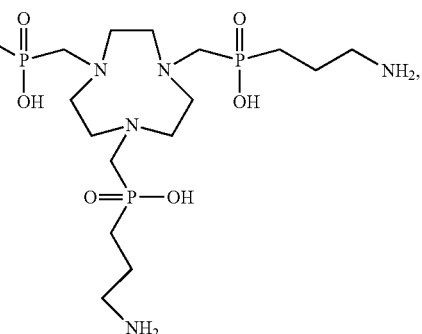
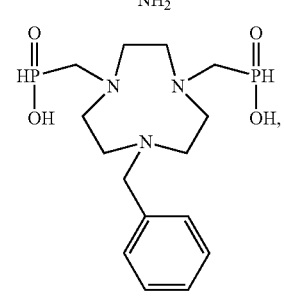
DRAP-H
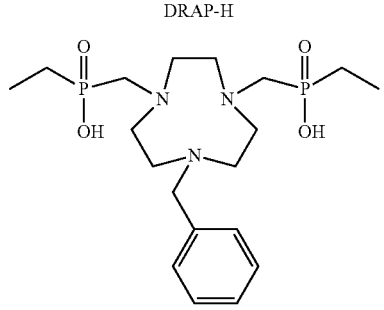
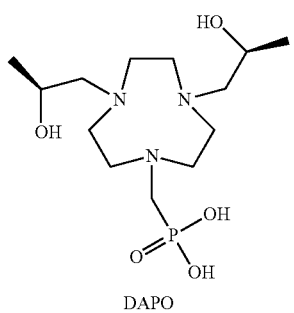 [SMILES: C[C@H](O)CN1CCN(C[C@H](C)O)CCN(CP(=O)(O)O)CC1 ; "DAPO"]
DAPO
SCHEME VII
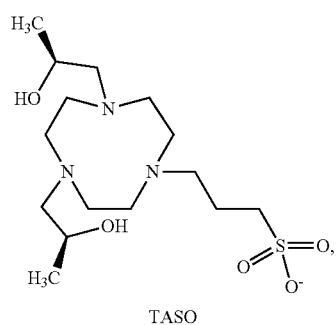
TASO

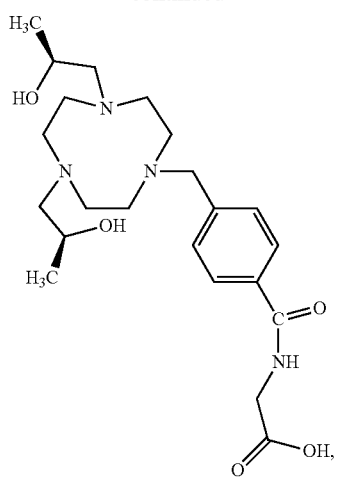
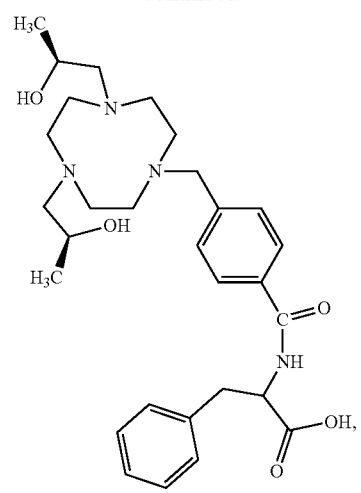
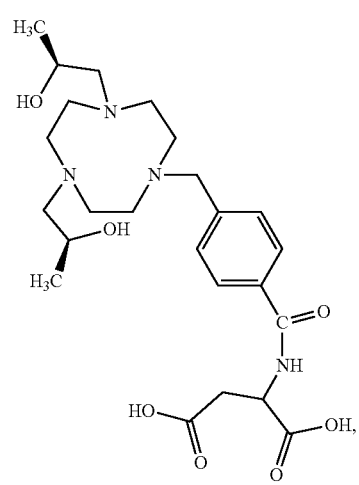
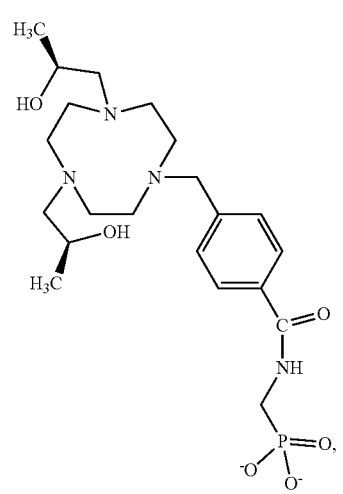
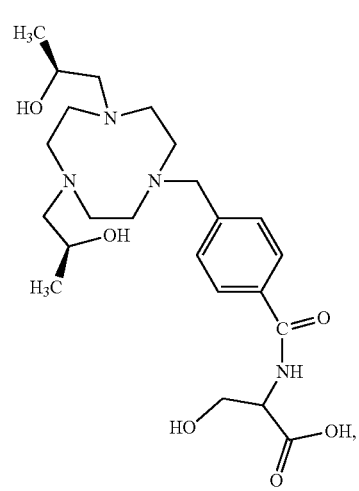
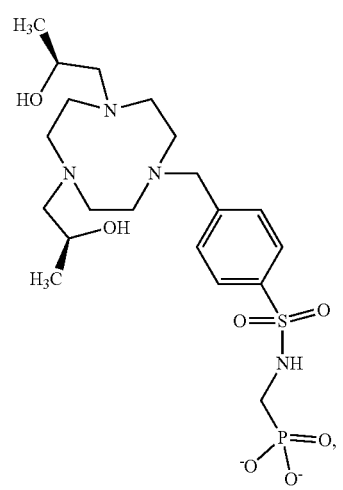

-continued
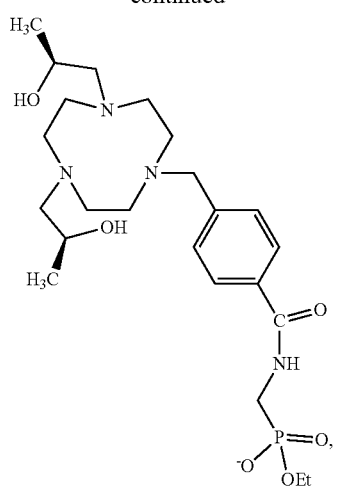
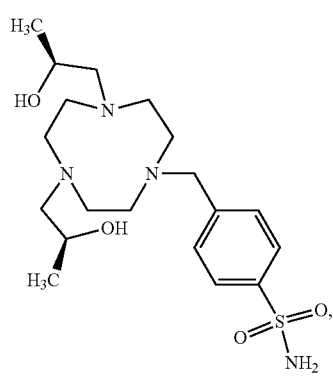
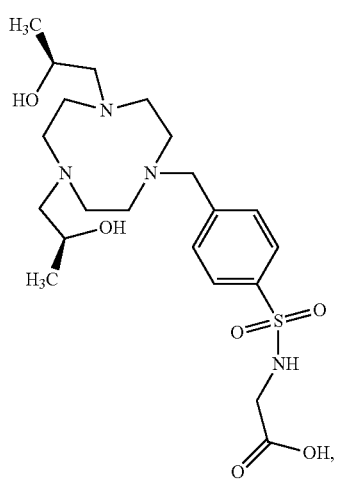
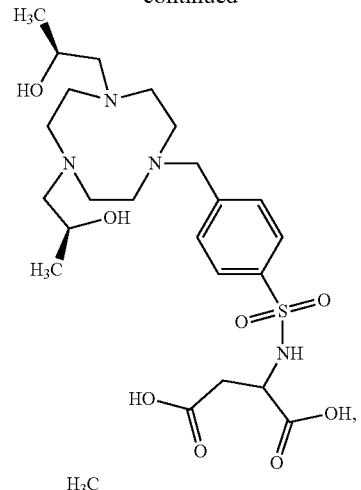
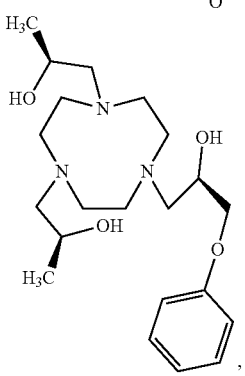
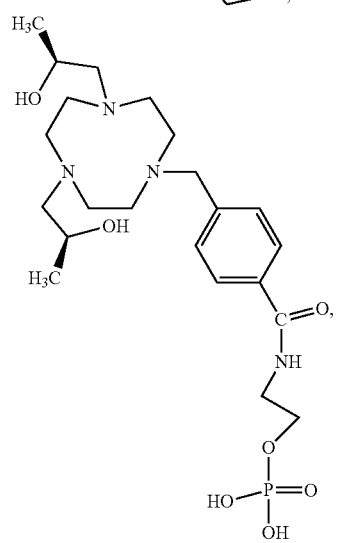
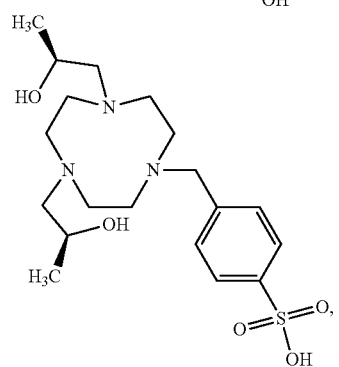

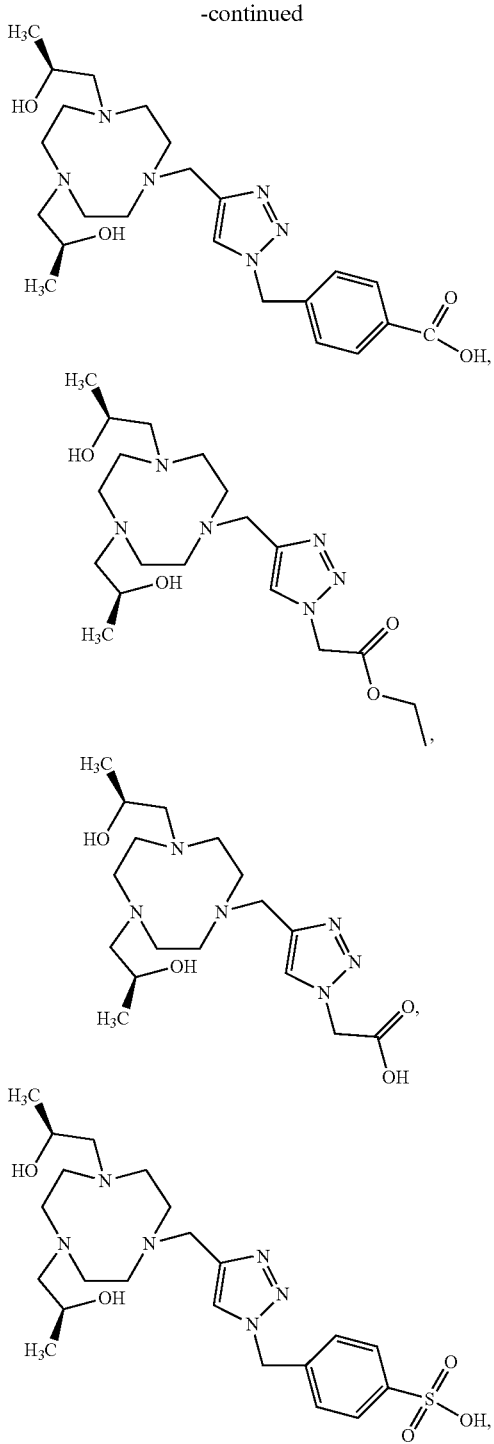

In some embodiments, when the macrocycle has Structure (I) of Scheme II and $Z_1$ and $Z_2$ are Structure 6 of Scheme III where $R_3$ is an unsubstituted ethyl, $Z_3$ is not Structure 6 of Scheme III where $R_3$ is an unsubstituted ethyl group. In further embodiments, when the macrocycle has Structure (I) of Scheme II and $Z_1$ and $Z_2$ are Structure 6 of Scheme III where $R_3$ is an unsubstituted or substituted ethyl, $Z_3$ is not Structure 6 of Scheme III where $R_3$ is an unsubstituted or substituted ethyl group. In added embodiments, when the macrocycle has Structure (I) of Scheme II and $Z_1$ and $Z_2$ are Structure 6 of Scheme III where $R_3$ is an unsubstituted alkyl, $Z_3$ is not Structure 6 of Scheme III where $R_3$ is an unsubstituted alkyl. In still other embodiments, when the macrocycle has Structure (I) of Scheme II and $Z_1$ and $Z_2$ are Structure 6 of Scheme III where $R_3$ is an unsubstituted or substituted alkyl, $Z_3$ is not Structure 6 of Scheme III where $R_3$ is an unsubstituted or substituted alkyl.

In particular embodiments, when the macrocycle has Structure (I) of Scheme II and $Z_1$ and $Z_2$ are Structure 7 of Scheme III, $Z_3$ is not Structure 7 of Scheme III.

In certain embodiments, when the macrocycle has Structure (I) of Scheme II and $Z_1$ and $Z_2$ are Structure 8 of Scheme III where $R_3$ is alkyl having a terminal hydroxyl substitution, $Z_3$ is not Structure 8 of Scheme III where $R_3$ is not alkyl having a terminal hydroxyl substitution. In further embodiments, when the macrocycle has Structure (I) of Scheme II and $Z_1$ and $Z_2$ are Structure 8 of Scheme III where $R_3$ is a substituted alkyl, $Z_3$ is not Structure 8 of Scheme III where $R_3$ is a substituted alkyl.

In some embodiments, when the macrocycle has Structure (II) of Scheme II and $Z_1$ and $Z_2$ are Structure 8 of Scheme III where $R_4$ is alkyl having a terminal hydroxyl substitution, $R_1$ is not alkyl having a terminal aryl group. In additional embodiments, when the macrocycle has Structure (II) of Scheme II and $Z_1$ and $Z_2$ are Structure 8 of Scheme III where $R_4$ is alkyl having a terminal hydroxyl substitution, $R_1$ is not substituted alkyl.

In certain embodiments, Fe(III) is complexed to the macrocycle. In other embodiments, Fe(III) is not complexed to the macrocycle. The Fe(III) may be complexed to the macrocycle as shown herein.

Without intending to be bound by any particular theory, it is considered that when bound to Fe(III), the macrocycles described herein can stabilize the trivalent iron (Fe(III)) state. The coordination geometry is designed for desirable binding of Fe(III) in comparison to Fe(II) to maintain the Fe(III) oxidation state, for example, under biologically relevant conditions. Stabilization of the Fe(III) state ($E_o$<0 mV vs. NHE) also serves to inhibit the production of reactive oxygen species that occur through reduction to the Fe(II) state of the complex.

It is desirable that the Fe(III) center is stabilized relative to Fe(III) so that there is no reaction with biological reductants to produce reactive oxygen species (ROS). Such redox-inactive Fe(III) centers have negative redox potentials versus NHE. Examples of macrocyclic complexes of the present with macrocyclic core and pendent groups that produce stabilized Fe(III) include, but are not limited to, 1,4,7-triazacyclononane macrocyclic core and alcohol pendent groups that become deprotonated upon binding of Fe(III).

In various examples, a macrocyclic compound or compound of the present disclosure exhibits a reduction potential ($E_o$) of less than 0 mV vs. normal hydrogen electrode (NHE) in aqueous solution at a biologically relevant pH (e.g., a pH of 6.5-7.5 or 7.2-7.4). In various other examples, a macrocyclic compound or compound of the present disclosure exhibits a reduction potential ($E_o$) of at least −100, at least −150, at least −200, at least −300, at least −400, at least −500, or at least −600 mV vs. normal hydrogen electrode (NHE) in aqueous solution at a biologically relevant pH (e.g., a pH of 6.5-7.5 or 7.2-7.4). In various other examples, a macrocyclic compound or compound of the present disclosure exhibits a reduction potential ($E_o$) of less than 0, more negative than −100, more negative than −150, more negative than −200, more negative than −300, more negative than −400, more negative than −500, or more negative than −600 mV vs. normal hydrogen electrode (NHE) in aqueous solution at a biologically relevant pH (e.g., a pH of 6.5-7.5 or 7.2-7.4).

In various other examples, a macrocyclic compound or compound of the present disclosure exhibits a reduction potential ($E_o$) of less than 0 to −600 mV vs. normal hydrogen electrode (NHE) in aqueous solution at a biologically relevant pH (e.g., a pH of 6.5-7.5 or 7.2-7.4). In various other examples, a macrocyclic compound or compound of the present disclosure exhibits a reduction potential ($E_o$) of 0 to −600 mV vs. normal hydrogen electrode (NHE) in aqueous solution at a biologically relevant pH (e.g., a pH of 6.5-7.5 or 7.2-7.4).

The shortening of the $T_1$ relaxation times of the protons of water, $T_1$ relaxivity, is promoted by both innersphere water and outersphere water. Accordingly, in various examples, macrocyclic complexes and compounds of the present disclosure comprise one or more pendent donor groups that can hydrogen bond to water through heteroatoms such as, for example, oxygen or nitrogen. Non-limiting examples of such pendent donor groups are pendent alcohol groups that deprotonate to alkoxide groups, phosphinates, and phosphonates that form hydrogen bonds to second sphere water. In addition, in various examples, macrocyclic compounds and compounds of the present disclosure comprise an open coordination site for binding water. These water ligands may ionize to form hydroxide ligands at neutral pH for example, as shown by, pH-potentiometric titrations. It may be desirable that the water ligands are rapidly exchanging. Evidence for rapidly exchanging water ligands is shown by variable temperature $^{17}O$ NMR spectroscopy studies. The reduced transverse relaxation times ($T_{2r}$) is approximated by measurement of the linewidth of the $^{17}O$ resonance.

The coordination chemistry of Fe(III) is dependent on the coordination number. The compounds of the present disclosure have donor groups which can be part of the macrocyclic core, also referred to as macrocycle donors, and donor groups can be part of the substituents on the macrocyclic core, also referred to as pendent (or pendent) donors. In an embodiment, when Fe(III) is complexed to the compound of the present disclosure, 4 to 7 donors can be complexed to the metal ion center. In an embodiment, the macrocyclic core can have from 2 to 4 donors and from 1 to 4 (e.g., 2 to 4) pendent donors, including all combinations thereof. In various embodiments, there are 2 macrocycle donors and 3 pendent donors, 2 macrocycle donors and 4 pendent donors, 3 macrocycle donors and 1 pendent donor, 3 macrocycle donors and 2 pendent donors, 3 macrocycle donors and 3 pendent donors.

Scheme VIII presents some macrocyclic complexes (with Fe(III)) that are within the scope of the present disclosure.

SCHEME VIII

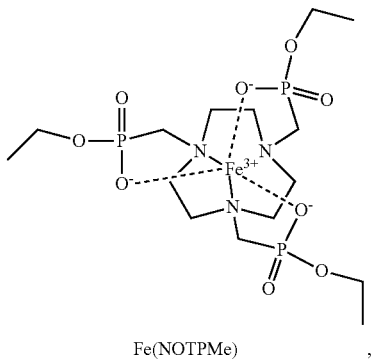

Fe(NOTPMe)

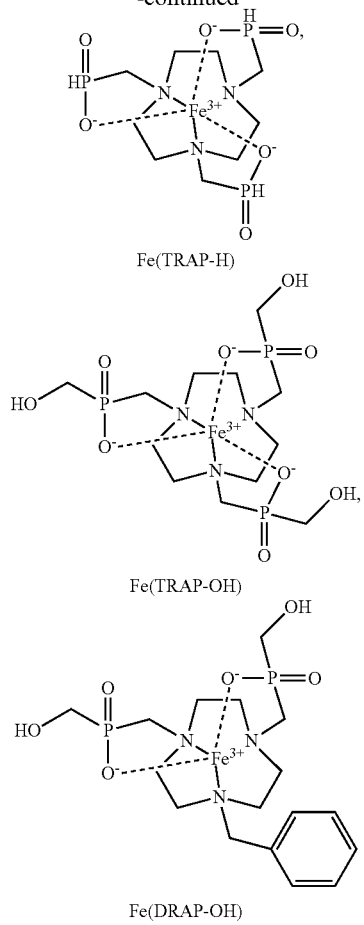

Fe(TRAP-H)

Fe(TRAP-OH)

Fe(DRAP-OH)

As used herein, the macrocyclic complex refers to the macrocyclic compound complexed with Fe(III). In some embodiments of the macrocyclic complex, when the macrocycle has Structure (I) of Scheme II and $Z_1$ and $Z_2$ are Structure 5 of Scheme III, $Z_3$ is not Structure 5 of Scheme III.

In some embodiments of the macrocyclic complex, when the macrocycle has Structure (I) of Scheme II and $Z_1$ and $Z_2$ are Structure 8 of Scheme III where $R_4$ is an unsubstituted aryl, $Z_3$ is not Structure 8 of Scheme III where $R_4$ is an unsubstituted aryl.

In an embodiment, the compounds of the present disclosure can have more than one macrocyclic core tethered together via an aromatic (e.g., aryl) group, macrocycle, polymer, dendrimer, protein, or peptide.

SCHEME IX

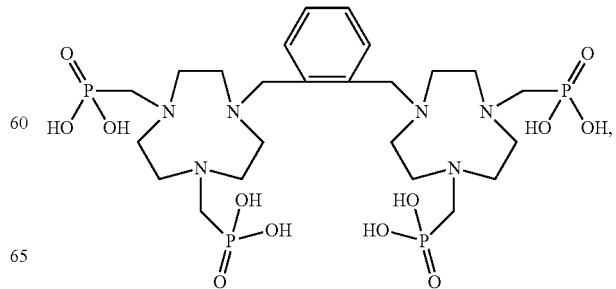

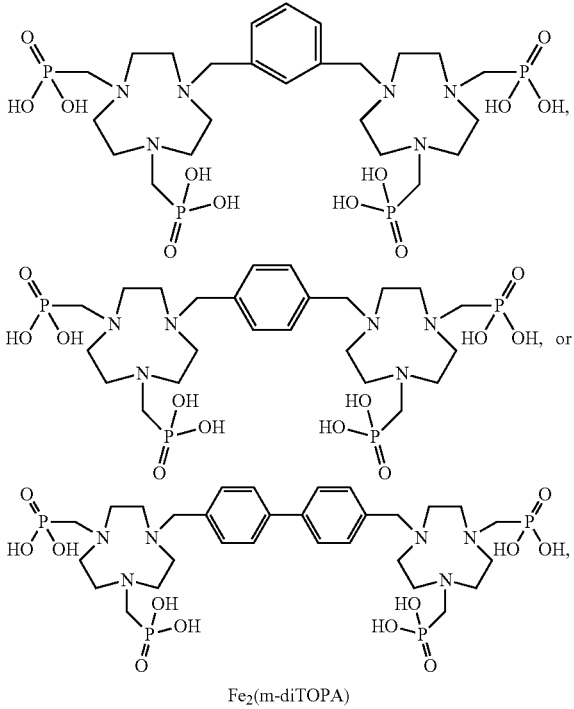

Fe₂(m-diTOPA)

For tumor uptake and retention, the size of the molecule containing the contrast agent is important. In addition, given that the magnitude of the $T_1$ relaxivity increases proportionally with the number of iron complexes and also increase with the size of the molecule, or more precisely the rotational correlation time ($\tau_c$), the use of multiple tethered macrocyclic complexes should increase contrast. An increase in $\tau_c$ can also be accomplished by binding to blood proteins, especially human serum albumin (HSA). Certain ligand functional groups promote binding to human serum albumin (HSA). Typically, these contain anionic groups and aromatic groups (e.g., aryl groups).

In various embodiments, the compounds of the present disclosure are a salt, a partial salt, a hydrate, a polymorph, or a stereoisomer or a compound of the present disclosure, or a mixture thereof. For example, the compound can be present as a racemic mixture, a single enantiomer, a single diastereomer, or mixture of diastereomers. In certain embodiments, after complexation of the metal, the compounds are present as mixtures of diastereomers and/or conformers which can be determined by NMR. The diastereomers arise from the conformation of the macrocyclic core and the directionality of the substituents on the macrocyclic core.

The compounds of the present disclosure can have innersphere water or alternatively, a hydroxide ligand. In an embodiment the compounds have one innersphere ligand (q) which contributes to relaxivity as in Eq. 1.

$$r1 = r1^{SS} + r1^{IS} \quad \text{Equation 1}$$

$$r_1^{IS} = \frac{q/[H_2O]}{T_{1m} + \tau_m} \quad \text{Equation 2}$$

Eq. 1 shows that relaxivity has contributions from bound water (innersphere, IS) and second-sphere (SS) and (outersphere) water. Eq. 2 predicts that greater numbers of bound water molecules and rapid ligand exchange rate constants (short lifetimes for bound water (Tm)) are advantageous. Notably $r_1$, the parameter used to characterize relaxivity, has units of mM$^{-1}$ s$^{-1}$, and is obtained from a plot of $T_{1obs}$ (s$^{-1}$) versus contrast agent concentration. There is an analogous relationship for second-sphere waters although the number and residence time is not well defined. The $r_1$ and $r_2$ relaxivity (from $T_1$ and $T_2$ relaxation rate constants at 4.7 T at 37° C.) is summarized in Table 1.

TABLE 1

$T_1$ Relaxivity of Fe(III) complexes at neutral pH, HEPES buffer, 37° C. on a 4.7 Tesla MRI scanner. HSA is human serum albumin.

| Complex | $r_1$(mM$^{-1}$s$^{-1}$) | $r_1$(mM$^{-1}$s$^{-1}$) with HSA | $r_2$ (mM$^{-1}$s$^{-1}$) | $r_2$ with HSA |
|---|---|---|---|---|
| Fe(TASO) | 2.3 | 2.0 | 3.5 | 4.5 |
| Fe(TRAP-Ph) | 2.9 | 3.5 | 7.7 | 6.5 |
| Fe(TOP) | 0.50 | 2.6 | 1.4 | 2.5 |
| Fe(NOTP) | 0.66 | 1.0 | 1.4 | 1.5 |

The structures of certain complexes in Table 1 are presented below.

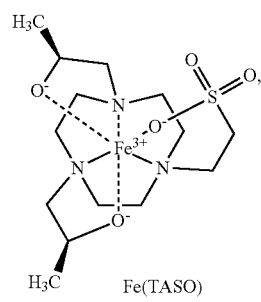

Fe(TASO)

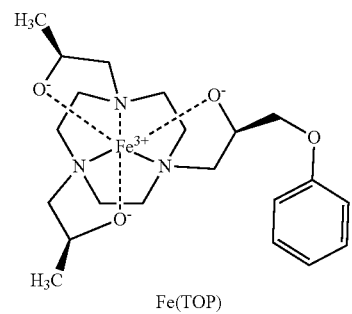

Fe(TOP)

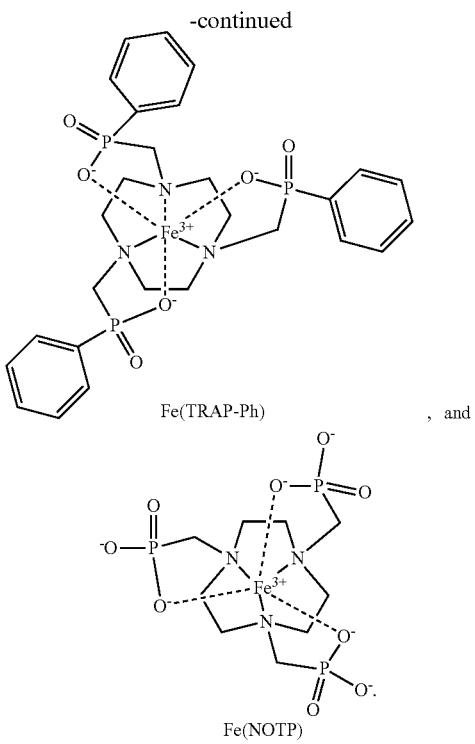

Fe(TRAP-Ph)                , and

Fe(NOTP)

Notably, it is desirable that the ratio of the $T_1$ to $T_2$ relaxivity ($r_1/r_2$) of a macrocyclic complex or compound of the present disclosure be as close to one (unity) as possible. $r_2$, the transverse relaxivity, is by definition always larger than $r_1$, the longitudinal relaxivity. In various preferred examples, the Fe(III) contrast agents of the present disclosure have low $r_2$ to give $r_1/r_2$ ratios close to one, for example, as shown in Table 1. In various examples, a macrocyclic complex or compound of the present disclosure has an $r_1/r_2$ ratio of 0.3 to 1.0. These data show the desirability of the TACN ligand, alcohol pendents and an open coordination site, for example, in Fe(TASO) in comparison to complexes with no open coordination site for the mononuclear complexes such as, for example, Fe(TOP) (see, e.g., Table 1). However, pendent groups such as phosphonate and phosphinate are expected to have strong second sphere interactions to increase $r_1$ such as shown with Fe(TRAP-Ph) in Table 1.

Table 1 shows that interaction of the Fe(III) complex with water molecules can enhance relaxation of the protons of the water. Without being bound by any particular theory, it is considered that exchange of innersphere water with bulk water is an important mechanism for proton relaxivity. However, Fe(III) is a much smaller metal ion than Gd(III) (0.78 Å vs. 1.25 Å, respectively). The shorter M–H distance in bound water of Fe(III) compared to Gd(III) suggests that the relative efficiency of the second-sphere versus innersphere contributions may differ for the two metal ion complexes.

There are three mechanisms that contribute to paramagnetic relaxation of associated water ($1/T_{1m}$): the scalar (contact) contributions, dipole-dipole contributions and Curie spin relaxation. The most important of these for the longitudinal relaxation considered here is the dipole-dipole contribution ($1/T_1DD$). At field strengths of 1.5 T or greater, $1/T_1DD$ is defined as shown in Eq. 3 where S is the spin quantum number, $\omega_H$ is the Larmor frequency of the proton, $r_{MH}$ is the metal ion-proton distance and $\gamma_H$ is the proton gyromagnetic ratio, ge is the electronic g factor, $\mu_B$ is the Bohr magneton, and $\mu_o$ is the permittivity of a vacuum. Notably, the $1/T_1DD$ term increases (higher relaxivity) with larger total spin (S) which favors Gd(III) over Fe(III). However, the shorter distance of the paramagnetic Fe(III) center to water protons ($r_{MH}$) favors Fe(III) proton relaxation, especially given the $1/r^6$ dependence.

$$\frac{1}{T_1^{DD}} = \frac{2}{15}\left(\frac{\mu_0}{4\pi}\right)\frac{\gamma_H^2 g_e^2 \mu_B^2 S(S+1)}{r_{MH}^6}\left[\frac{3\tau_c}{1+\omega_H^2\tau_c^2}\right] \quad \text{Equation 3}$$

$$\frac{1}{\tau_c} = \frac{1}{\tau_R} + \frac{1}{T_{1e}} + \frac{1}{\tau_m} \quad \text{Equation 4}$$

Figure 6:
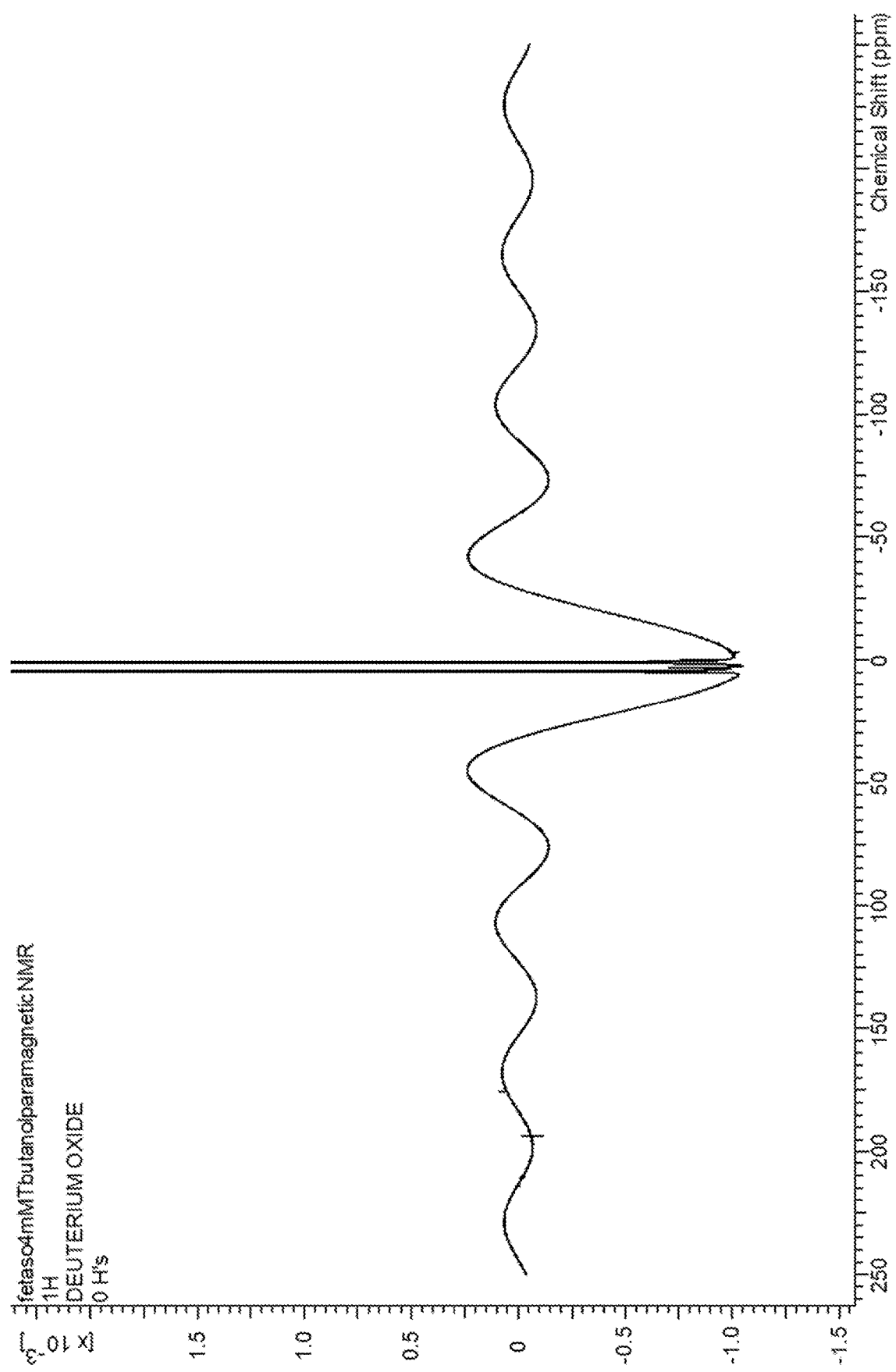
FIG. 6 shows that the $^1$H NMR of Fe(TASO) is broadened into the baseline, consistent with high spin Fe(III). A shift in the t-butanol proton resonance is observed.

The correlation time ($\tau c$) for the dipolar relaxation mechanism is influenced by different processes including the lifetime of the bound water ($1/\tau_m$), the rotational motion of the contrast agent ($1/\tau_R$) and the longitudinal relaxation of the upaired electrons ($1/T_{1e}$). Although any of these three processes can contribute, their importance depends on the strength of the magnetic field. Much of the literature is focused on the importance of these processes at low field strength (<1 T). Under these conditions, the rotational processes or electronic relaxation times may be limiting, and $\tau_m$ should be in a narrow range close to 10 ns ($k_{ex}=10^8$ s$^{-1}$). However at higher field strengths (≥1.5 T), simulations show that the optimal $\tau_m$ has a larger range (1-100 ns) and rotational motions should have values intermediate between small molecules and proteins. An important parameter is $T_{1e}$, the electronic relaxation time. A long $T_{1e}$ for Fe(III) may result from complexes that have a high degree of symmetry, leading to little zero field splitting and slow relaxation of the electronic state. Also, the coordination sphere needs to favor high spin (S=5/2) and not low spin S=½ Fe(III). The lack of a defined $^1$H NMR spectrum for Fe(TASO) also is consistent with a high spin Fe(III) that efficiently relaxes water protons (FIG. 6). The solution effective magnetic moment $\mu_{eff}$ of 5.8 is also consistent with a S=5/2 state.

Studies to determine whether a metal complex has a bound water can involve the collection of variable temperature $^{17}$O NMR data. The data in FIG. 8 were obtained using a Varian 400 MHz NMR spectrometer with a broad band probe. Since the $^{17}$O isotope has a low natural abundance, each complex was dissolved into a solution of water enriched with $H_2^{17}O$ such that the peak measured by the NMR would be larger and therefore easier to detect visually. NMR studies were performed at various temperatures. The temperature range for Fe(TASO) was between 298 K and 340 K. The temperature dependent transverse relaxation data were fit to various equations via a least squares fit analysis using Scientist for Windows version 3.0. First, it is known that complexes with an open coordination site, obey the Swift-Connick equation, as shown in equation 5a:

$$\frac{1}{T_{2r}} = \frac{\pi}{P_m} * (\Delta\nu_{observed} - \Delta\nu_{solvent}) = \quad \text{Equation 5a}$$

$$\frac{1}{\tau_m} * \frac{(T_{2m}^{-1} + T_{2m}^{-1} * \tau_m^{-1} + \Delta\omega_m^2)}{(T_{2m}^{-1} + \tau_m^{-1})^2 + \Delta\omega_m^2} + \frac{1}{T_{2os}}$$

where $$\frac{1}{T_{2r}}$$

is the reduced transverse relaxation rate, $P_m$ is the molar fraction of bound water and $(\Delta v_{observed} - \Delta v_{solvent})$ is the difference in line widths between $H_2^{17}O$ with and without complex present. Since the observed line widths can be measured using NMR spectroscopy, and $P_M$ can be calculated in advance, they are the measurable quantities in the equation. In addition, $$\frac{1}{\tau_m}$$

is the residence time of the bound water molecules, $T_{2m}^{-1}$ is the transverse relaxation rate of the bound water and $\Delta\omega_m$ is the chemical shift difference between bound and bulk water. The $T_{2OS}$ is a term taking into account the hydrogen bonding of ligand atoms to bulk water.

In the complexes studied at the temperature ranges in which data were recorded and analyzed, $$T_{2m}^{-1} \text{ and } \frac{1}{T_{2os}}$$

can be neglected and the Swift-Connick equation is reduced to equation 5b. In conjunction, since reduced transverse relaxation rates are often quite large, taking the natural logarithm of both sides of the equation allows for better scaling and simpler representation of the data, as shown in equation 5c:

$$\frac{1}{T_{2r}} = \frac{\pi}{P_m} * (\Delta v_{observed} - \Delta v_{solvent}) = \frac{1}{\tau_m} * \frac{\Delta\omega_m^2}{\tau_m^{-2} + \Delta\omega_m^2}. \quad \text{Equation 5b}$$

$$\ln\left(\frac{1}{T_{2r}}\right) = \ln\left(\frac{1}{\tau_m} * \frac{\Delta\omega_m^2}{\tau_m^{-2} + \Delta\omega_m^2}\right). \quad \text{Equation 5c}$$

The inverse bound water residence time, and the chemical shift difference between bound and bulk water are each represented by equations 6a and 6b, respectively:

$$\frac{1}{\tau_m} = k_{ex} = \frac{k_b * T}{h} * \exp\left(\frac{\Delta S^{\ddagger}}{R} - \frac{\Delta H^{\ddagger}}{RT}\right). \quad \text{Equation 6a}$$

$$\Delta\omega_m = \frac{g_L \mu_b S(S+1)B}{T}\left(\frac{A}{\hbar}\right). \quad \text{Equation 6b}$$

Figure 8:
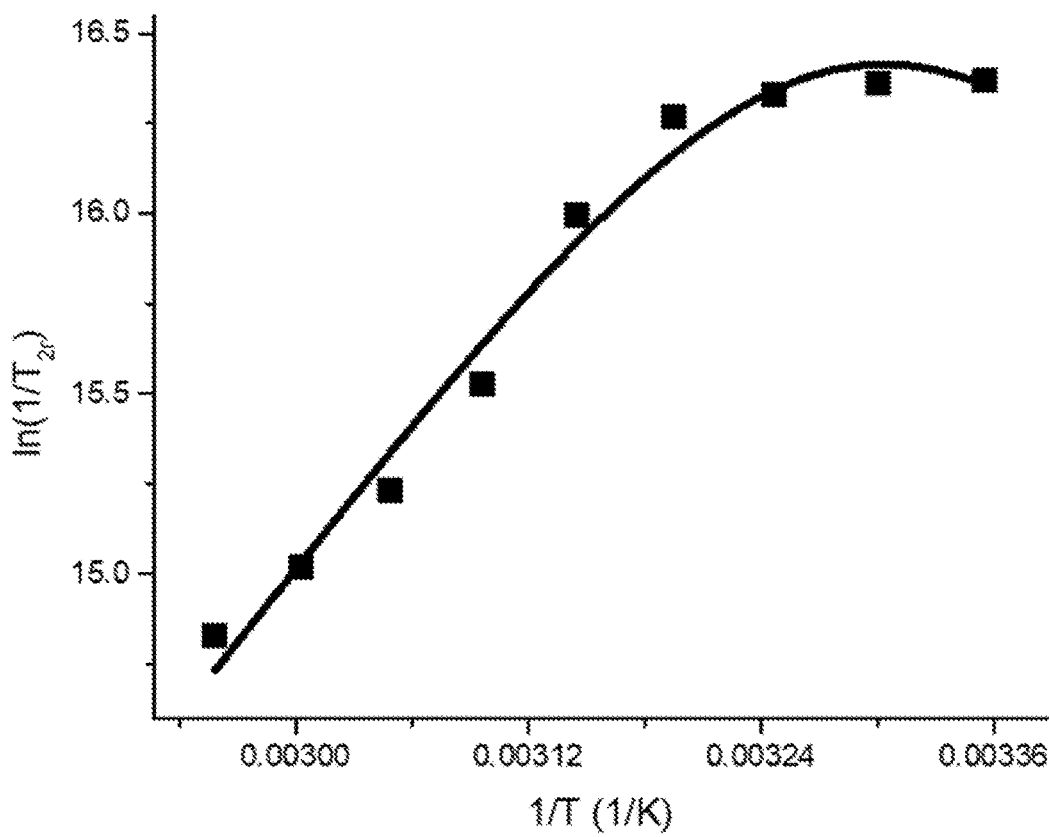
FIG. 8 shows a plot of data from variable temperature $^{17}$O NMR studies. The natural log of the inverse of the transverse relaxivity of the $^{17}$O NMR resonance as a function of temperature is shown for an experiment containing 20 mM Fe(TASO) at pH 4.5.
Figure 13:
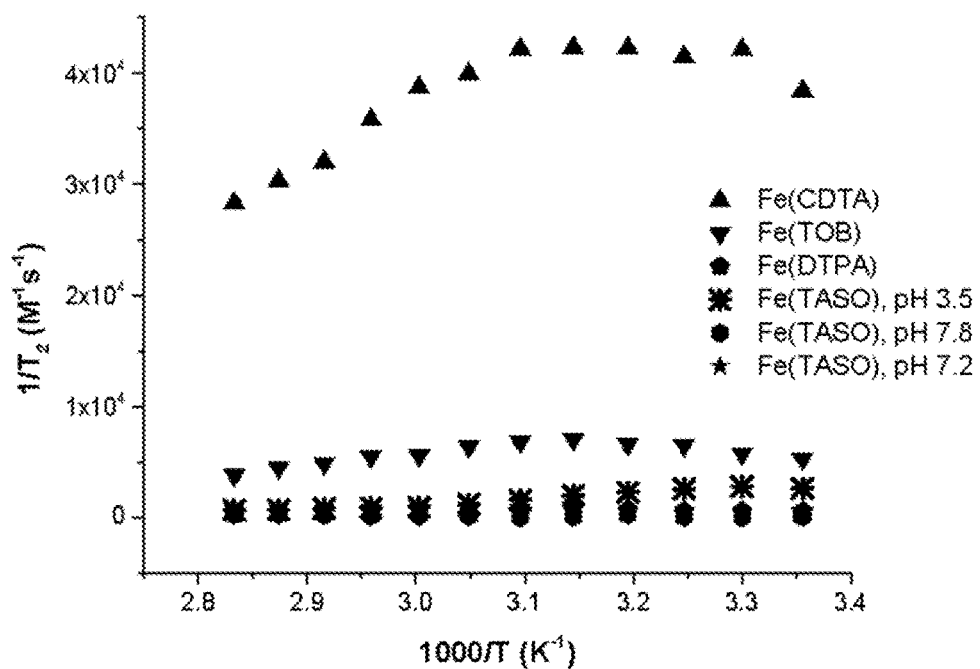
FIG. 13 shows transverse $^{17}$O NMR relaxivity, $\ln(1/T_{2r})$ as a function of temperature for Fe(TASO) in comparison to Fe(DTPA), Fe(TOB) and Fe(CDTA) measured over a range of pH values. Fe(CDTA) has an exchangeable water ligand, whereas Fe(DTPA) has no exchangeable innersphere water ligands.

In equation 6a, $k_{ex}$ is the water exchange rate constant at the coordination site and is the inverse of the bound water residence time. $k_b$ is Boltzmann's constant, h is Planck's constant, T represents absolute temperature, and $\Delta S^{\ddagger}$ and $\Delta H^{\ddagger}$ represent the activation entropy and enthalpy, respectively. In equation 6b, $g_L$ is the isentropic Lande factor, $\mu_b$ is the magnetic moment, S represents the total spin state, B represents the applied magnetic field, and $$\left(\frac{A}{\hbar}\right)$$

represents the hyperfine coupling constant. In equation 6b, the isentropic Lande factor, magnetic moment, spin state, magnetic field, and hyperfine coupling constant terms are consolidated into a single parameter which is solved for in the treatment of the data. This consolidation reduces equation 6a to a simple inverse temperature dependence and the simplified constant is represented by the constant C. This approach was used to study the exchange rate constant for bound water of Fe(TASO) as shown in FIG. 8. Additional studies over a range of pH values supported the lack of inner-sphere ligands at neutral pH (FIG. 13). This data compared Fe(CDTA), a complex with a bound water and Fe(DTPA), a complex lacking inner-sphere water and found that Fe(TASO) lacks a directly bound inner-sphere water. Thus, the $T_1$ relaxivity is produced by second-sphere and outersphere water molecules.

The compounds of the present disclosure are thermodynamically stable and/or kinetically inert towards dissociation. In an embodiment, the compounds are thermodynamically stable and kinetically inert towards dissociation. In an embodiment, the kinetic inertness of the compounds of the present disclosure can be described using a rate constant for dissociation. In an embodiment, the macrocyclic donors and pendent donors don't dissociate appreciably from the metal center for up to 24 hours at neutral pH in the presence of 1) 25 mM carbonate, 0.40 mM phosphate, 100 mM NaCl, pH 7.2.

In an embodiment, Fe(III) is high spin S=5/2. For effective $T_1$ (longitudinal) relaxation, a paramagnetic spin state is needed. In order to keep Fe(III) in the high spin state, the ligand (or crystal) field splitting must not be too large. If the crystal field splitting is larger than the pairing energy, a low spin (S=½) state will result. Fe(III) is readily maintained in a high spin paramagnetic state with a range of ligand donor groups, especially containing anionic oxygen or nitrogen donors.

Figure 7:
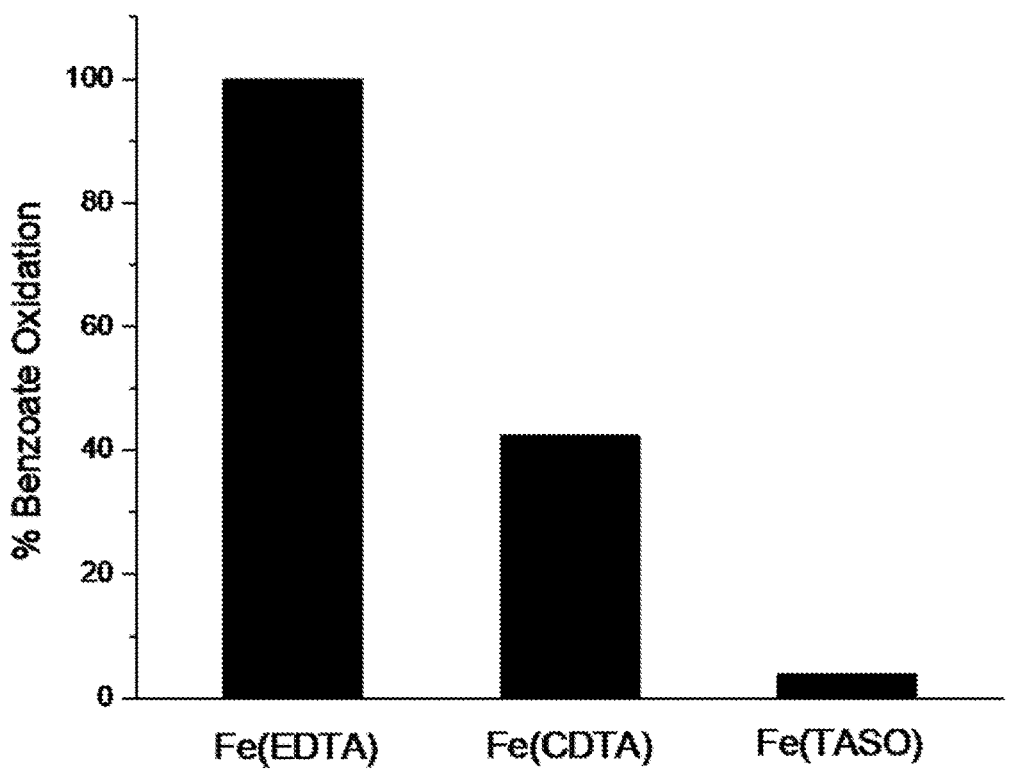
FIG. 7 shows that Fe(III) contrast agents such as Fe(TASO) do not oxidize benzoate in the presence of peroxide and ascorbate, unlike Fe(III) complex of EDTA or CDTA. Benzoate oxidation with 50 μM complex, 50 μM $H_2O_2$ and 50 μM ascorbate at pH 7.2. [Fe(EDTA)]$^-$ oxidation is set at 100%.

It is desirable that the Fe(III) complex remain in the trivalent oxidation state and not be reduced by peroxide, superoxide, ascorbate or by glutathione at concentrations present in the extracellular medium of cells such as, for example, mammalian cells (e.g., human cells). Normally, a redox potential more negative than zero mV (<0 mV) versus NHE is sufficient. If the complex were to be reduced to Fe(II) and the Fe(II) complex and the complex has a positive redox potential versus NHE, reactive oxygen species may be produced. For example, [Fe(EDTA)]− has a redox potential of approximately 300 mV and produces ROS as shown by the assay in FIG. 7.

For use in methods of the disclosure, the compounds or complexes described herein can be administered as pharmaceutical preparations. Thus, they can be provided in a variety of compositions, and can be combined with one or more pharmaceutically acceptable carriers. Some examples of pharmaceutically acceptable carriers can be found in: *Remington: The Science and Practice of Pharmacy* (2005) 21st Edition, Philadelphia, Pa. Lippincott Williams & Wilkins. The composition can be provided as a liquid, a solution, or a solid, and may be provided in combination with any suitable delivery form or vehicle, examples of which include but are not limited to caplets, capsules, tablets, an inhalant or aerosol, etc.

Various methods known to those skilled in the art may be used to introduce the compositions of the disclosure to an individual. These methods include but are not limited to intravenous, intramuscular, intracranial, intrathecal, intradermal, subcutaneous, and oral routes. In one embodiment, the composition is administered intravenously.

In certain embodiments, the complexes used in the methods of the present disclosure may have the following structures:

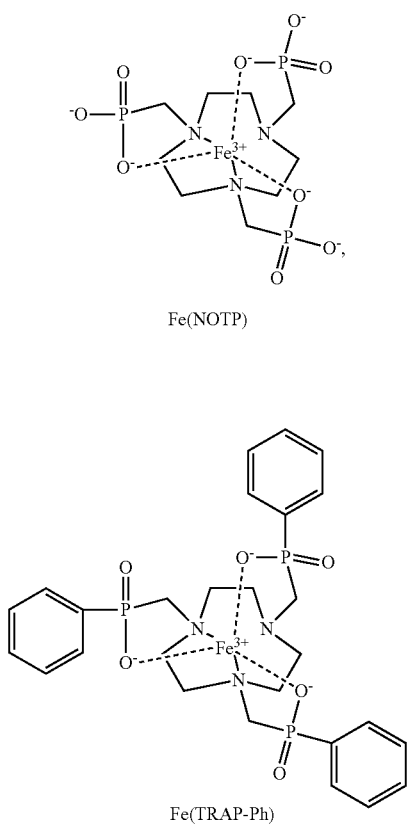

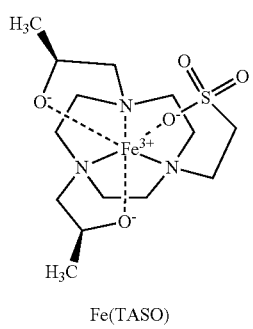

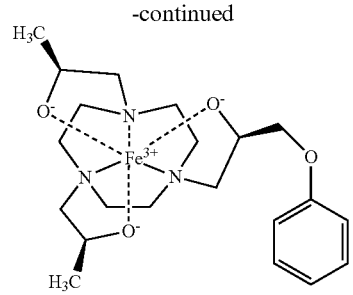

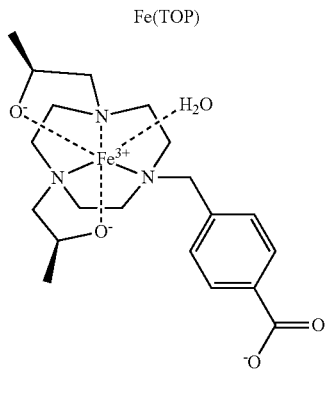

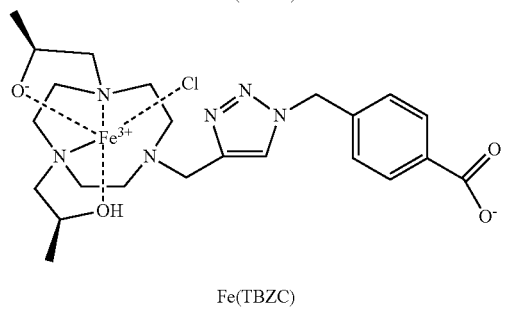

Figure 9:
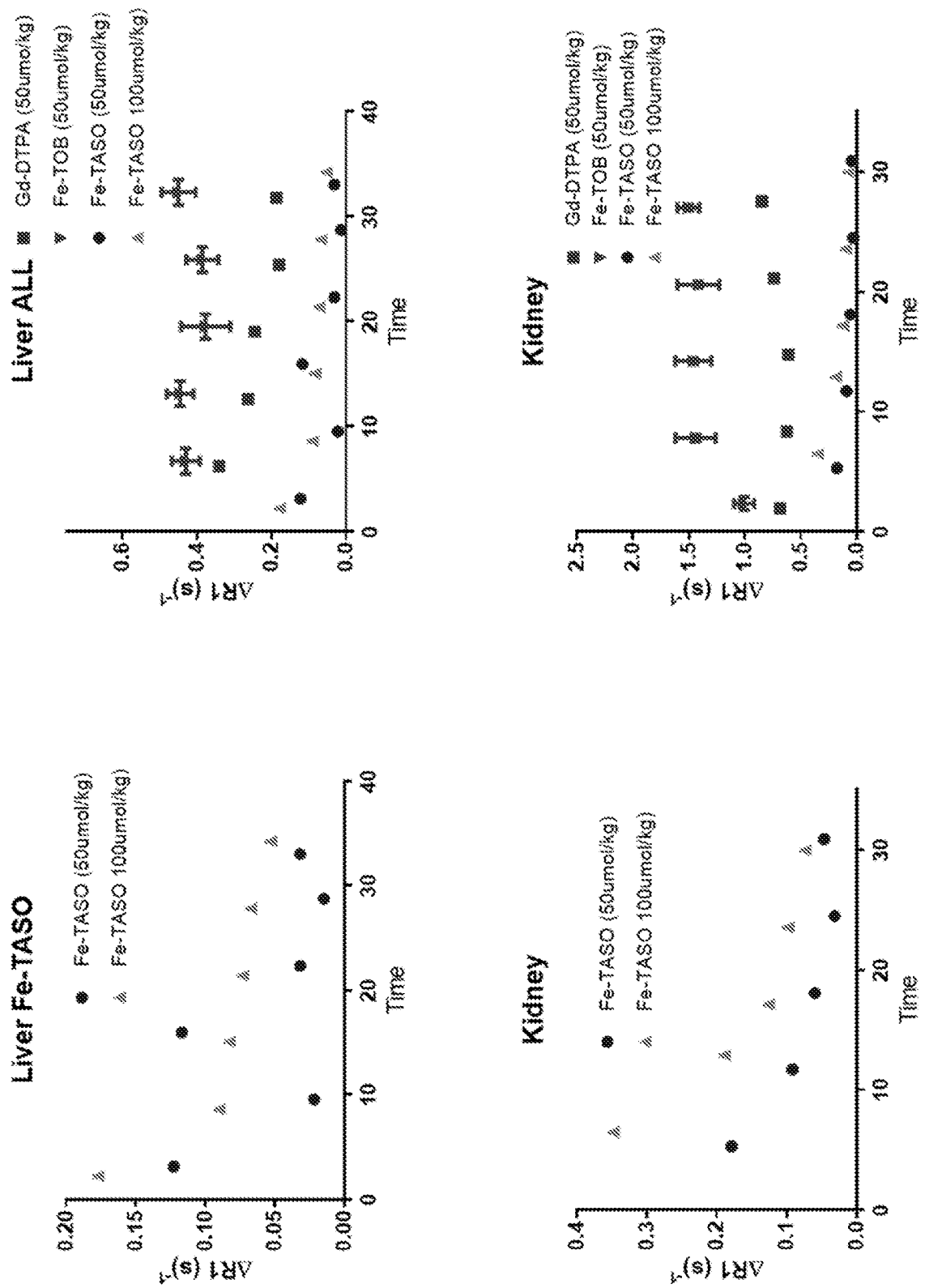
FIG. 9 shows plots of the change in $T_1$ relaxivity in the mouse over time after injection of Fe-TASO for various tissues including liver, kidney in comparison to Gd(DTPA) and Fe(TOB).
Figure 10:
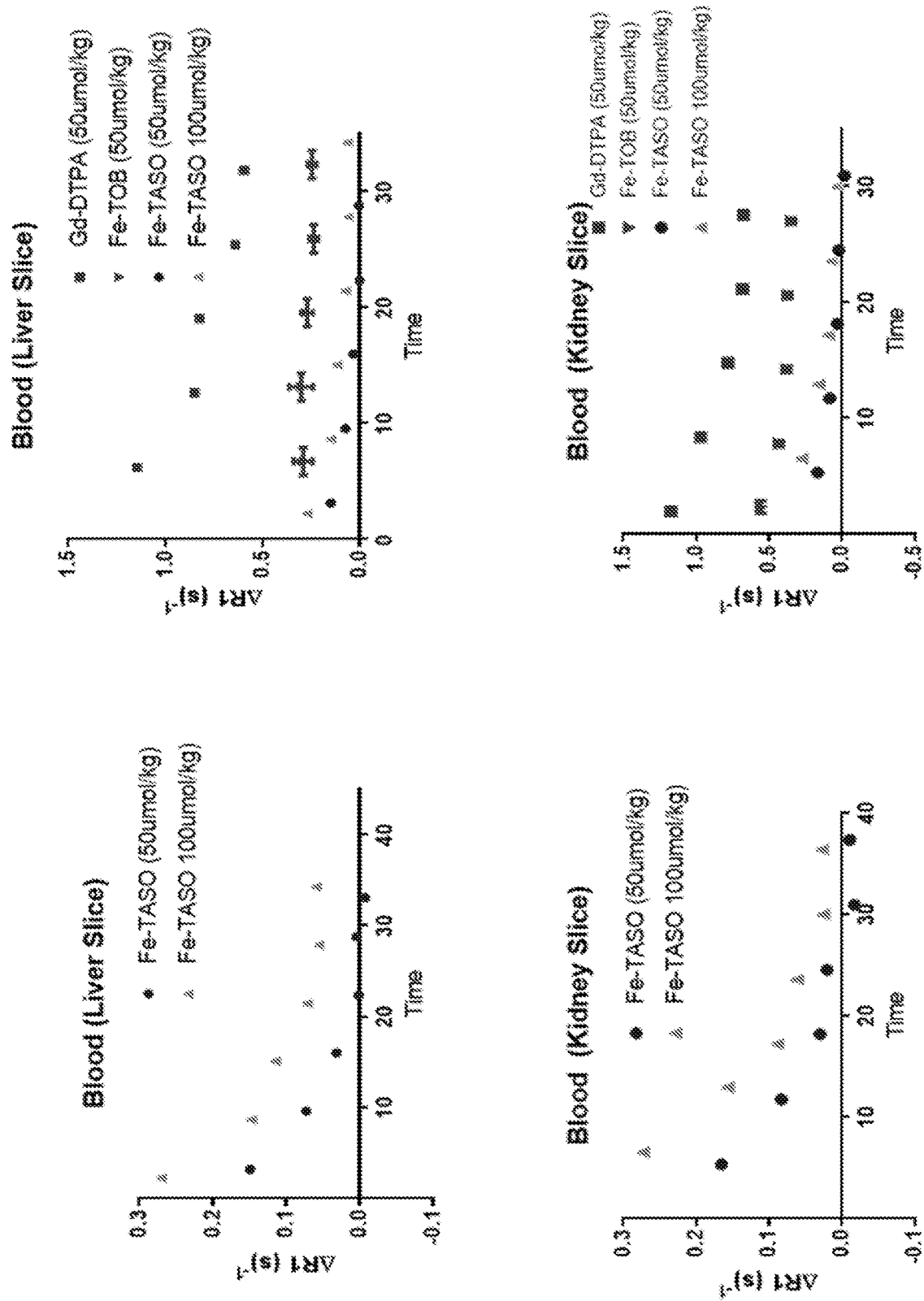
FIG. 10 shows plots of the change in $T_1$ relaxivity in the mouse over time after injection of Fe(TASO) in blood in comparison to Gd(DTPA) and Fe(TOB).

The necessary solubility of the complexes depends on their effectiveness in producing contrast. For Fe(III) $T_1$ contrast agents that have good relaxivity, the complexes need 100 $\mu M^{-2}$ mM solubility. However, other additives such as, for example, human serum albumin (HSA) or meglumine may be used to increase solubility or increase relaxivity. In a non-limiting example, a contrast agent having relaxivity of at least 1.5 $mM^{-1}$ $s^{-1}$ at 4.7 Tesla upon binding to human serum albumin in vitro may be considered to have good relaxivity. Addition of HSA (35 mg/mL) to some of the Fe(III) complexes may produce higher $T_1$ relaxivity as shown in Table 1. However, contrast agents with moderate relaxivity in a test tube (0.6 to 1.4 $mM^{-1}$ $s^{-1}$) may produce good contrast in vivo if the contrast agent interacts with an organ such as, for example, the kidneys or liver. Solubility is generally measured in aqueous solution at near neutral pH (6.5 to 7.5) in 100 mM NaCl with 25 mM carbonate and 0.4 mM phosphate at 37° C. The dose of the composition to be used will necessarily be dependent upon the needs of the individual to whom the composition of the disclosure is to be administered. These factors include but are not necessarily limited to the weight, age, sex, and medical history of the individual. Shown in FIGS. 9 and 10 are data from in vivo MRI studies done in mice. The contrast agent, Fe(TASO) was injected at 0.20 mL of 6.3 mM Fe(TASO) (10.5 mg of HSA or two equivalents of meglumine).

In an aspect, the present disclosure provides imaging methods using the macrocyclic compounds described herein. The imaging methods use magnetic resonance imaging methods. Examples of such methods include, but are not limited to, magnetic resonance imaging (MRI).

Specifically, the macrocyclic compounds of the present disclosure, when complexed to Fe(III), can be used as $T_1$ MRI contrast agents. These complexes may have properties that change with alterations in pH. Such properties make these complexes useful for mapping pH to enable better therapeutic treatment of diseases such as, for example, cancer, stroke and heart disease. When complexed with Fe(III), the macrocycles may also be used as $T_2$ MRI contrast agents.

The imaging methods of the present disclosure can be used to image a cell, tissue, organ, vasculature, or a part thereof. The cell, tissue, organ, vasculature can be a part of an individual. By "individual" it is meant a human or animal. In an embodiment, the present disclosure provides a method to obtain an image of at least a portion of a cell, tissue, organ, or vasculature comprising the steps of: contacting a cell, tissue, organ, or vasculature with the compounds of the present disclosure, and imaging at least a portion of the cell, tissue, organ, or vasculature to obtain an image of the portion of cell, tissue, organ, or vasculature. At least part of a cell, tissue, or organ can be alive or dead. Likewise, the individual can also be alive or deceased.

In an embodiment, the macrocyclic compound can be complexed with Fe(III) and used as a $T_1$ MRI contrast agent. This contrast is produced by $T_1$ weighted imaging to give positive contrast in the region where the iron complexes accumulate. The complexes are high spin Fe(III) under biologically reducing conditions either innersphere or outersphere water interactions that give a decrease in the $T_1$ relaxation times of bulk water protons.

The following Statements provide non-limiting examples of macrocyclic complexes, macrocycle compounds, and imaging methods of the present disclosure:

Statement 1. A macrocyclic complex comprising:

a 1,4,7-triazacyclononane (TACN) moiety or a substituted TACN moiety (e.g., an 0-substituted TACN moiety or an S-substituted TACN moiety);

one or more anionic pendent groups that are substituents on the TACN moiety independently chosen from:

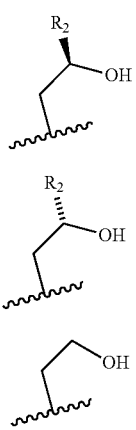

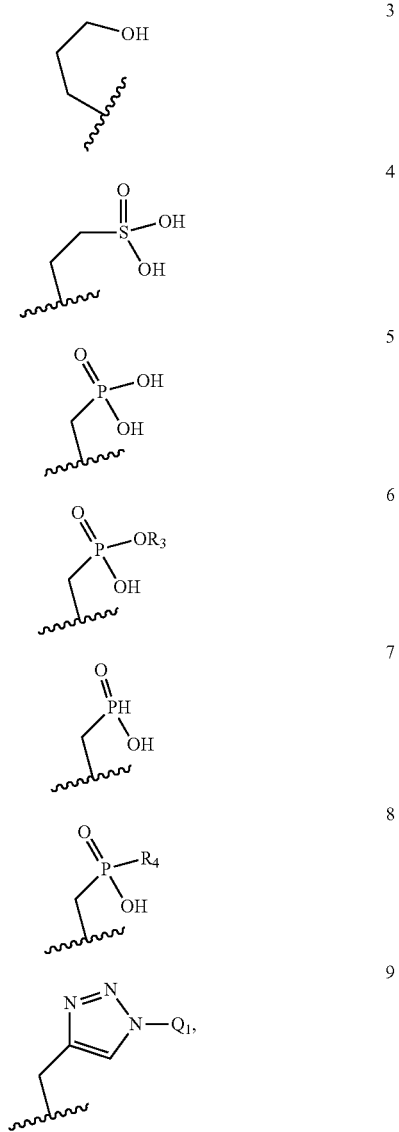

substituted analogs thereof, deprotonated analogs thereof, stereoisomers thereof, and combinations thereof, where $R_2$ is a substituted or unsubstituted alkyl group, a substituted or unsubstituted aromatic group, which may be an aryl group, or a substituted ether; $R_3$ is a substituted or unsubstituted alkyl or a substituted or unsubstituted aryl group; $R_4$ is a substituted alkyl (e.g., substituted with a hydroxyl or a carboxylate group, or the like) or unsubstituted alkyl or a substituted or unsubstituted aryl group; and $Q_1$ is aryl substituted with an anionic group (such as, for example, a carboxylate, sulfonate, phosphonate, phosphate ester or phosphinate), an alkyl group substituted with an anionic group (such as, for example, a carboxylate, sulfonate, phosphonate, phosphate ester or phosphinate) or an aralkyl group substituted with an anionic group (such as, for example, a carboxylate, sulfonate, phosphonate, phosphate ester or phosphinate); and a high-spin Fe(III) cation complexed to i) the TACN moiety or the substituted TACN moiety and ii) at least one anionic pendent group substituent of the macrocyclic compound (e.g., the TACN moiety or the substituted TACN moiety), or a salt, a partial salt, a hydrate, a polymorph, or a stereoisomer thereof.

Statement 2. A macrocyclic complex according to Statement 1, where:
when the macrocycle has Structure (I) of Scheme II and $Z_1$ and $Z_2$ are Structure 5 of Scheme III, $Z_3$ is not Structure 5 of Scheme III; and/or
when the macrocycle has Structure (I) of Scheme II and $Z_1$ and $Z_2$ are Structure 8 of Scheme III where $R_4$ is an unsubstituted aryl, $Z_3$ is not Structure 8 of Scheme III where $R_4$ is an unsubstituted aryl.

Statement 3. A macrocyclic complex according to Statement 1 or 2, where at least one or all of the one or more pendent groups is covalently bound to a nitrogen atom on the TACN moiety.

Statement 4. A macrocyclic complex according to any one of the preceding Statements, where the macrocyclic complex has at least one open coordination site.

Statement 5. A macrocyclic complex according to any one of the preceding Statements, where the macrocyclic complex has at least one water and/or at least one hydroxide complexed to the high-spin Fe(III) cation.

Statement 6. A macrocyclic complex according to any one of the preceding Statements, where at least one of the pendent groups is substituted at a benzylic position or any carbon the alkyl group leading to the heteroatom of the pendent group.

Statement 7. A macrocyclic complex according to any one of the preceding Statements, where the macrocyclic complex further comprises one or more ancillary group(s) (e.g., one or more coordinating pendent group(s), one or more non-coordinating pendent group(s), or a combination thereof).

Statement 8. A macrocyclic complex according to Statement, where the coordinating pendent group or non-coordinating pendent group has the following structure:

Scheme V

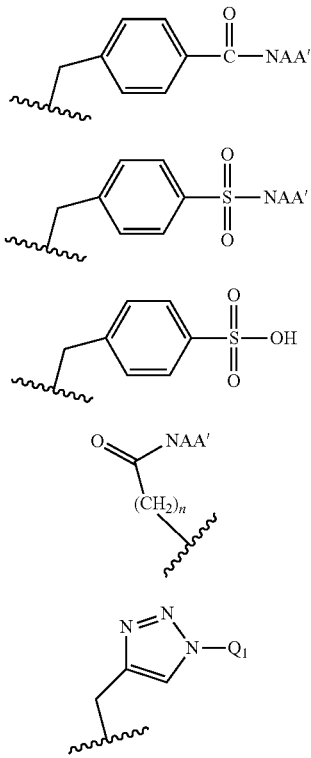

where A and A' are each independently a substituted or unsubstituted $C_1$ to $C_{12}$ alkyl group of linear or branched structure or a proton and $Q_1$ is aryl substituted with an anionic group (such as, for example, a carboxylate, sulfonate, phosphonate, phosphate ester or phosphinate), an alkyl group substituted with an anionic group (such as, for example, a carboxylate, sulfonate, phosphonate, phosphate ester or phosphinate) or an aralkyl group substituted with an anionic group (such as, for example, a carboxylate, sulfonate, phosphonate, phosphate ester or phosphinate); where at least one of A or A' is an alkyl group substituted with an anionic group (e.g., an amino acid, especially glycine, serine or aspartic acid). Amino phosphinic acids and phosphate esters are preferred. In an example, $Q_1$ is aralkyl and the alkyl portion of said aralkyl group is methyl ($C_1$).

Statement 9. A macrocyclic complex according to any one of the preceding Statements, where the macrocyclic complex comprises:
a TACN moiety comprising two pendents chosen from:

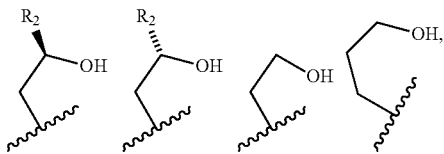

deprotonated analogs thereof, substituted analogs thereof, and combinations thereof;
a TACN moiety comprising chosen from two

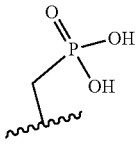

pendents deprotonated analogs thereof, substituted analogs thereof, and combinations thereof.

Statement 10. A macrocyclic complex according to any one of the preceding Statements 1, where the TACN moiety has one of the following structures:

Scheme I

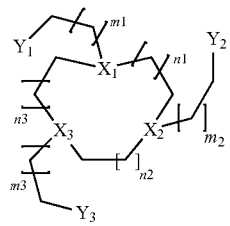

A

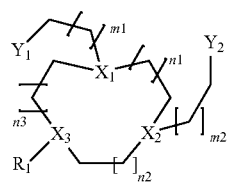

B

-continued

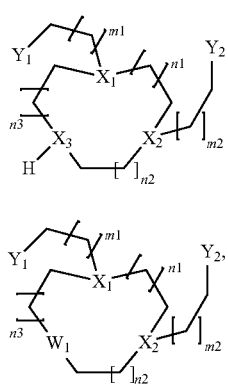

where $X_1$, $X_2$, $X_3$, are N; $W_1$ is O or S; $Y_1$, $Y_2$, $Y_3$ are each independently
i) pendent donors comprising O, where O has at least one lone pair of electrons but preferably two or three lone pairs (e.g., ketone, alcohol, alkoxide, phenol or phenoxide, sulfonic acid, phosphinic acid or phosphonic acid or a deprotonated form of the foregoing, such as an oxide, including an alkoxide or a phenoxide); or
ii) pendent donors comprising N, where N has a least one lone pair of electrons such as triazole; $m_1$, $m_2$ and $m_3$ are each independently 1, 2 or 3; $n_1$, $n_2$, and $n_3$ are each independently 1 or 2 or 3; and $R_1$ is a substituted or unsubstituted aryl, a substituted or unsubstituted heterocyclic group or substituted or unsubstituted alkyl, and where the alkyl segment of the alkyl-Y chain (alkyl-$Y_1$, alkyl-$Y_2$, and/or alkyl-$Y_3$) may each independently be substituted or unsubstituted.

Statement 11. A macrocyclic complex according to any one of the preceding Statements, where the TACN moiety or O-substituted TACN moiety has the following structure:

Scheme II

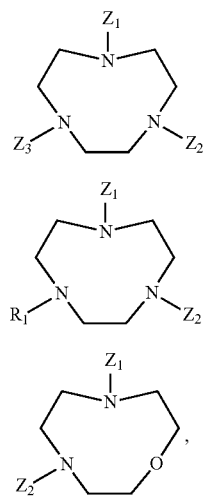

where $R_1$ is a substituted or unsubstituted aryl, substituted or unsubstituted heteroaryl or a substituted or unsubstituted alkyl and $Z_1$, $Z_2$, $Z_3$ are independently an anionic pendent.

Statement 12. A macrocyclic complex according to Statement 11, where: when the macrocycle has Structure I, $Z_1$ is H or one of the pendent groups in Scheme III and $Z_2$ and $Z_3$ each independently are one of the pendent groups in Scheme III; and/or when the macrocycle has Structure II or III, $Z_1$ and $Z_2$ each independently are one of the pendent groups in Scheme III; and/or for all Structures I-III, each of $Z_1$, $Z_2$, $Z_3$, as applicable, are independently selected.

Statement 13. A macrocyclic complex according to any one of the preceding Statements, where the TACN moiety has one of the following structures:

Scheme VI

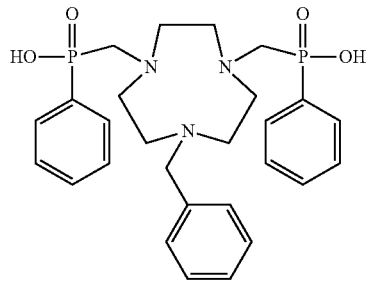

PhOTO

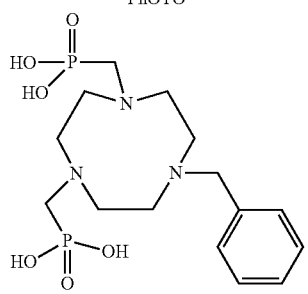

TOPA

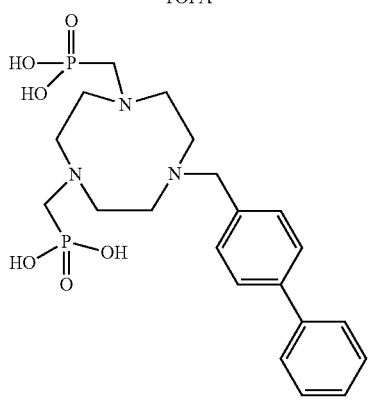

TOBP

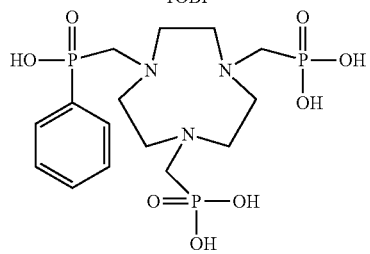

NOTPP

-continued
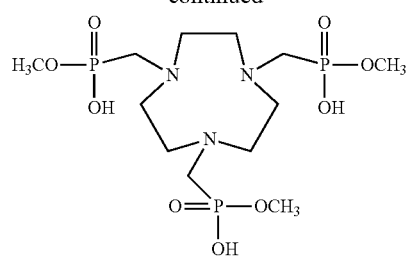
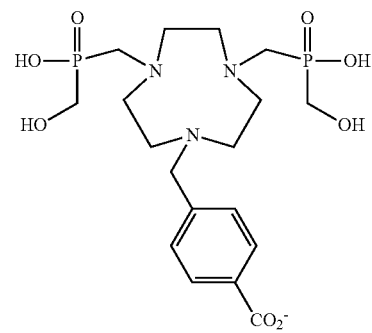
DRAP-OH
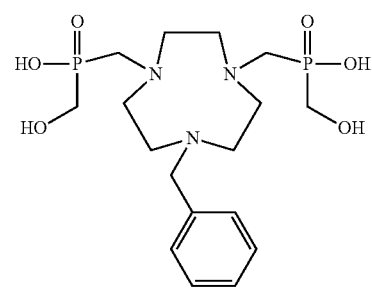
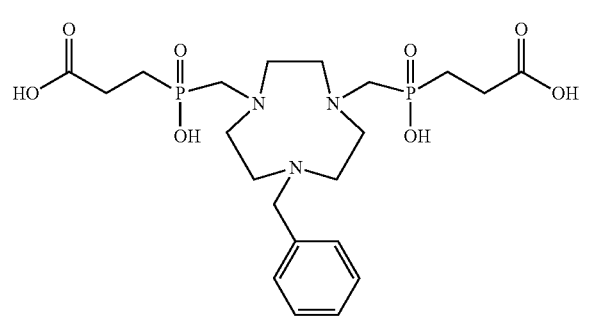
TRAP-POP
-continued
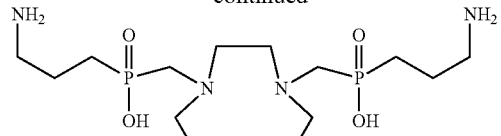
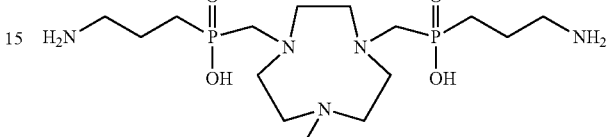
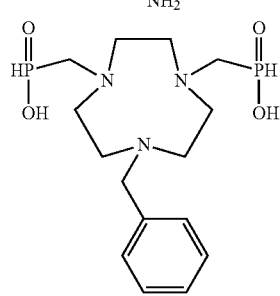
DRAP-H
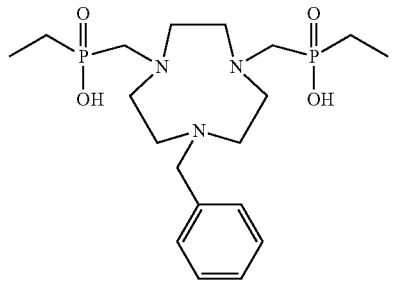
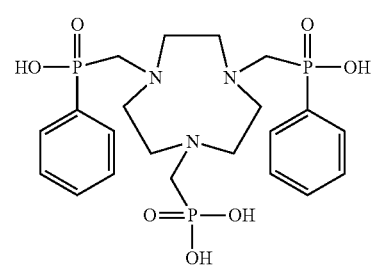
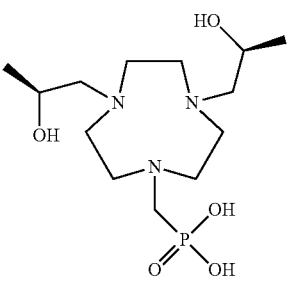
DAPO Scheme VII
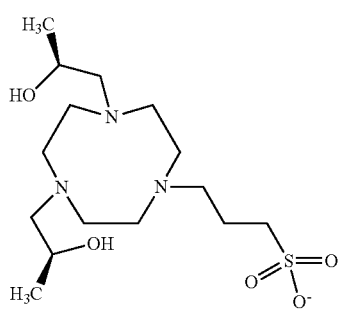
TASO
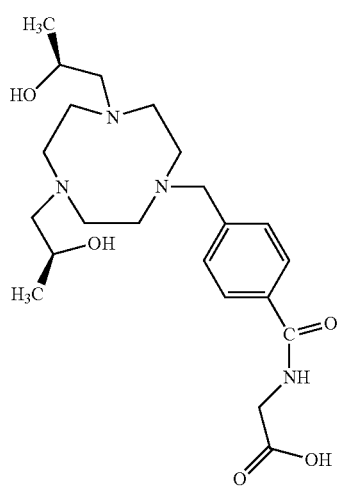
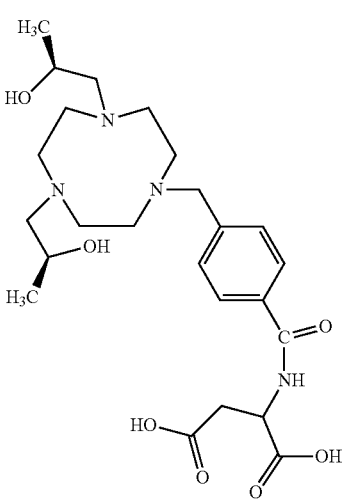
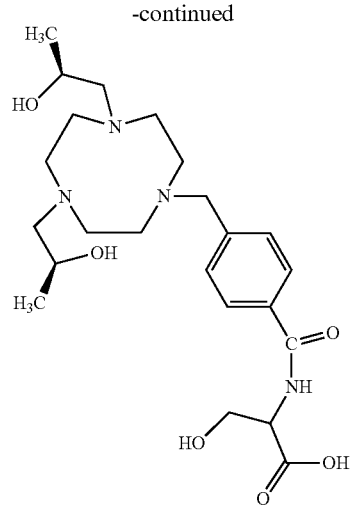
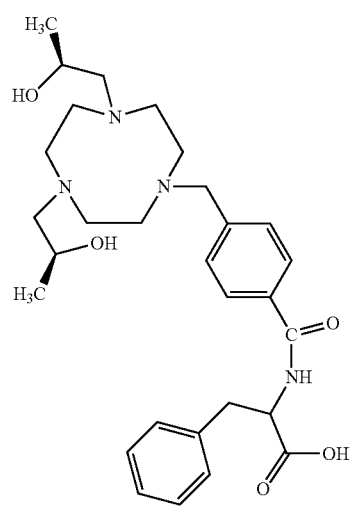
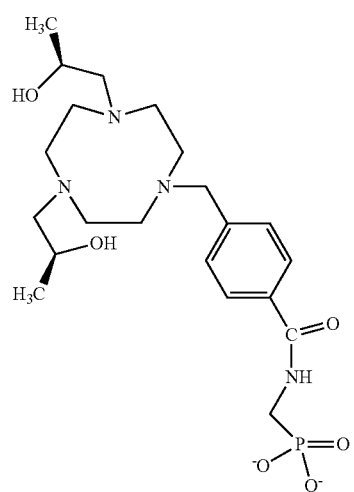

41
-continued
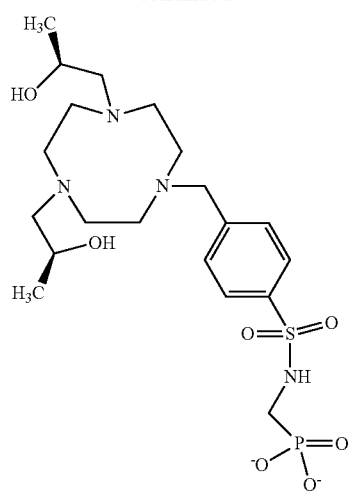
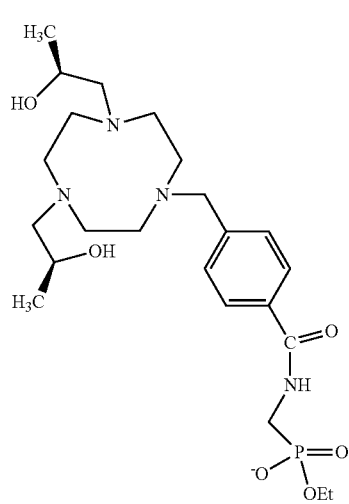
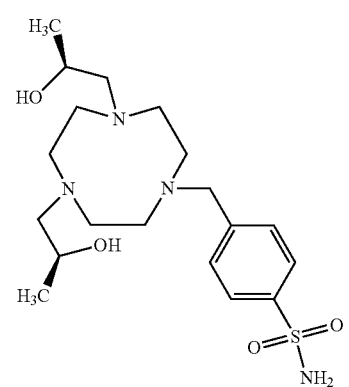
42
-continued
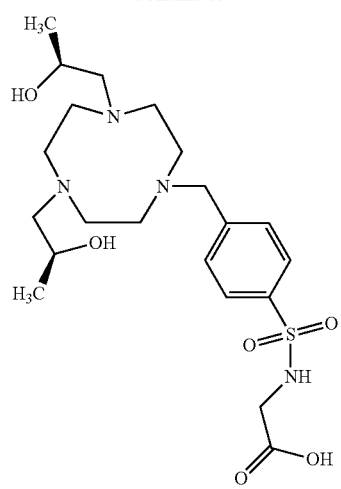
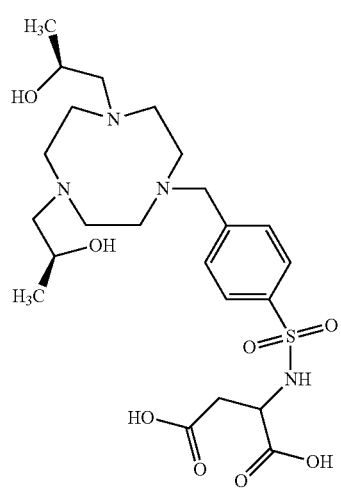
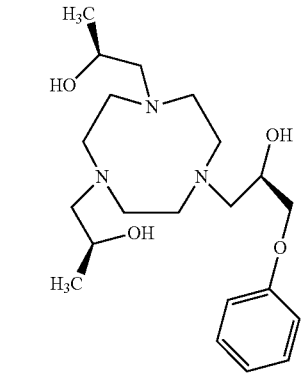

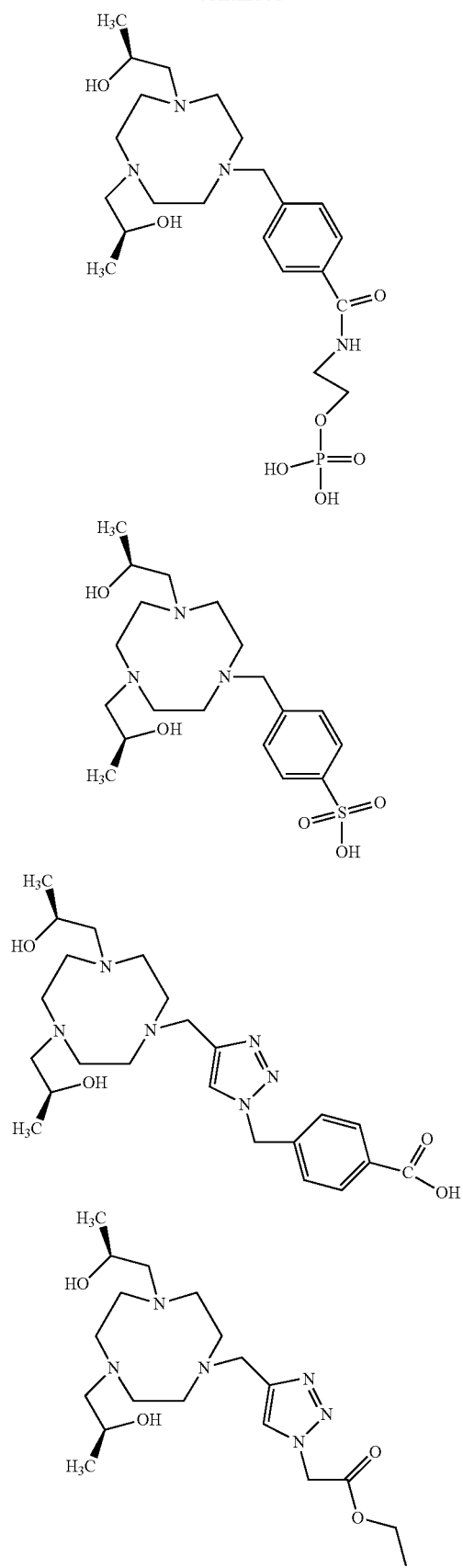
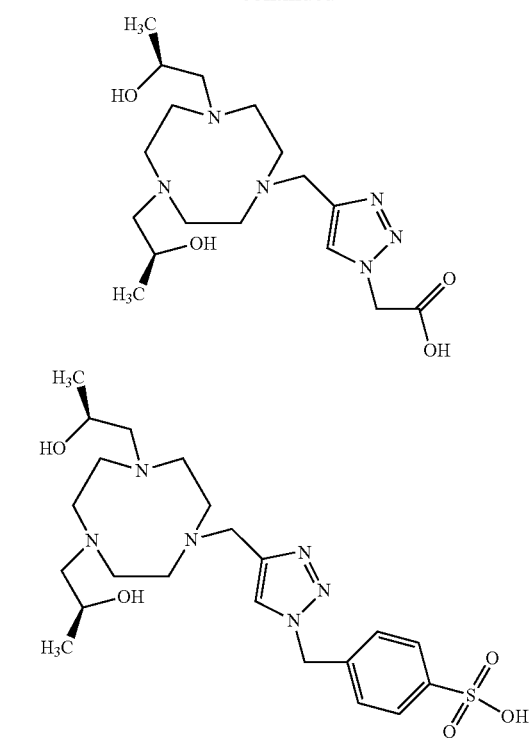
Statement 14. A macrocyclic complex according to any one of Statements 1-13, where the macrocyclic complex has one of the following structures:
Scheme VIII
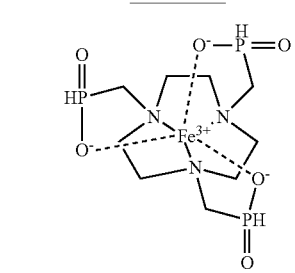
Fe(TRAP-H)
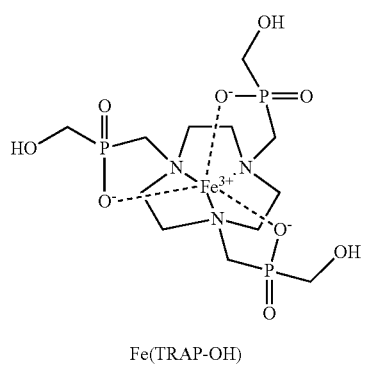
Fe(TRAP-OH)

-continued
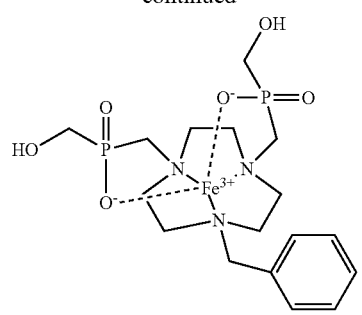
Fe(DRAP-OH)
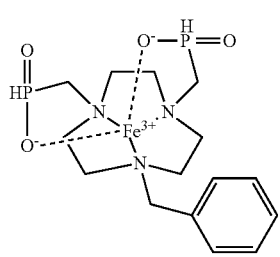
Fe(DRAP-H)
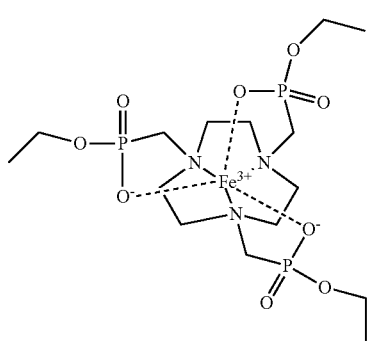
Fe(NOTPMe)
Scheme IX
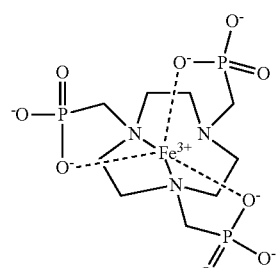
Fe(NOTP)
-continued
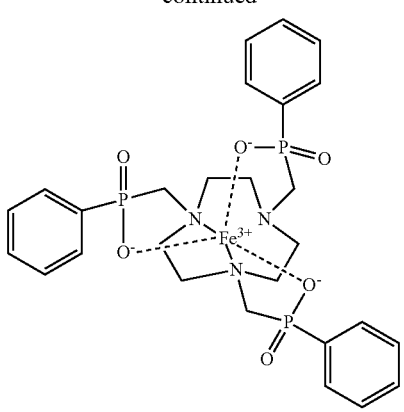
Fe(TRAP-Ph)
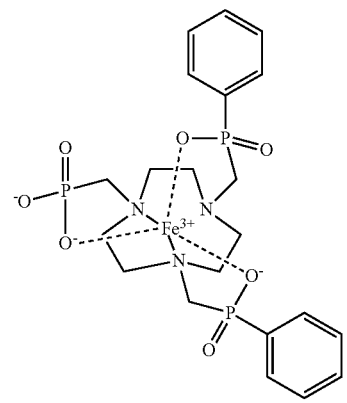
Fe(TRAP-POP)
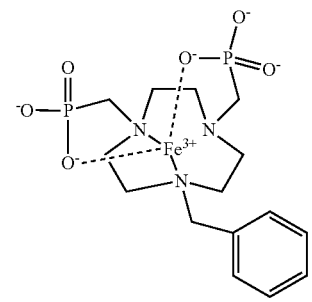
Fe(TOPA)
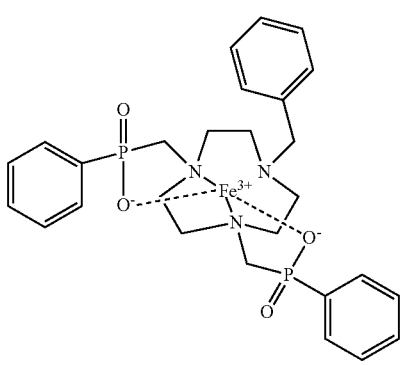
Fe(PHOTO)

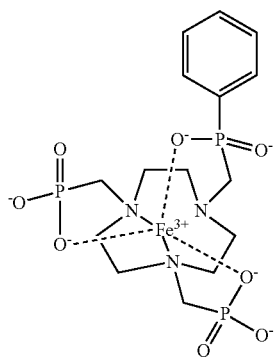

Fe(TRAP-OPO)

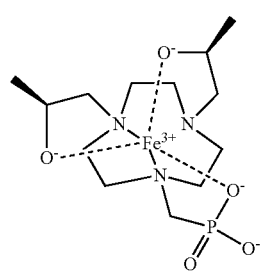

Fe(DAPO)

SCHEME XI

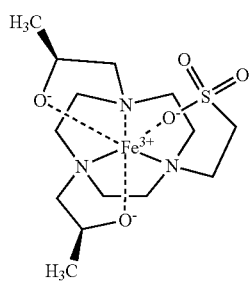

Fe(TASO)

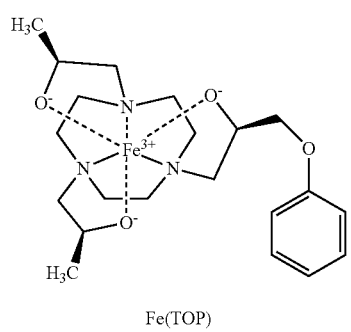

Fe(TOP)

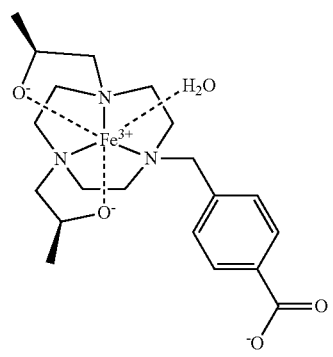

Fe(TOBA)

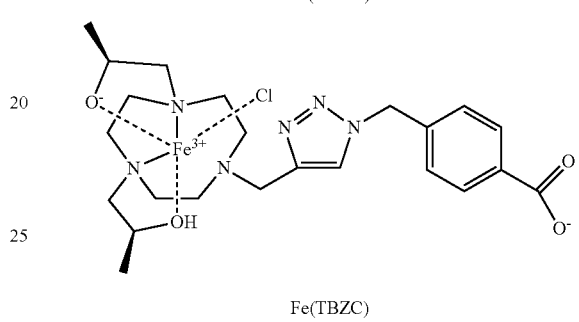

Fe(TBZC)

Statement 15. A compound or polymer comprising one or more macrocyclic complex groups covalently bound to a linker group or a polymer, a dendrimer, a protein, or a peptide comprising one or more pendent macrocyclic complex groups covalently bound to the polymer, the dendrimer, the protein, or the peptide, where each of the individual macrocyclic complex groups are derived from a macrocyclic complex of any one of Statements 1-14.

Statement 16. A compound or polymer according to Statement 15, where the compound comprises the following structure:

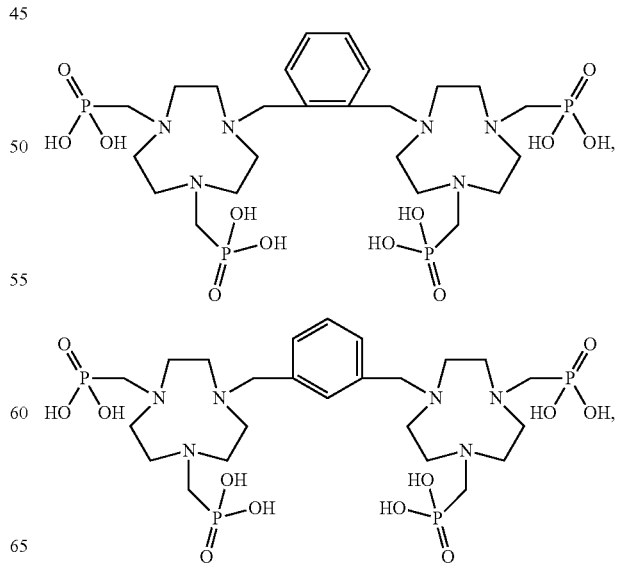

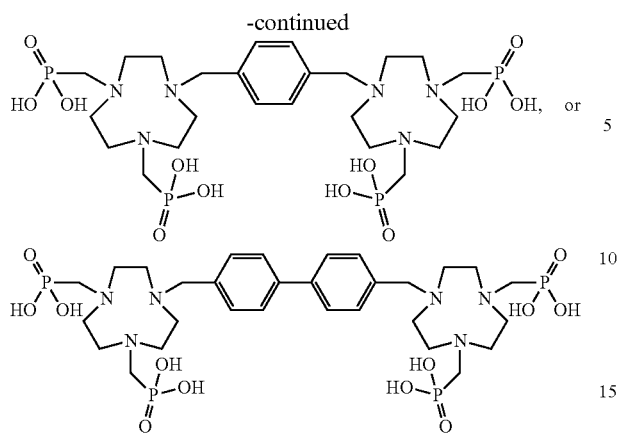

Statement 17. A compound or polymer according to Statement 15, where the compound has the following structure:

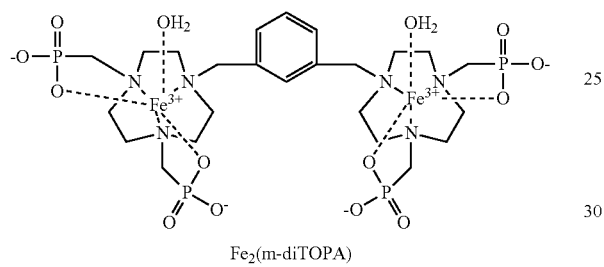

Fe$_2$(m-diTOPA)

Statement 18. A composition comprising one or more macrocyclic compound of any one of Statements 1-14 and/or one or more compound or polymer of any one of Statements 15-17 and a pharmaceutically acceptable carrier.

Statement 19. A composition according to Statement 18, where the composition further comprises human serum albumin and/or meglumine.

Statement 20. A method to obtain an image of at least a portion of a cell, organ, vasculature or tissue comprising:

contacting the cell, organ, vasculature, or tissue (or a portion thereof) with one or more macrocyclic compound of any one of Statements 1-14 and/or one or more compound of any one of Statements 15-17 and/or one or more composition of any one of Statements 18-19 and/or Fe(NOTP) and/or Fe(TRAP-Ph), and imaging at least a portion of the cell, organ, vasculature, or tissue to obtain an image of the portion of a cell, organ, vasculature, or tissue, where the image is obtained by using magnetic resonance.

Statement 21. A method according to Statement 20, where the cell, organ, vasculature, or tissue is part of an individual.

Statement 22. A method according to Statement 20 or 21, where the image is obtained using magnetic resonance imaging (MRI).

Statement 23. A method according to any one of Statements 20-22, where the macrocyclic compound(s) and/or compound(s) is/are a T$_1$ agent or T$_1$ agents.

Statement 24. A macrocycle compound comprising:

a 1,4,7-triazacyclononane (TACN) moiety or an O-substituted TACN moiety; and one or more anionic pendent groups that are substituents on the TACN moiety independently chosen from:

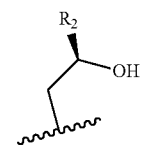
1

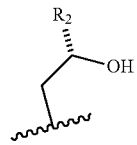
1B

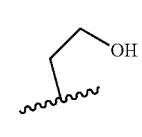
2

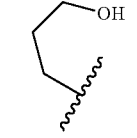
3

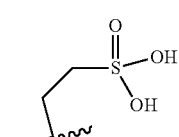
4

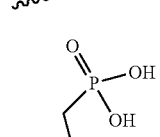
5

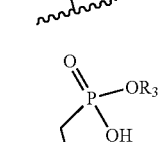
6

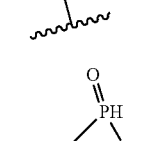
7

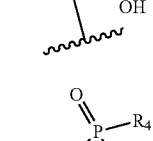
8

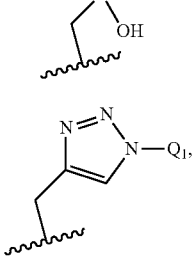
9 substituted analogs thereof, deprotonated analogs thereof, stereoisomers thereof, and combinations thereof, where R$_2$ is a substituted or unsubstituted alkyl group, a substituted or unsubstituted aromatic group, which may be an aryl group, or a substituted ether; R$_3$ is a substituted or unsubstituted alkyl or a substituted or unsubstituted aryl group; $R_4$ is a substituted alkyl (e.g., substituted with a hydroxyl or a carboxylate group, or the like) or unsubstituted alkyl or a substituted or unsubstituted aryl group; and $Q_1$ is aryl substituted with an anionic group (such as, for example, a carboxylate, sulfonate, phosphonate, phosphate ester or phosphinate), an alkyl group substituted with an anionic group (such as, for example, a carboxylate, sulfonate, phosphonate, phosphate ester or phosphinate) or an aralkyl group substituted with an anionic group (such as, for example, a carboxylate, sulfonate, phosphonate, phosphate ester or phosphinate);

or a salt, a partial salt, a hydrate, a polymorph, or a stereoisomer thereof.

Statement 25. A macrocycle compound according to Statement 24, where: when the macrocycle compound has Structure (I) of Scheme II and $Z_1$ and $Z_2$ are Structure 6 of Scheme III where $R_3$ is an unsubstituted ethyl, $Z_3$ is not Structure 6 of Scheme III where $R_3$ is an unsubstituted ethyl group, and/or when the macrocycle compound has Structure (I) of Scheme II and $Z_1$ and $Z_2$ are Structure 6 of Scheme III where $R_3$ is an unsubstituted or substituted ethyl, $Z_3$ is not Structure 6 of Scheme III where $R_3$ is an unsubstituted or substituted ethyl group; and/or when the macrocycle has Structure (I) of Scheme II and $Z_1$ and $Z_2$ are Structure 6 of Scheme III where $R_3$ is an unsubstituted alkyl, $Z_3$ is not Structure 6 of Scheme III where $R_3$ is an unsubstituted alkyl; and/or when the macrocycle has Structure (I) of Scheme II and $Z_1$ and $Z_2$ are Structure 6 of Scheme III where $R_3$ is an unsubstituted or substituted alkyl, $Z_3$ is not Structure 6 of Scheme III where $R_3$ is an unsubstituted or substituted alkyl; and/or when the macrocycle has Structure (I) of Scheme II and $Z_1$ and $Z_2$ are Structure 7 of Scheme III, $Z_3$ is not Structure 7 of Scheme III; and/or when the macrocycle has Structure (I) of Scheme II and $Z_1$ and $Z_2$ are Structure 8 of Scheme III where $R_3$ is alkyl having a terminal hydroxyl substitution, $Z_3$ is not Structure 8 of Scheme III where $R_3$ is not alkyl having a terminal hydroxyl substitution; and/or when the macrocycle has Structure (I) of Scheme II and $Z_1$ and $Z_2$ are Structure 8 of Scheme III where $R_3$ is a substituted alkyl, $Z_3$ is not Structure 8 of Scheme III where $R_3$ is a substituted alkyl; and/or when the macrocycle has Structure (II) of Scheme II and $Z_1$ and $Z_2$ are Structure 8 of Scheme III where $R_4$ is alkyl having a terminal hydroxyl substitution, $R_1$ is not alkyl having a terminal aryl group; and/or when the macrocycle has Structure (II) of Scheme II and $Z_1$ and $Z_2$ are Structure 8 of Scheme III where $R_4$ is alkyl having a terminal hydroxyl substitution, $R_1$ is not substituted alkyl.

Statement 26. A macrocycle compound according to Statement 24 or 25, where at least one or all of the one or more pendent groups is covalently bound to a N on the TACN moiety.

Statement 27. A macrocycle compound according to any one of Statements 24-26, where at least one of the pendent groups is substituted at a benzylic position or any carbon the alkyl group leading to the heteroatom of the pendent group.

Statement 28. A macrocycle compound according to any one of Statements 24-27, where the macrocycle further comprises one or more ancillary group(s) (e.g., one or more coordinating pendent group(s), one or more non-coordinating pendent group(s), or a combination thereof).

Statement 29. A macrocycle compound according to Statement 28,

Scheme V

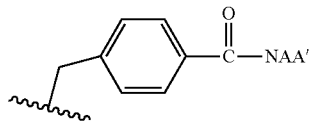

i

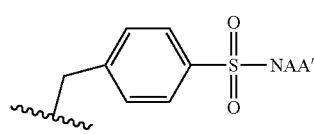

ii

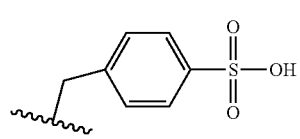

iii

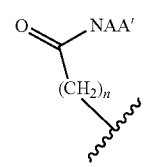

iv

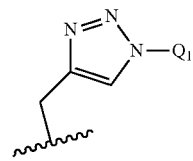

v where A and A' are each independently a substituted or unsubstituted $C_1$ to $C_{12}$ alkyl group of linear or branched structure or a proton and $Q_1$ is aryl substituted with an anionic group (such as, for example, a carboxylate, sulfonate, phosphonate, phosphate ester or phosphinate), an alkyl group substituted with an anionic group (such as, for example, a carboxylate, sulfonate, phosphonate, phosphate ester or phosphinate) or an aralkyl group substituted with an anionic group (such as, for example, a carboxylate, sulfonate, phosphonate, phosphate ester or phosphinate); where at least one of A or A' is an alkyl group substituted with an anionic group (e.g., an amino acid, especially glycine, serine or aspartic acid). Amino phosphinic acids and phosphate esters are preferred. In one embodiment, $Q_1$ is aralkyl and the alkyl portion of said aralkyl group is methyl ($C_1$).

Statement 30. A macrocycle compound according to any one of Statements 24-29, where the macrocycle has one of the following structures:

Scheme I

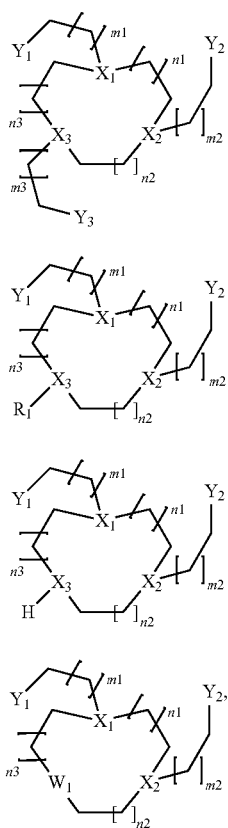

where $X_1$, $X_2$, $X_3$, are N; $W_1$ is or S; $Y_1$, $Y_2$, $Y_3$ are each independently
i) pendent donors comprising O, where O has at least one lone pair of electrons but preferably two or three lone pairs (e.g., ketone, alcohol, alkoxide, phenol or phenoxide, sulfonic acid, phosphinic acid or phosphonic acid or a deprotonated form of the foregoing, such as an oxide, including an alkoxide or a phenoxide); or
ii) pendent donors comprising N, where N has a least one lone pair of electrons such as triazole; $m_1$, $m_2$ and $m_3$ are each independently 1, 2 or 3; $n_1$, $n_2$, and $n_3$ are each independently 1 or 2 or 3; and $R_1$ is a substituted or unsubstituted aryl, a substituted or unsubstituted heterocyclic group or substituted or unsubstituted alkyl, and where the alkyl segment of the alkyl-Y chain (alkyl-$Y_1$, alkyl-$Y_2$, and/or alkyl-$Y_3$) may each independently be substituted or unsubstituted.

Statement 31. A macrocycle compound according to any one of Statements 24-30, where the macrocycle has the following structure:

Scheme II

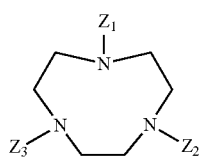
(I)

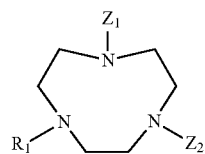
(II)

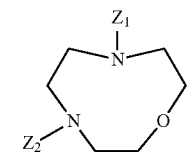
(III)

where $R_1$ is a substituted or unsubstituted aryl, substituted or unsubstituted heteroaryl or a substituted or unsubstituted alkyl, and $Z_1$, $Z_2$, $Z_3$ are independently and anionic pendent, where the macrocycle has Structure I, $Z_1$ is H or one of the pendent groups in Scheme III and $Z_2$ and $Z_3$ each independently are one of the pendent groups in Scheme III, or where the macrocycle has Structure II or III, $Z_1$ and $Z_2$ each independently are one of the pendent groups in Scheme III; and where for all Structures I-III, each of $Z_1$, $Z_2$, $Z_3$, as applicable, are independently selected.

Statement 32. A macrocycle compound according to any one of Statements 24-31, where the macrocycle has the following structures:

Scheme VI

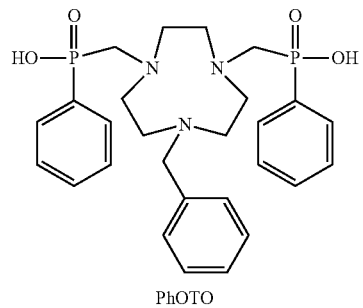

PhOTO

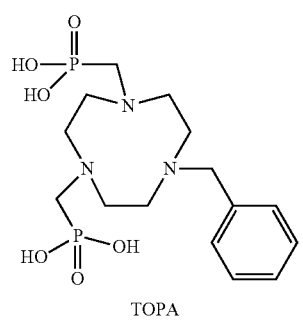

TOPA

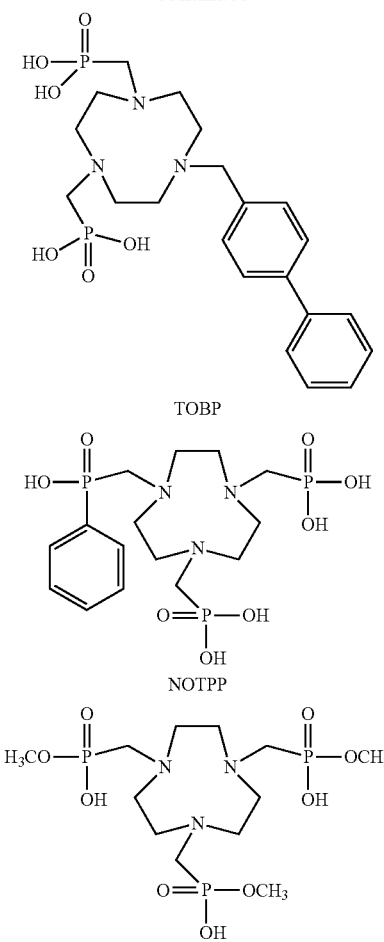
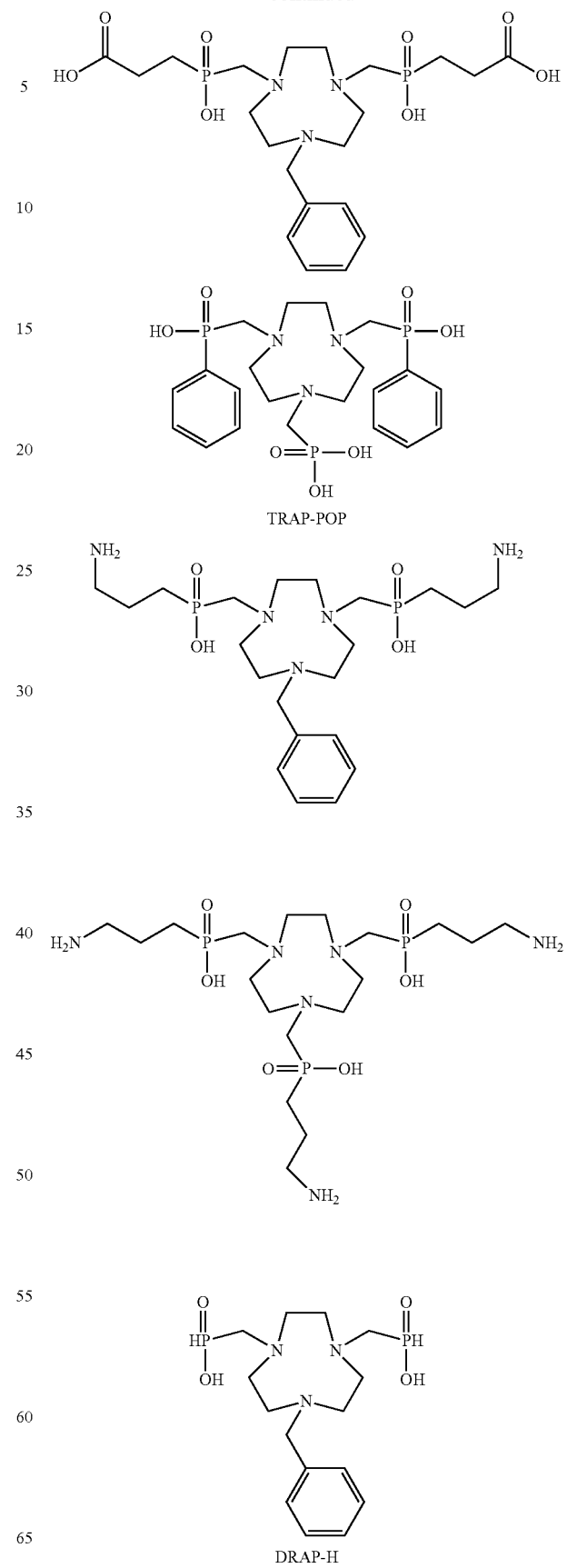

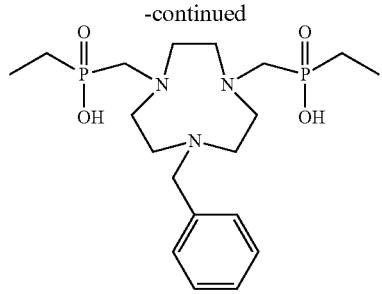
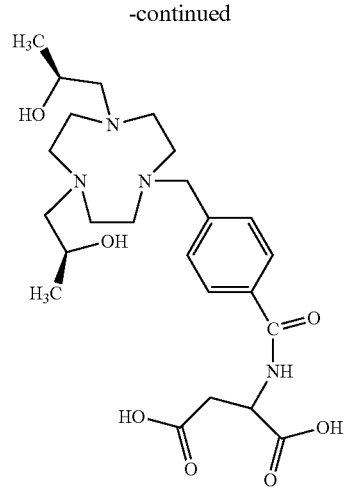
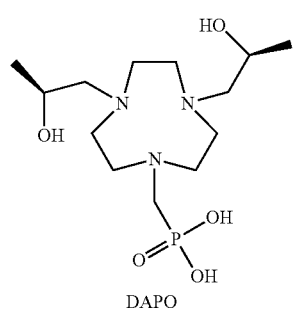
DAPO
Scheme VII
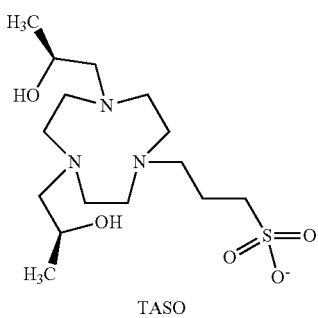
TASO
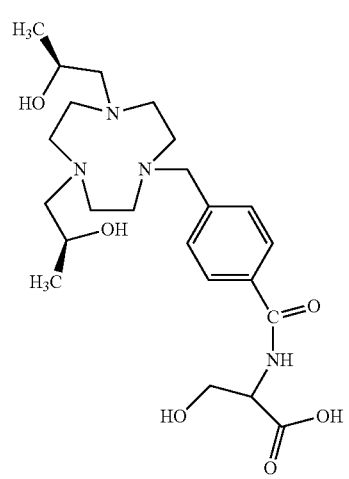
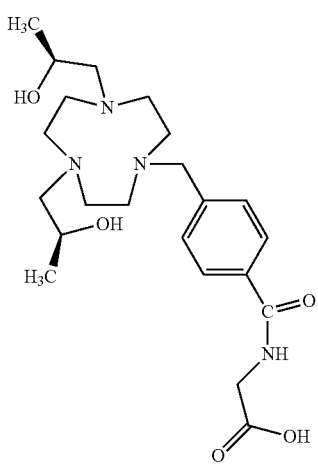
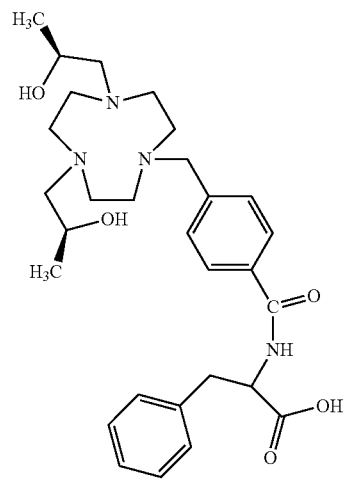

59
-continued
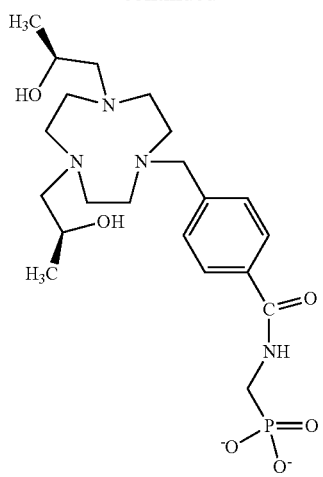
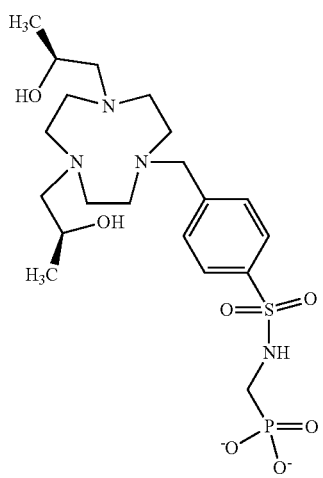
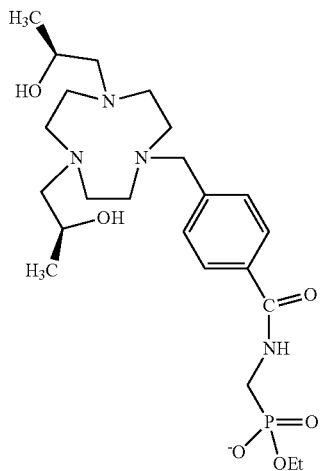
60
-continued
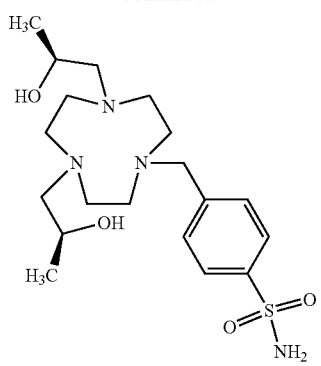
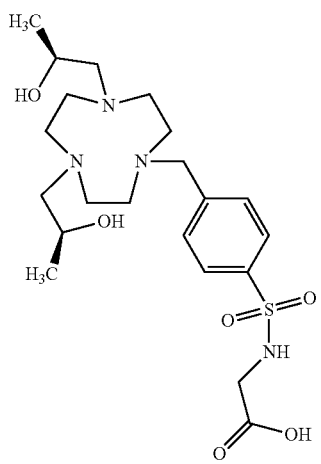
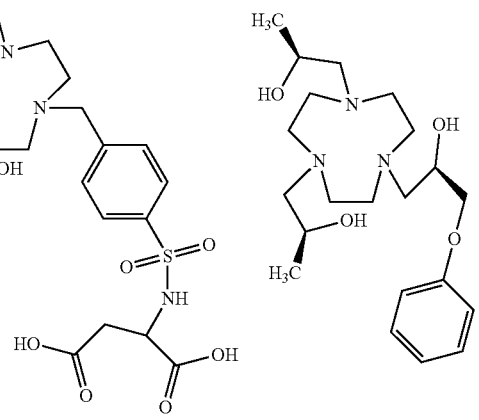

-continued

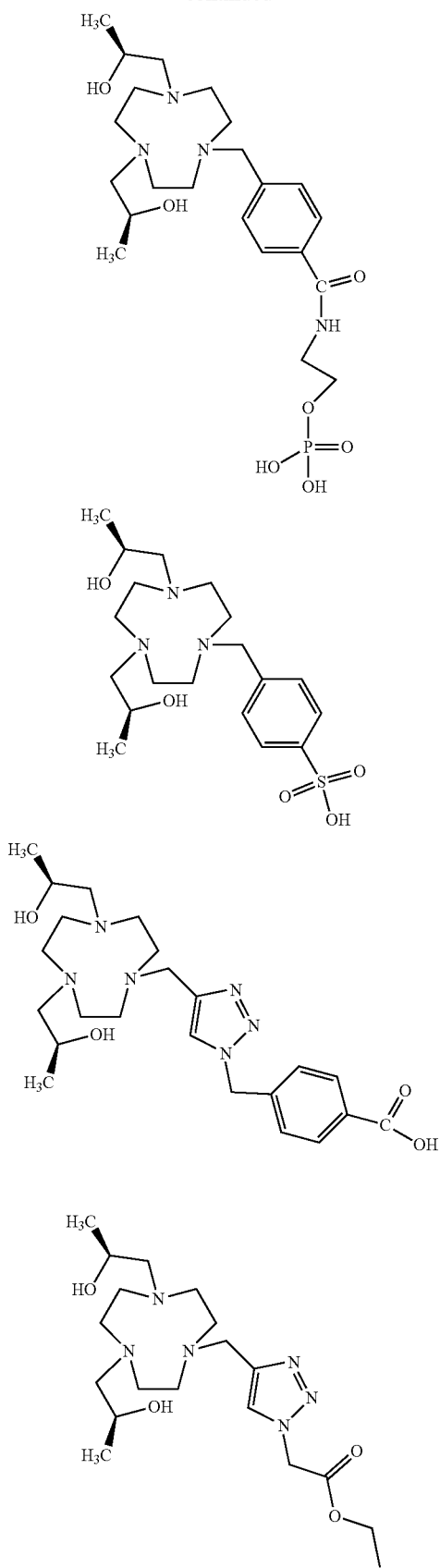 [SMILES: C[C@H](O)CN1CCN(Cc2ccc(C(=O)NCCOP(=O)(O)O)cc2)CCN(C[C@H](C)O)CC1 ; C[C@H](O)CN1CCN(Cc2ccc(S(=O)(=O)O)cc2)CCN(C[C@H](C)O)CC1 ; C[C@H](O)CN1CCN(Cc2cn(Cc3ccc(C(=O)O)cc3)nn2)CCN(C[C@H](C)O)CC1 ; CCOC(=O)Cn1cc(CN2CCN(C[C@H](C)O)CCN(C[C@H](C)O)CC2)nn1]

-continued

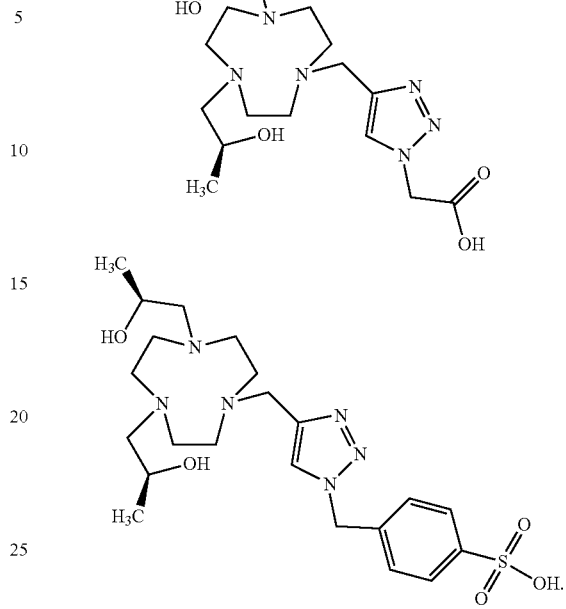

In this application, the use of the singular form encompasses the plural and visa versa.

The macrocyclic compounds of the present disclosure can be prepared, for example, as described in the Experimental Details. The following examples are presented to illustrate the present disclosure. They are not intended to be limiting in any manner. Those skilled in the art will recognize that routine modifications to these embodiments can be made which are intended to be within the scope of the present disclosure.

The steps of the method described in the various embodiments and examples disclosed herein are sufficient to carry out the methods of the present disclosure. Thus, in an embodiment, a method consists essentially of a combination of the steps of the methods disclosed herein. In another embodiment, a method consists of such steps.

EXPERIMENTAL DETAILS

Instrumentation. A Varian Inova 500 MHz NMR spectrometer equipped with FTS Systems TC-84 Kinetics Air Jet Temperature Controller was used to collect $^1$H NMR data. $^{13}$C NMR spectra were acquired using a Varian Mercury 300 MHz NMR spectrometer operating at 75 MHz. $^{17}$O NMR spectra were recorded on a Varian Inova 400 MHz spectrometer equipped with a 5 mm broad-band probe operating at a resonance frequency of 54.24 MHz. All pH measurements were obtained by using an Orion 8115BNUWP Ross Ultra Semi Micro pH electrode connected to a 702 SM Titrino pH. ThermoFinnigan LCQ Advantage IonTrap LC/MS equipped with a Surveyor HPLC system was used to collect mass spectral data. Absorbance spectra were collected using Beckman-Coulter DU 800 UV-vis Spectrophotometer equipped with a Peltier Temperature Controller. Samples were prepared in water with 1% $H_2^{17}O$. The chemical shifts as well as the line width at half-height of the symmetric water peak were determined in the absence and in the presence of metal complex at variable temperatures and pH 6. The line width at half-height of the signal in absence and in presence of metal complex at variable temperatures was used to calculate the transverse relaxation times using Swift-Connick equations (Eqs. 5-6). All fits are from the simultaneous least-squares fit of the measured data.

TASO. To a 25 mL round bottom flask with gas inlet and stir bar was added 0.100 g TACN (1,4,7-triazacyclononane) (0.774 mmol) in 4 mL toluene 1 mL chloroform solution. 0.0920 g N,N-dimethylformamide dimethylacetal (0.774 mmol) was added to the flask. The solution was stirred for 24 hours at room temperature. ESI-MS (m/z) of 1,4,7-triazatricyclo[5.2.1.04,10]decane (TACN-orthoamide), calculated: 140.1 [M+H+] (100%). The solution was dried by placing flask on a rotoevaporator. The dried TACN-orthoamide and 15 mL dry tetrahydrofuran (THF) was added in 50 mL 3-necked round bottom flask equipped with a magnetic stir bar, reflux condenser, gas inlet tube and addition funnel. 92.2 µL benzyl bromide (0.774 mmol) was added into the flask and the solution was stirred overnight at room temperature. A white-beige color precipitate was collected by suction filtration method and washed with dry THF (10 mL) and diethyl ether (10 mL). 7 mL methanol and 7 mL 12 M HCl was added to the precipitate in the flask for the deprotection process. The solution was heated to reflux for 4 hours. After the solution was cooled to room temperature, NaOH pellets were added to bring the pH of the solution to 8. Then the solution was filtered to remove NaCl salt precipitate and extracted with chloroform (3×60 mL). ESI-MS (m/z), calculated: 220.3 [M+H+] (100%). The solution was subjected to rotoevaporation and dissolved in 15 mL ethanol in a 25 mL round bottom flask with 0.225 g S-propylene oxide (3.870 mmol) and stirred for 24 hours at room temperature. The solution was rotoevaporated and dried on a Schlenk line under vacuum and dissolved in 10 mL methanol. % ESI-MS (m/z), calculated: 336.3 [M+H+] (100%). Benzyl deprotection was performed by Pd/C (10%) catalyst. 30 mg Pd/C (10%) in 5 mL methanol and 1 mL water was added into the ligand solution. The air was removed from the solution under argon gas for 30 minutes. Catalytic hydrogenation was performed for 3 days with vigorously stirring at room temperature under hydrogen atmosphere. The mixture was filtrated over celite to remove the catalyst from the reaction solution and (1,4,7-triazonane-1,4-diyl)bis(propan-2-ol) (DACO ligand) was obtained. ESI-MS (m/z), calculated: 246.3 [M+H+] (100%). The solution was dried by placing flask on a rotoevaporator. DACO ligand was dissolved in 15 mL acetonitrile in the 25 mL round bottom flask. 1 equivalent 1,3 propanesultone in 3 mL acetonitrile and N, N-Diisopropylethylamine (DIEA) were added to the flask. The solution was stirred for 3 days at reflux. The solution was rotoevaporated and dried on a Schlenk line under vacuum. Purification process was applied by basic alumina column with MeOH/DCM solvents. The yield was calculated as 37%. ESI-MS (m/z) (0.1% formic acid method), calculated: 368.3 [M+H+] (100%) and 390.3 [M+Na+] (27%).

Fe(TASO) (see, e.g., FIG. 1). To a 25 mL round bottom flask with a stir bar was added TASO ligand (0.0589 g, 0.160 mmol) and 8 mL ethanol. Then FeCl2.4H2O (0.0318 g, 0.160 mmol) was dissolved in 2 mL ethanol and added into the flask. The solution was stirred at room temperature for 2 days. A yellow precipitate was obtained. The precipitation was obtained by centrifuge and washed with diethyl ether for 3 times. The yellow powder was obtained by removing the solvent through rotoevaporation. ESI-MS (m/z), calculated: 421.1 [M+H$^+$] (100%) and 443.2 [M+Na$^+$] (55%). Here M is Fe(TASO) in neutral form. Magnetic susceptibility of Fe(TASO) is 5.67 µeff in aqueous solution as measured by using Evans' method.

Figure 4:
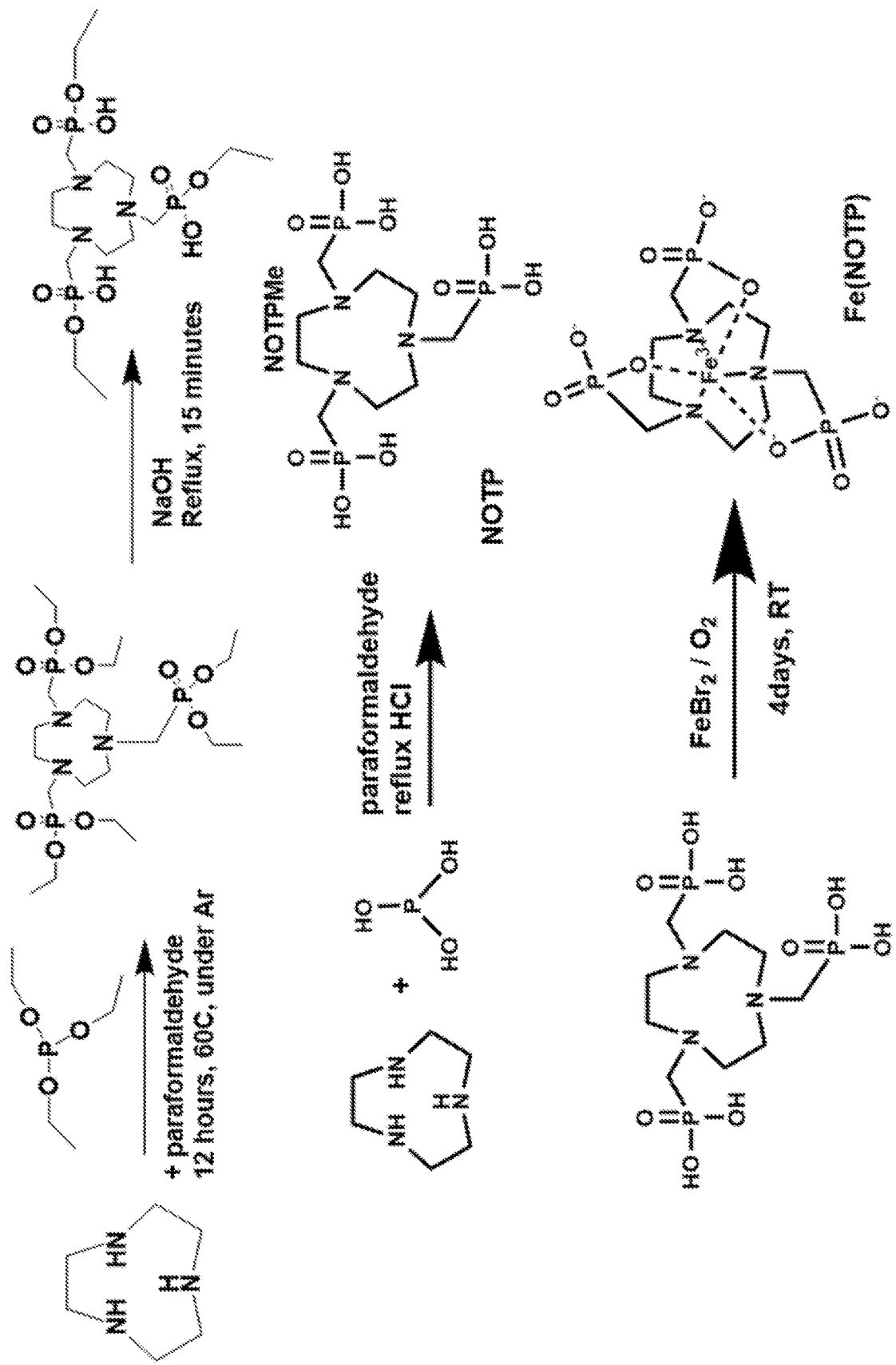
FIG. 4 shows the synthesis of macrocycle compounds with phosphinic acid pendents or phosphonic acid pendents and corresponding Fe(III) complexes.

NOTPMe. (see, e.g., FIG. 4). 1,4,7-triazacyclononane (3.1 mmol) was added to a two neck flask. Paraformaldehyde (15.4 mmol, 5 equivalents) and triethyl phosphite (31 mmol, 10 equivalents) were added under an argon atmosphere. The reaction was allowed to stir for 12 hours at 60° C. Excess reactants were removed under reduced pressure. 0.50 g of the resulting material (hexaethyl ((1,4,7-triazonane-1,4,7-triyl)tris(methylene))tris(phosphonate)), was weighed into a flask containing 2.5 mL of H2O. A 1.25 g of sodium hydroxide pellets were added and the mixture was stirred until all the sodium hydroxide dissolved. Once dissolved, the mixture was refluxed for 15 minutes, after which the flask was removed from the apparatus, 3 mL of H2O was added immediately upon removal, and then allowed to cool to room temperature. After room temperature was reached, the flask was allowed to cool in ice for an additional 15 minutes, during which time crystals began to form. The solvent was removed and the crystals were then washed with water, and a 1:1 mixture of ethanol and ethyl ether. ESI-MS: 494 [M−H$^+$], 516 [M+Na$^+$]. Here M is the neutral ligand (NOTPMe).

Figure 3:
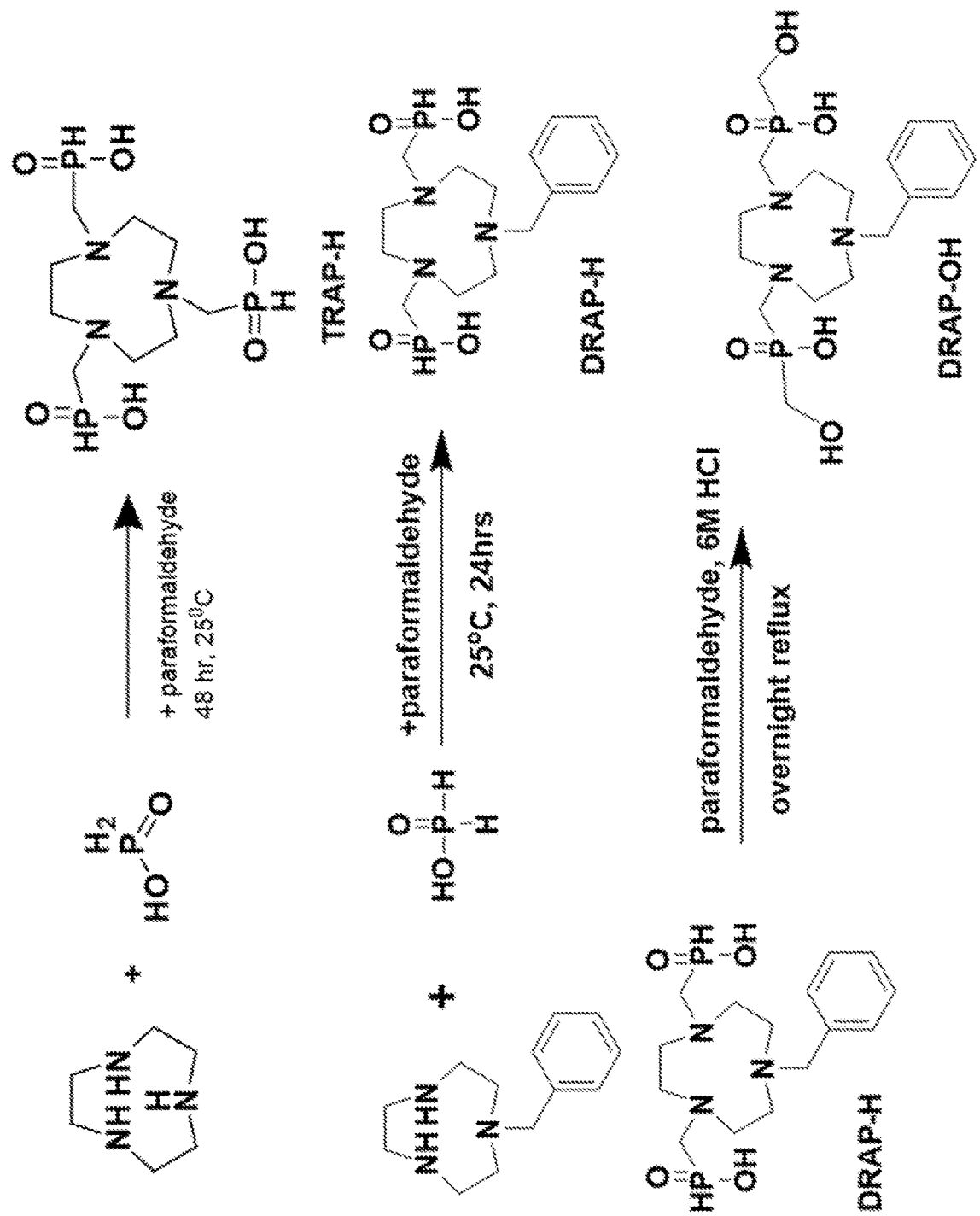
FIG. 3 shows the synthesis of macrocycle compounds with phosphinic acid pendents.

Trap-H synthesis (see, e.g., FIG. 3). Triazacyclononane (500 mg, 3.87 mmol) and paraformaldehyde (527 mg, 17.5 mmol) were dissolved with hypophosphorous acid (2.5 mL of 50% weight aq., 23.2 mmol) in water (18.75 mL), and stirred at room temperature for 48 hours. The reaction mixture was evaporated under vacuum with gentle heating to less than 40° C. The resulting oil was purified on a strong cationic exchanger, DOWEX 50 H+ form, with water elution. Fractions containing the pure ligand (confirmed by ESI mass spectrometry on LCQ) were combined, and the solvent was removed with gentle heating at less than 40° C. to give a clear oil (492 mg, 35%). MS (ESI, positive): m/z 364 [(TRAP-H)+H$^+$].

TRAP-Ph Synthesis (see, e.g., FIG. 2). 1,4,7-triazacyclononane (0.30 mmol) was added to a two necked flask which was attached to a reflux apparatus under Argon atmosphere. Dimethyl phenylphosphonite (1.35 mmol, 4.5 equivalents) and paraformaldehyde (1.8 mmol, 6 equivalents) were then added to the flask along with 15 mL of dry tetrahydrofuran. The solution was allowed to reflux for 16 hours. Excess solvent was then removed under reduced pressure. ESI-MS: 634[M+H$^+$].

The resulting TRAP-Ph-methoxy was then transferred to a double next flask, along with 4 mL of 50% w/v carbonate free sodium hydroxide. The flask was attached to a reflux apparatus and allowed to reflux for 30 minutes. 4 mL of distilled water was added, and the solution was allowed to reflux for an additional 30 minutes. After the second reflux, the reflux apparatus was removed and the solvent was allowed to evaporate until a two-layer system reformed. The flask was then taken off heat and allowed to cool to room temperature. The supernatant oil was removed and dissolved in ethanol. The ethanol was evaporated to leave TRAP-Ph. The resulting product was purified via recrystallization in methanol, followed by acetone, and then dichloromethane. ESI-MS: 590 [M+H$^+$]. Here M is TRAP-pH in neutral form.

Figure 2:
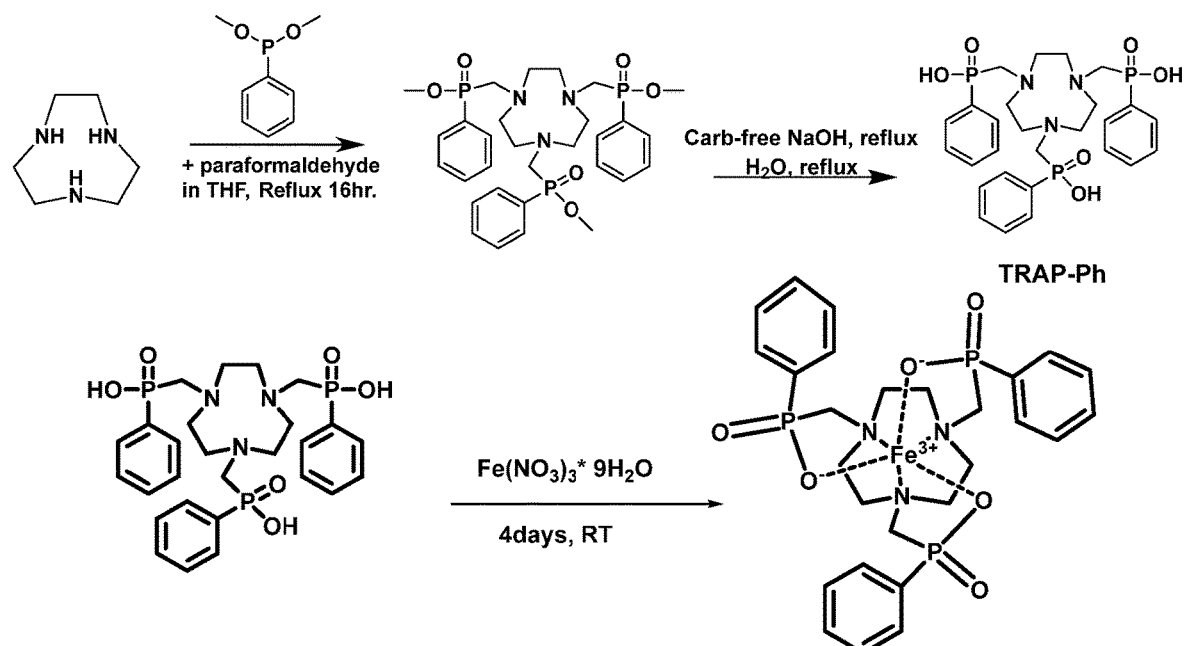
FIG. 2 shows schemes for the synthesis of TRAP-Ph macrocycle with phosphinic pendents and corresponding Fe(III) complex.

Fe(TRAP-Ph) (see, e.g., FIG. 2). TRAP-Ph was complexed with iron by mixing the TRAP-Ph with one equivalent of 0.01M iron (III) nitrate in methanol. The solution was allowed to stir for 4 days at room temperature. The methanol was then evaporated off to give the resulting product. ESI-MS: 645, 667 [M+Na$^+$].

1,4,7-triazacyclononane (0.15 mmol) was measured into a two-neck flask and set up on a reflux apparatus. Phosphorous acid (0.9 mmol, 6 equivalents) was additionally added to the flask along with 0.35 mL hydrochloric acid and 1.0 mL of distilled water. Once this solution was brought to reflux, paraformaldehyde (0.675 mmol, 4.5 equivalents) was added to the solution over the course of an hour. After the addition of paraformaldehyde was complete, the solution was allowed to reflux for an additional hour. The solution was cooled to room temperature and then added dropwise, slowly, to ethanol in an ice bath. After all the solution was added the mixture was stirred for an additional hour, after which the solid was collected and washed with ether and ethanol. This solid was recrystallized in small amounts of hot water to get pure NOTP as a white solid. ESI-MS in negative mode: 410.2 [M−H+]. Here M is neutral NOTP.

NOTP was complexed to iron by combining the NOTP with one equivalent of 0.01M aqueous Iron (II) Bromide. The solution was allowed to stir for 4 days at room temperature, after which the water was evaporated. ESI-MS (negative mode): 465 [M−H+]. Here M is Fe(NOTP) in neutral form.

Synthesis of DRAP-H (see, e.g., FIG. 3). 1-Benzyl-1,4,7-triazacyclononane dihydrobromide (1.0 g, 2.64 mmol) and paraformaldehyde (0.24 g, 7.92 mmol) were dissolved in a mixture of 50% aq $H_3PO_2$ (1.3 mL, 11.9 mmol) and water (5 mL). The reaction mixture was stirred for 24 hours at room temperature, then was co-evaporated three times with water and chromatographed on a strong cation exchanger (DOWEX50, H+-form). The column was washed with deionized water, then the NaCl gradient (5% by weight to 10% by weight) was increased to collect the fractions with benzyl TRAP-H (as monitored by MS). The eluate was evaporated to give a light brown oil. $^1$H NMR (300 MHz, $D_2O$): δ=3.02-3.52 (m, ring-$CH_2$, 12H and N—$CH_2$—P, 4H), 4.35 (s, N—$CH_2$-$C_6H_5$, 2H), 7.30-7.50 (m, —$C_6H_5$, 5H). MS (ESI, positive): m/z=376 [M+H$^+$]. Here M is the neutral ligand.

Synthesis of DRAP-OH (FIG. 3). DRAP-H was dissolved in 6 M HCl (20 mL). Paraformaldehyde (0.24 g, 7.92 mmol) was added, and the solution refluxed for 5 h (as monitored by MS), then evaporated to give crude benzyl DRAP-OH. MS (ESI, positive): m/z]=436 [M+H$^+$]. M is neutral ligand. Fe(NO$_3$)$_3$.9H$_2$O and benzyl DRAP-OH in a 1:1 ratio were dissolved in 10 mL deionized water, and stirred for 4 days (monitored by using MS). MS (ESI, positive): m/z=489 [M$^+$]. Here M is the neutral Fe(III) complex.

Figure 5:
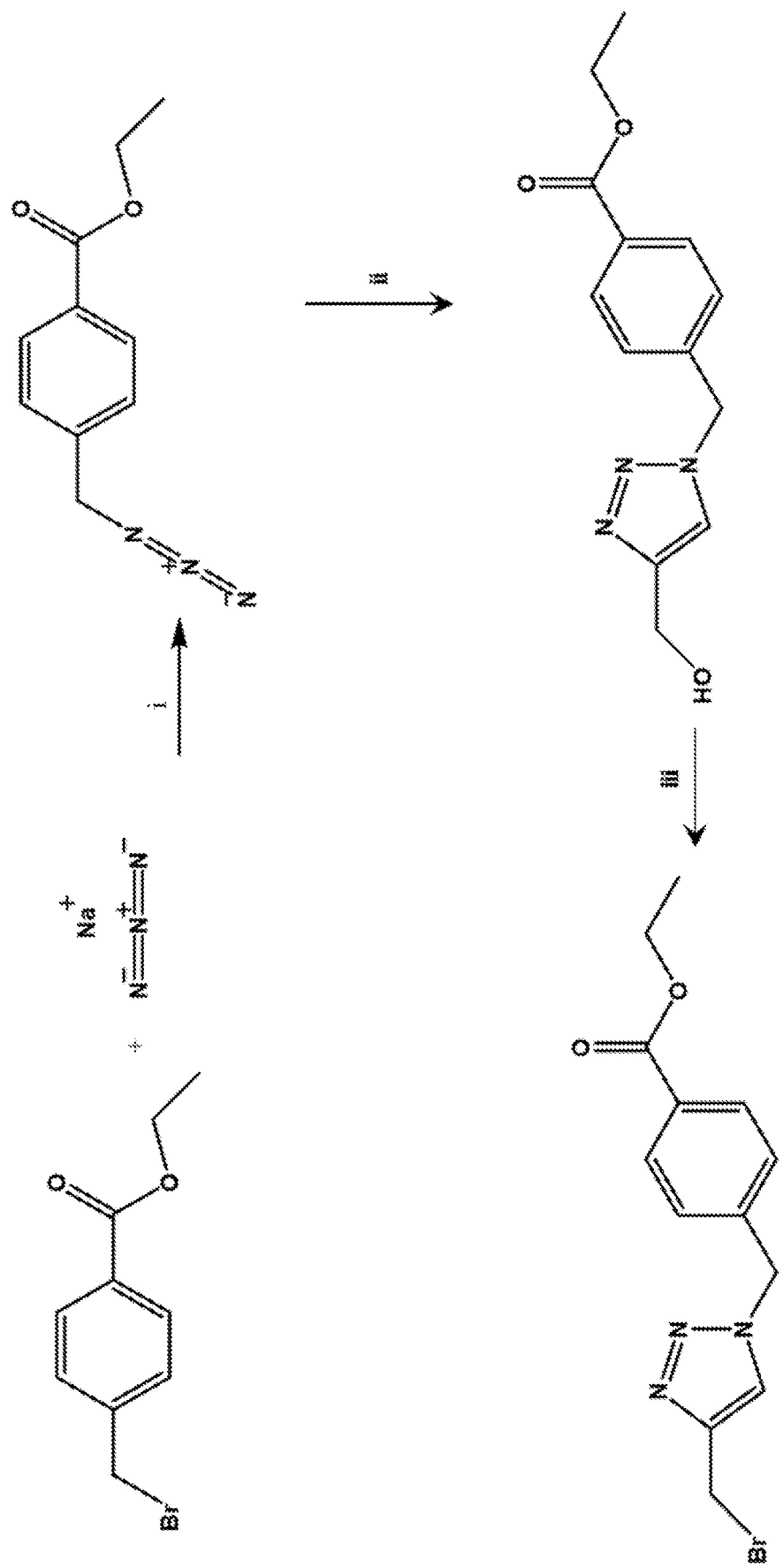
FIG. 5 shows schemes for the synthesis of triazole pendents with anionic groups including their attachment to a macrocycle and formation of Fe(III) complex.
Figure 5:
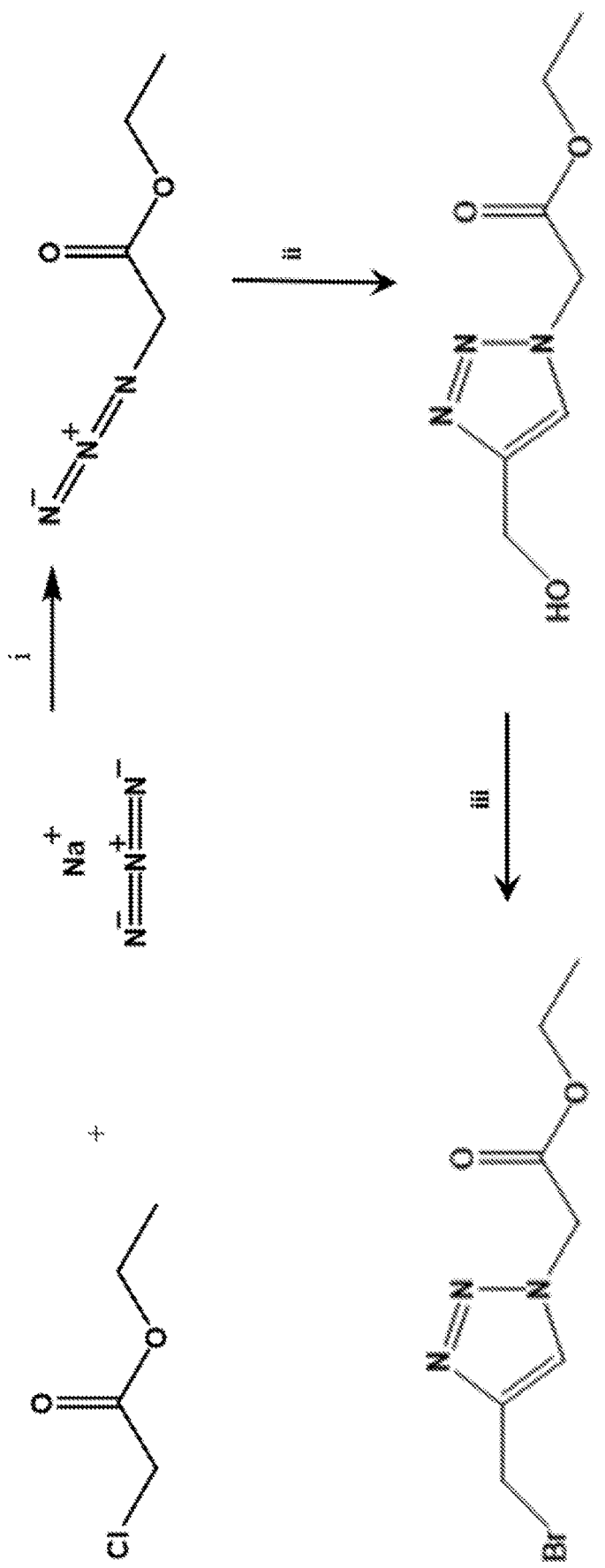
Figure 5:
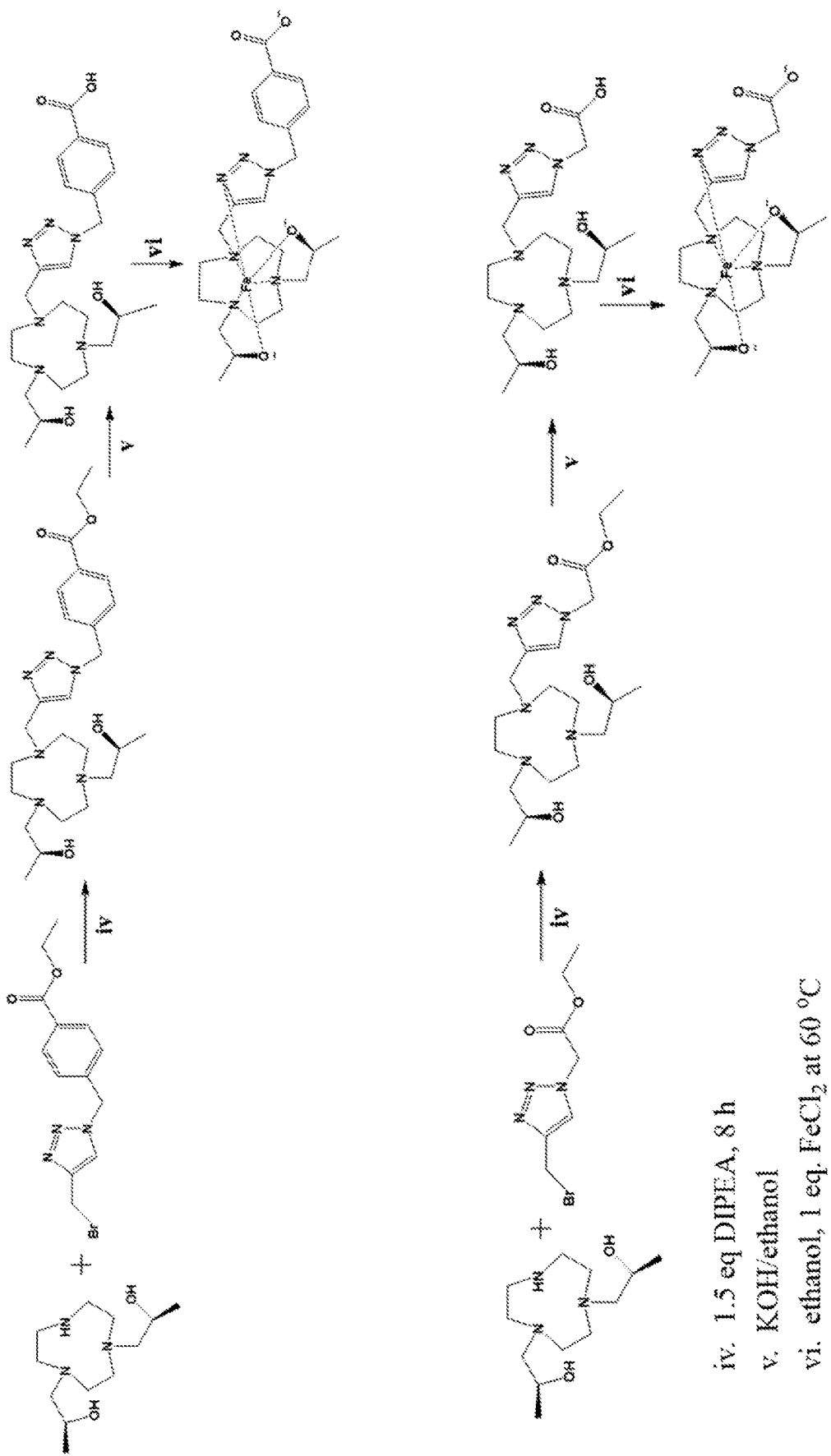

General procedure for "clicked" triazole pendents and their addition to macrocycle (see, e.g., FIG. 5). 2 equivalents of sodium azide were added to a solution of bromo/chloro reagent in methanol using an appropriate size round bottom flask. The solution was heated to 60° C. and stirred for 4 hours. The next reaction step was conducted without isolation or purification of the previous product. 1.1 equivalents of propargyl alcohol were added to the stirring solution from the previous reaction. In a separate flask, 0.1 equivalents of copper sulfate hexahydrate and 0.2 equivalents of sodium ascorbate in 2 mL of water were combined. The mixture was stirred for 1 min (min=min(s)), then added to the previous reaction flask. The reaction mixture was stirred at 60° C. for 8-12 hours or until completion (monitored by TLC). The reaction mixture was evaporated until dry, water added, and the product extracted with EtOAc (3×). Organic layers were combined and dried with anhydrous sodium sulfate. EtOAc was removed under vacuum to obtain crude product. Purification was carried out by recrystallization in EtOAc/DCM solution at 0° C. or on silica gel (25-50% EtOAc in Hexanes). ESI-MS (m/z): 262.3 (product 1), 186.2 (product 2). 3 equivalents was added of PBr$_3$ to a solution of previous product in DCM under Ar(g). After 12 hours, the reaction was quenched with water, and the product extracted with DCM. The organic layers were combined and dried with anhydrous sodium sulfate. DCM was removed under vacuum to obtain crude product. Purification was carried out by recrystallization in EtOAC/DCM solution at 0° C. or on silica gel (25-50% EtOAC in Hexanes). ESI-MS (m/z): 323.1/325.1 (product 1), 247.1/249.1 (product 2).

Starting reagents were dissolved in acetonitrile and 1.5 equivalents DIPEA added. Stir for 8 hours or until completion (monitored by ESI-MS). Solvent was removed under vacuum, and the crude product purified on basic alumina (1-10% MeOH in DCM). ESI-MS (m/z): 489.6 (product 1), 413.5 (product 2)

Dissolved ligand from previous reaction in ethanol, 2 equivalents of KOH dissolved in water added. Stirred for about 4 hours or until completion (monitored by ESI-MS). Solvent removed under vacuum. Equivalent portions of 1M HCl and DCM were added. Extracted product in DCM (3×), combined layers, and dried with anhydrous sodium sulfate.

Dissolved ligand in ethanol and added 1 equivalents of FeCl$_2$ while stirring at 60° C. After completion of metalation (monitored by ESI-MS), diethyl ether was added until product precipitates. Filtered product and washed with diethyl ether and dried under vacuum.

ICP-MS. Iron concentration was determined using Thermo X-Series 2 ICP-MS. All samples were diluted (1 μM) with 2% nitric acid in 10 mL total water solution and were decomposed by heating (90° C.) for 24 hours. A linear calibration curve for iron metal ranging from 0.1 ppb to 250 ppb was generated daily for the quantification. Samples were digested in nitric acid over a period of four days and the iron concentration determined.

Magnetic moments. Samples for studies of magnetic moment by using the Evans method were prepared using a coaxial NMR insert which contained the diamagnetic standard of 5% t-butanol in D$_2$O. The outer 5 mm NMR tube contained 5 mM paramagnetic complex with fixed concentrations; 4 mM, 8 mM, 40 mM, and 70 mM in presence of 5% t-butanol. The effective magnetic moment ($\mu_{eff}$, BM) was calculated by using a modified Evans method for small molecules at 298 K (T).

Preparation of Samples for Phantom MR Imaging: Samples for phantom imaging experiments contained 50-500 μM complex, 20 mM HEPES and 100 mM NaCl. For samples containing Human Serum Albumin (HSA), 35 mg of HSA was added to these solutions. The pH of all solutions was adjusted to 7.0.

Phantom (in vitro) imaging at 4.7 T. MRI acquisitions were performed using a General Electric 4.7 T/33 cm horizontal bore magnet (GE NMR instruments, Fremont, Calif.) incorporating AVANCE digital electronics (Bruker BioSpec platform with ParaVision v 3.0.2 acquisition software, Bruker Medical, Billerica, Mass.). Each complex was diluted with HEPES in 100 mM NaCl (pH 7.4) to a concentration ranging from 0.0.5 mM to 400 mM and imaged at 25° C. $T_1$ relaxation rates ($r_1$) were acquired utilizing a saturation recovery, spin-echo (SE) sequence with a fixed echo time (TE), 10 ms and repetition times (TR) ranging from 75 to 8000 ms. Signal intensities at each repetition time were sampled by taking the mean intensity within regions of interest (ROI's) using commercially available image processing software (Analyze 7.0, AnalyzeDirect, Overland, Kans.), and $r_1$ and SMAX were calculated by nonlinear fitting of the equation using Matlab's Curve Fitting Toolbox (Matlab 7.0, MathWorks Inc., Natick, Mass.). The $T_1$ relaxivity for each complex was then determined by obtaining the slope of the compound's molar concentration vs $r_1$ via linear regression fitting of the data. Similarly, $T_2$ relaxation rates ($R_2$) were acquired using a multiecho, Carr-Purcell-Meiboom Gill (CPMG) SE sequence with a fixed TR of 2500 ms and TE times ranging from 15 to 300 ms, NEX) 2. $R_2$ and SMAX were calculated as described above using the equation As before, the $T_2$ relaxivity was determined by obtaining the slope of concentration vs $r_2$ via linear regression fitting of the data.

Figure 17:
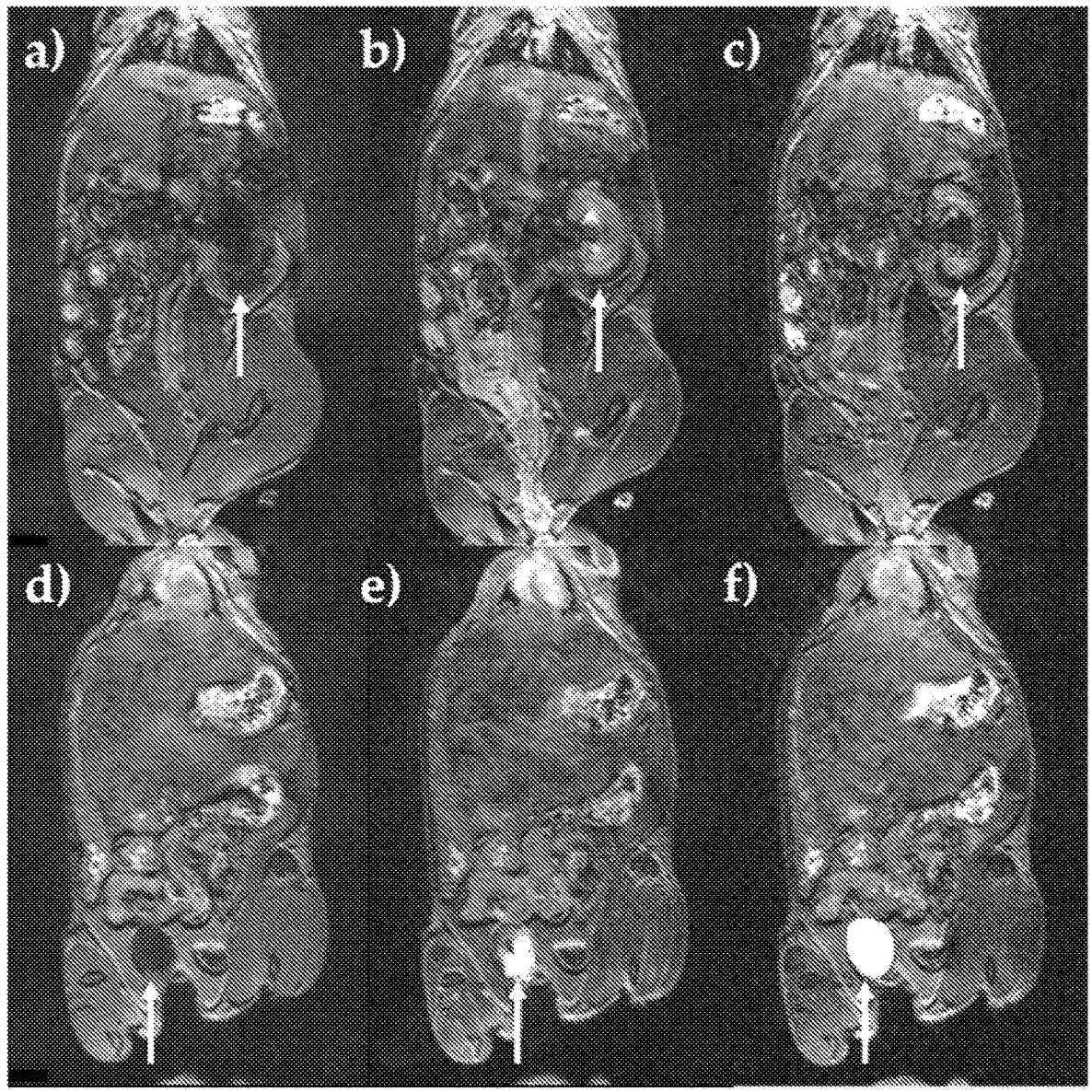
FIG. 17 shows $T_1$-weighted MRI of a healthy Balb/C mouse at 4.7 T at a dose of 0.2 mmol/kg of Fe(TASO). Top row: before (a), after 5 min (b) and 40 min (c) post-injection images showing enhancement of kidneys (arrow). Bottom row: urinary bladder images (arrow) before (d), after 5 min and 40 min (f).
Figure 18:
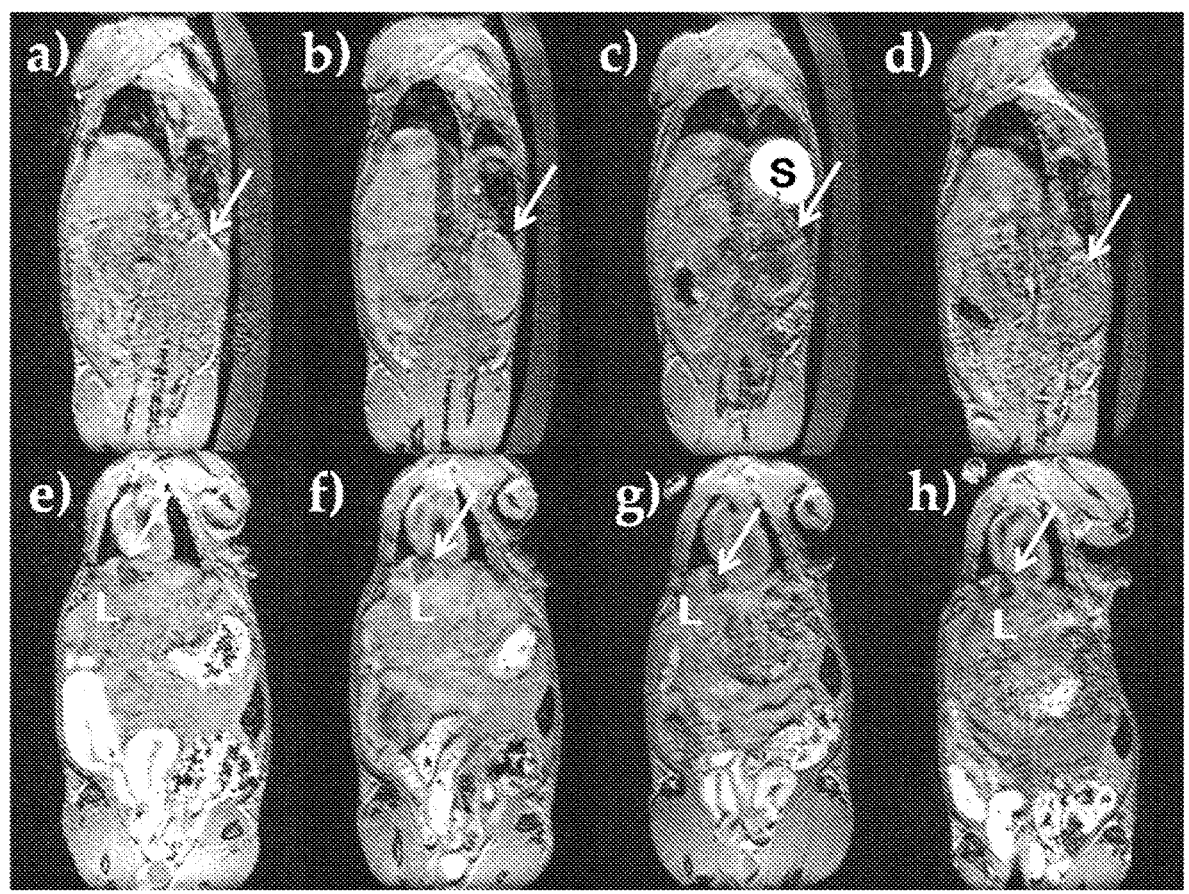
FIG. 18 shows $T_1$-weighted MRI of a healthy Balb/C mouse at 4.7 T at a dose of 0.05 mmol/kg Fe(TASO). Top row: before (a), after 30 minutes (b), 4 hours (c) and 24 hours (d) post-injection images showing enhancement of kidneys (arrow). Stomach was labelled as S. Bottom row: liver (L) and gall bladder images (arrow) before (e), after 30 minutes (f), 4 hours (g) and 24 hours (h) post-injection images.

In vivo imaging in mice. Efficacy of the Fe(III) complexes for in vivo contrast enhancement was studied on at 4.7 T Bruker preclinical MRI in a mouse model (BABC/cJ, Jackson Laboratory). Sealed phantoms were included for imaging sessions for signal normalization. Prior to administration of contrast agents, scans were acquired to serve as baseline values of enhancement. Two scan protocols were used: (1) a $T_1$-weighted, 3D, spoiled-gradient echo scan covering the mouse from thorax to tail to determine signal enhancement and (2) inversion-recovery, steady state free precession scans (IR-SSFP) to measure $T_1$ rates in the blood (inferior vena cava), kidneys, liver, gall bladder and back muscle. Compounds were injected intravenously via tail vein at a dose of 50-200 µmol [Fe]/kg and MR data were acquired continuously for up to 1 hour after injection to study distribution and clearance kinetics. Thus, 0.2 mL of a 6 mM stock solution was injected into the mouse at 0.05 mmol/kg, 0.100 mmol/kg, or 0.200 mmol/kg. Additional scans were acquired at 3 and 6 hours post-injection to characterize slower clearance rates by the biliary system. The FDA-approved MRI contrast agent gadopentetate dimeglumine (Gd-DTPA, Magnevist®) or Dotarem (Gd(DOTA)) was injected into a separate cohort of mice at 50 µmol [Gd]/kg for comparison. Data is shown in FIGS. 17 and 18. For SPGR datasets, signal intensities were normalized to the phantoms and signal increase for each organ was measured, as well as an increase in contrast-to-noise ratios as compared to back muscle. Fe(III) concentrations were estimated by calculating the increase in $T_1$ rates and dividing by the compound's relaxivity value as determined in vitro.

NOTP Synthetic Scheme

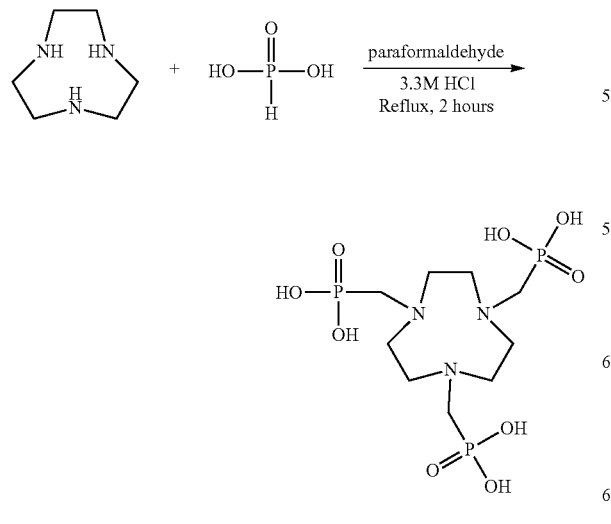

NOTP Iron Complexation

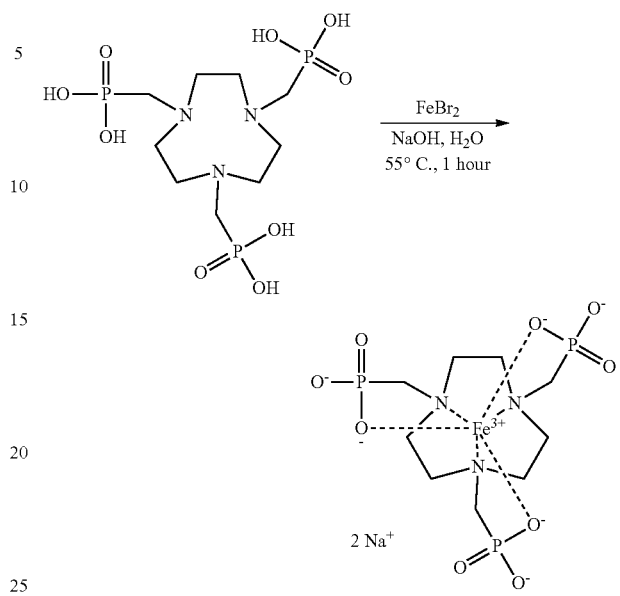

Figure 11:
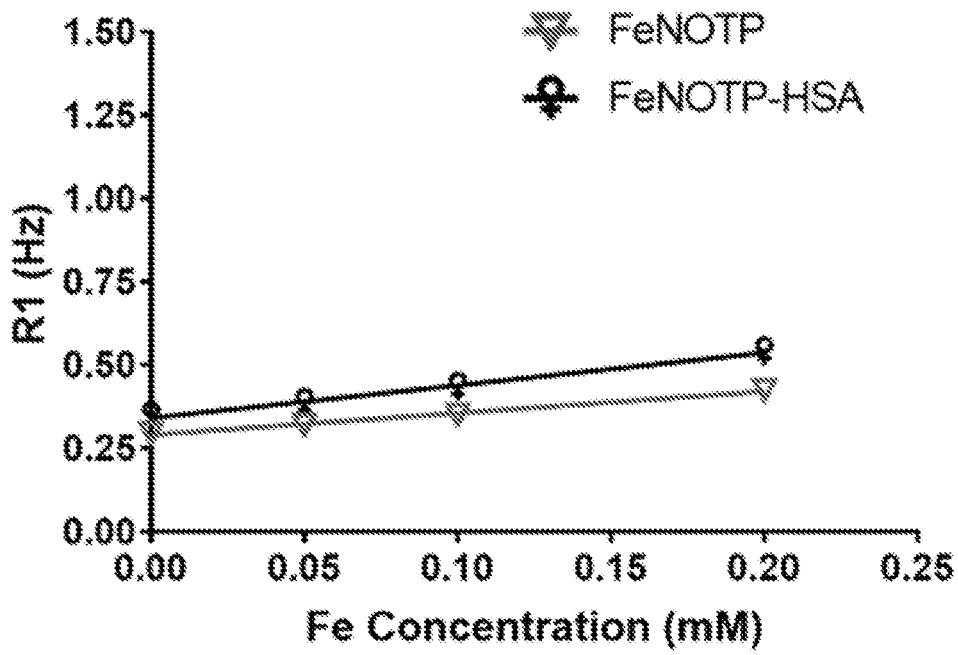
FIG. 11 shows relaxivity data obtained at 4.7 Tesla and 37° C. for examples of a macrocyclic complex of the present disclosure. Fe-NOTP exhibited a $r_1$ of 0.66±0.01 mM$^{-1}$ s$^{-1}$ and Fe-NOTP with HSA exhibited a $r_1$ of 1.04±0.06 mM$^{-1}$ s$^{-1}$.

FIG. 11 shows relaxivity data for examples of a macrocyclic complex of the present disclosure. Fe-NOTP exhibited a $r_1$ of 0.66±0.01 mM$^{-1}$ s$^{-1}$ and Fe-NOTP with HSA exhibited a $r_1$ of 1.04±0.06 mM$^{-1}$ s$^{-1}$.

NOTP was synthesized using a procedure similar to those found in literature. The off-white precipitate was collected via vacuum filtration and then recrystallized from a 50:50 hot water: ethanol mixture multiple times until a pure white solid was formed. MS (ESI negative mode) m/z: 410.2 (M–H$^+$). $^1$H NMR (D$_2$O) 3.19 (6H, doublet, J 11.30) 3.42 (12H, singlet). $^{31}$P NMR (D$_2$O) 11.95. $^{13}$C NMR (D$_2$O) 51.02 (6C, singlet) 53.03 (3C, doublet, J 141.61).

The purified NOTP ligand (0.33 mmol) was dissolved in water (20 mL) along with sodium hydroxide (1.01 mmol, 3 equivalents). This solution was heated to 55° C. for 5 minutes. After the five minutes, a solution of FeBr$_2$ (0.33 mmol, 1 equivalent) in water (10 mL) was added to the hot solution. The combined solutions were allowed to heat for one additional hour. Upon cooling to room temperature, the solvent was evaporated under reduced pressure resulting in a yellow oil. The yellow oil was dissolved in water (2 mL) and ethanol (20 mL) was added to induce a yellow solid to precipitate. The solid was collected and dried. MS (ESI negative mode) m/z: 463.2 (M–H$^+$). Here M is the neutral Fe(NOTP) complex. $\mu_{\mathit{eff}}$ 5.85±0.14. ICP-MS Purity: 95%. Log P octanol water of Fe-NOTP: −2.02±0.30.

Synthesis of DAPO. DAPO was synthesized as follows:

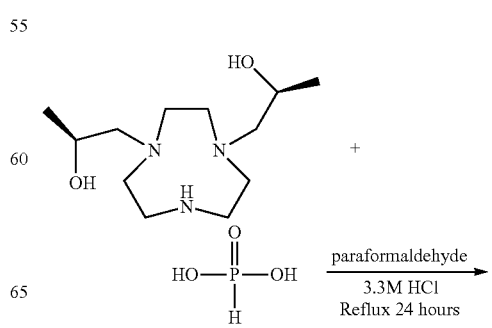

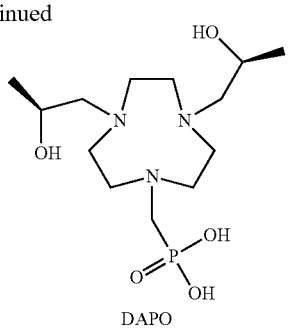

DAPO 1,4,7-triazonane-1,4-diyl-bis(propan-2-ol) was synthesized as previously published. 1,4,7-triazonane-1,4-diyl-bis(propan-2-ol) (0.301 mmol) was dissolved in 500 L of 3.3M HCl solution. To this solution phosphorous acid (1.80 mmol, 6 equivalents) was added and the mixture was set up to reflux. Upon reaching reflux paraformaldehyde (1.35 mmol, 4.5 equivalents) was added over the course of one hour, after which the solution was allowed to reflux for an additional 24 hours.

Synthesis of TRAP-POP. TRAP-POP was synthesized as follows:

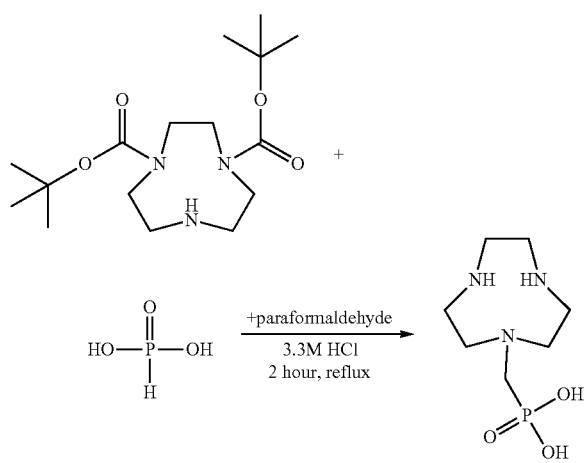

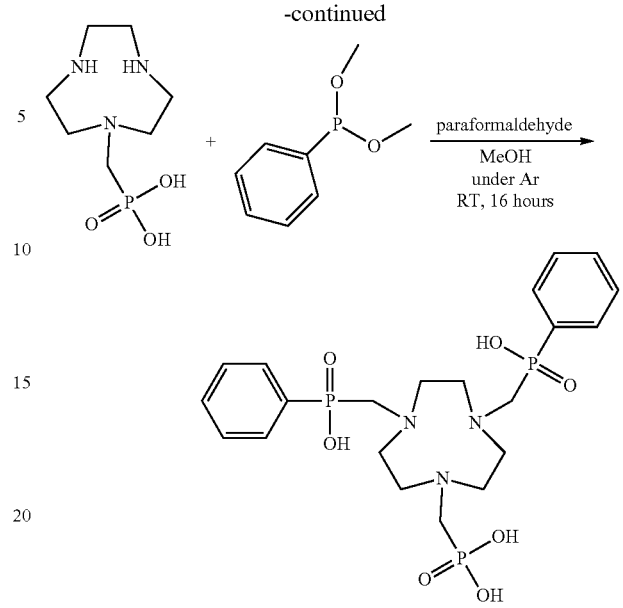

TRAP-POP

Di-tert-butyl 1,4,7-triazacyclonane-1,4-dicarboxylate was synthesized as published in literature. 0.566 mmol was dissolved in 1.1 mL of 3.3 M HCl along with phosphorous acid (1.98 mmol, 3.5 equivalents). This solution was set up to reflux, and upon reflux being reached paraformaldehyde (1.13 mmol, 3 equivalents) were added over the course of one hour. Once all the paraformaldehyde was added the solution was allowed to reflux for an additional hour. MS-ESI: 224.1 [M+H$^+$]. The product from step 1 (1.52 mmol) was dissolved in 30 mL MeOH and argon was used to create an inert atmosphere. Dimethyl phenylphosphonite (3.04 mmol, 2 equivalents) and paraformaldehyde (1.52 mmol, 1 equivalence) were added and the solution stirred at room temperature for 16 hours. Solvent was removed under reduced pressure. MS-ESI (negative mode): 557.7 [M–H$^+$]. Here M is the neutral ligand.

Synthesis of NOTPMe. NOTPMe was synthesized as follows:

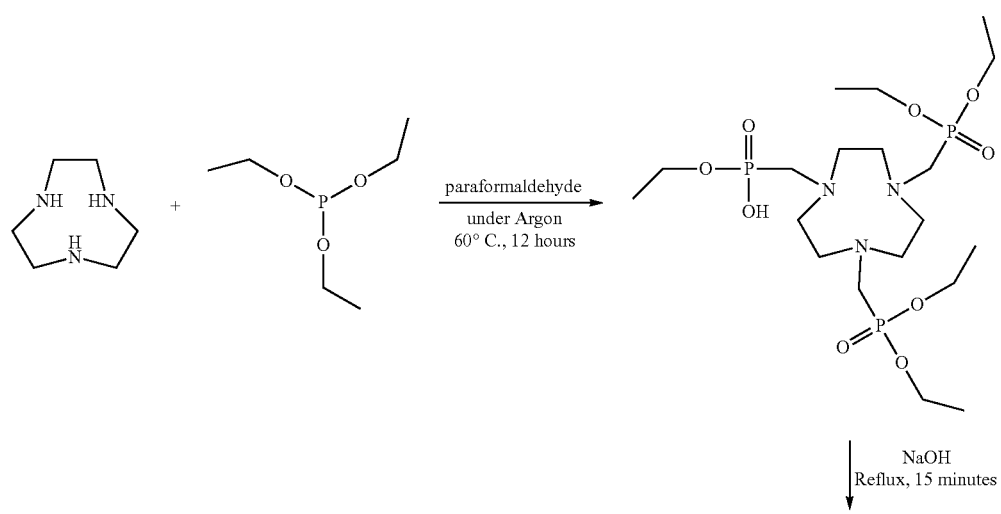

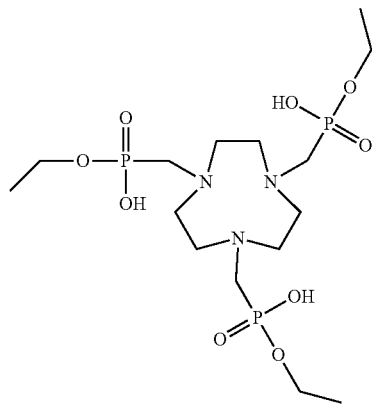

Synthesis was performed at reported in literature. ESI-MS: 494 [M+H⁺], 516 [M+Na⁺]. Here M is the neutral ligand.

Synthesis of PhOTO. PhOTO was synthesized as follows:

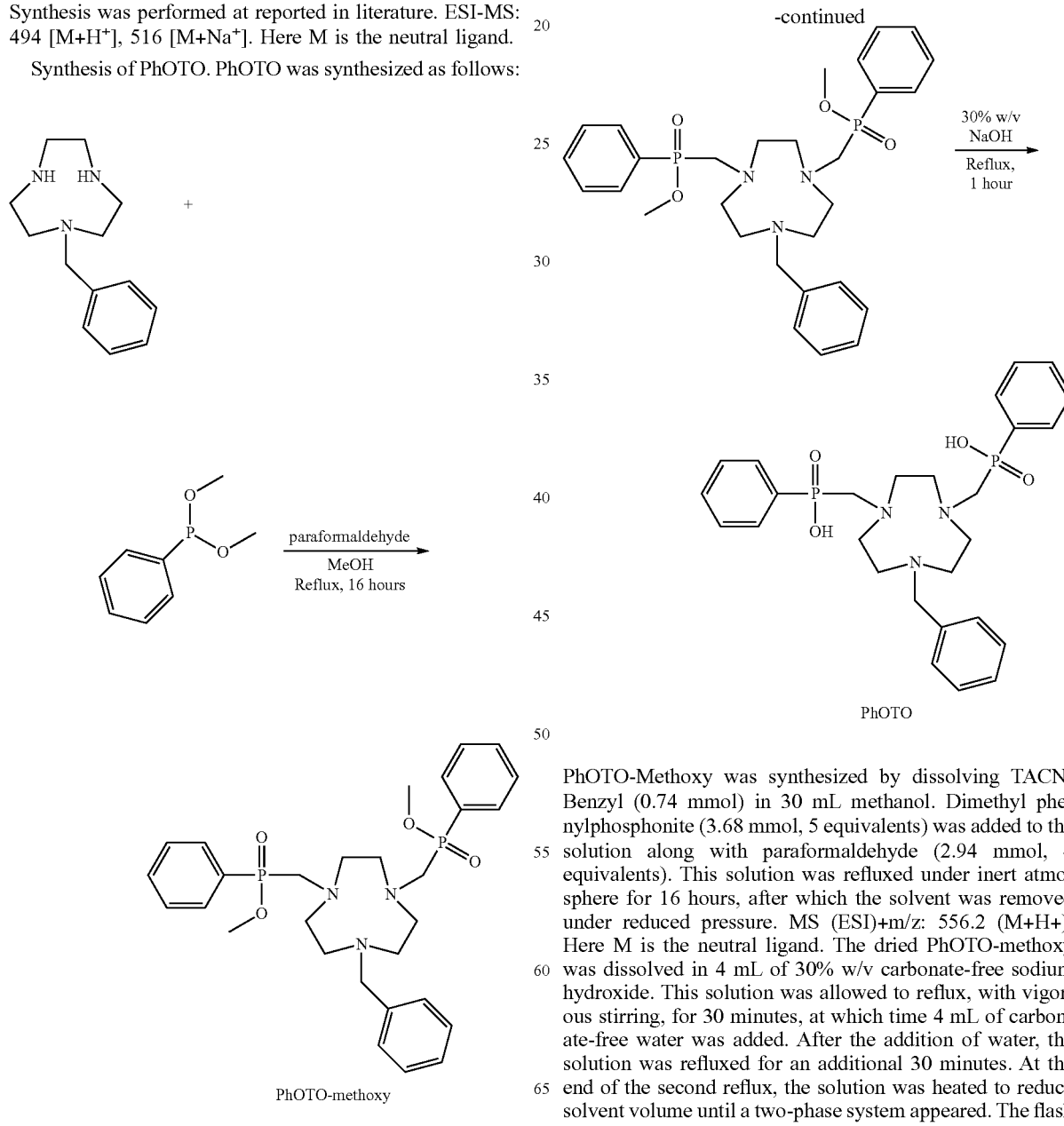

PhOTO-Methoxy was synthesized by dissolving TACN-Benzyl (0.74 mmol) in 30 mL methanol. Dimethyl phenylphosphonite (3.68 mmol, 5 equivalents) was added to the solution along with paraformaldehyde (2.94 mmol, 4 equivalents). This solution was refluxed under inert atmosphere for 16 hours, after which the solvent was removed under reduced pressure. MS (ESI)+m/z: 556.2 (M+H+). Here M is the neutral ligand. The dried PhOTO-methoxy was dissolved in 4 mL of 30% w/v carbonate-free sodium hydroxide. This solution was allowed to reflux, with vigorous stirring, for 30 minutes, at which time 4 mL of carbonate-free water was added. After the addition of water, the solution was refluxed for an additional 30 minutes. At the end of the second reflux, the solution was heated to reduce solvent volume until a two-phase system appeared. The flask was allowed to cool to room temperature. The top layer (oil)

was collected, dissolved in ethanol, and then evaporated to dryness. MS (ESI) m/z: 526.4 (M–H+). Here M is the neutral ligand.

Synthesis of TOPA. TOPA was synthesized as follows:

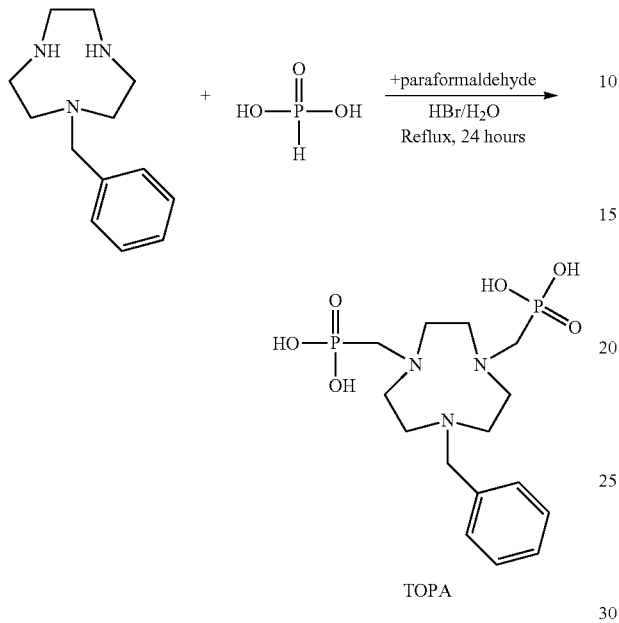

TOPA 1-benzyl-1,4,7-triazacyclononane was synthesized according to previously published procedures. 1-benzyl-1,4,7-triazacyclononane (0.576 mmol) was measured into a two-neck flask and set up on a reflux apparatus. Phosphorous acid (6.91 mmol, 12 equivalents) was additionally added to the flask along with 0.200 mL hydrobromic acid and 0.538 mL of distilled water. Once this solution was brought to reflux, paraformaldehyde (1.15 mmol, 2 equivalents) was added to the solution over the course of an hour. After the addition of paraformaldehyde was complete, the solution was allowed to reflux for 24 hours. The solution was then reduced to minimal volume, and loaded onto a Dowex H+ ion exchange column. First, the column was eluted with water to remove impurities followed by a 5% ammonium hydroxide solution to elute the product. The fractions containing the ligand were dried under reduced pressure and dissolved in water. An Amberlite CG-50-type 1 ion exchange column was used to obtain a product that was eluted with water to give a white solid. MS (ESI) m/z: 406.18 (M–H+). Here M is the neutral ligand. $\delta_H$ ($D_2O$) 3.05 (4H, doublet, J 10.96) 3.32 (12H, multiplet) 4.34 (2H, singlet) 7.38 (5H, multiplet). $\delta_P$ ($D_2O$) 14.93.

Bis(phosphonate) biphenyl TACN (TOBP). A similar procedure to that for the TOPA ligand was used, starting from the biphenyl TACN derivative. $\delta_H$ ($D_2O$) (500 MHz): doublet (2H, 7.704-7.687) doublet (2H, 7.644-7.628) doublet (2H, 7.601-7.585), triplet (2H, 7.452-7.421), triplet (1H, centered 7.354), singlet (4.369, 2H), broad resonances between 3.365-2.973, representing approximately 21 H. MS (ESI) m/z: 484.2 (M–H+). The Fe(III) complex was prepared by addition of Fe(NO$_3$)$_3$ and overnight reflux. MS (ESI) m/z: 535.17 (M–). Here M is the neutral Fe(TOBP) complex.

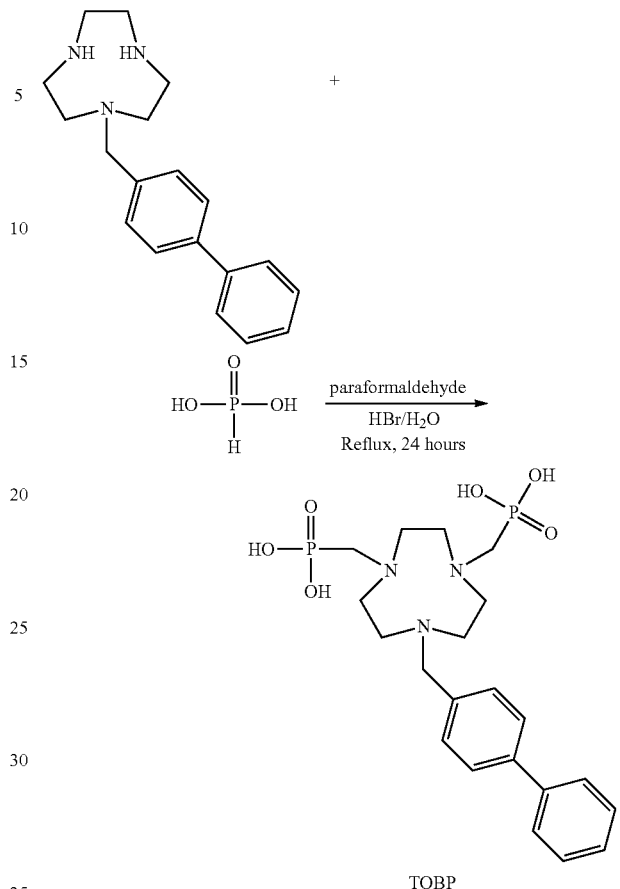

TOBP

Synthesis of TRAP-OPO. TRAP-OPO was synthesized as follows:

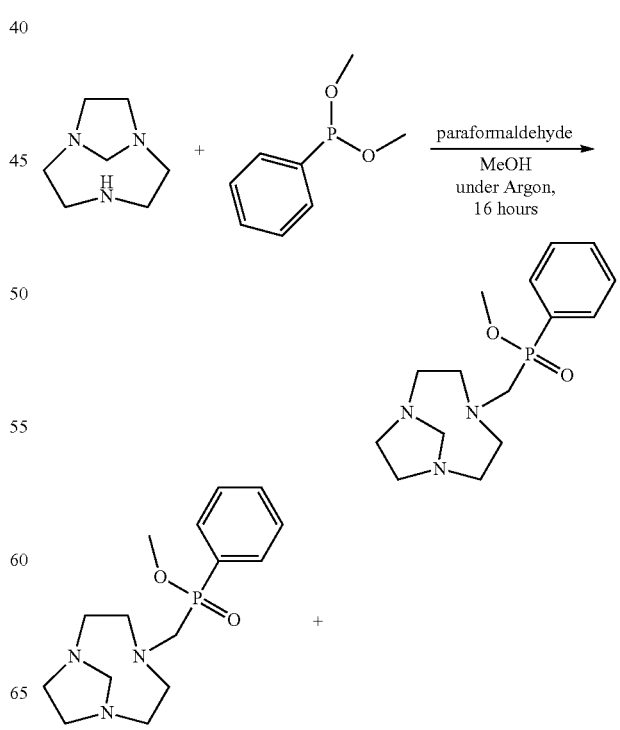

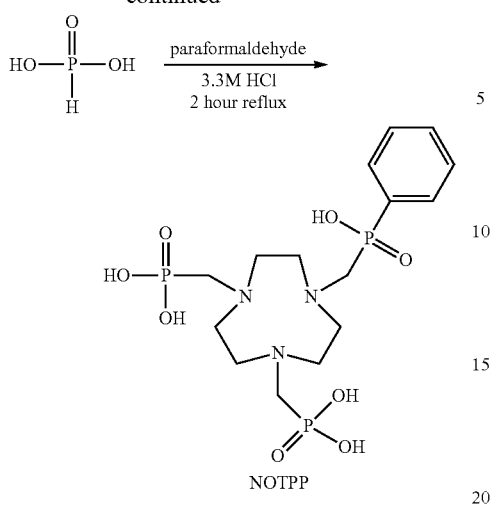

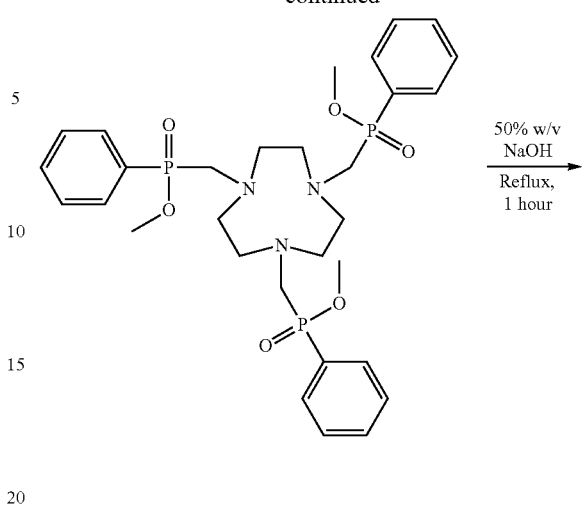

Dissolve 1,4,7-triazabicyclo[5.2.1]decane (0.475 mmol) in 10 mL of methanol. An inert atmosphere was created and dimethyl phenylphosphonite (0.095 mmol, 0.2 equivalents) was added along with paraformaldehyde (0.118 mmol, 0.25 equivalents). The solution was allowed to stir at room temperature overnight and the solvent was removed under reduced pressure. MS-ESI: 310.2 [M+H$^+$]. Here M is the neutral ligand. The dried down methyl ((1,4,7-triazabicyclo[5.2.1]decan-4-yl)methyl)(phenyl)phosphinate (0.221 mmol) was dissolved in 400 μL of 3.3M HCl and phosphorous acid (1.11 mmol, 5 equivalents) was added. This solution was set up to reflux and upon reaching reflux paraformaldehyde (0.442 mmol, 2 equivalents) was added over the course of one hour. After the addition of the paraformaldehyde was complete, the solution refluxed for one additional hour. MS-ESI (negative mode): 470.5 [M–H$^+$]. Here M is the neutral ligand.

Synthesis of TRAP-Ph. TRAP-Ph was synthesized as follows:

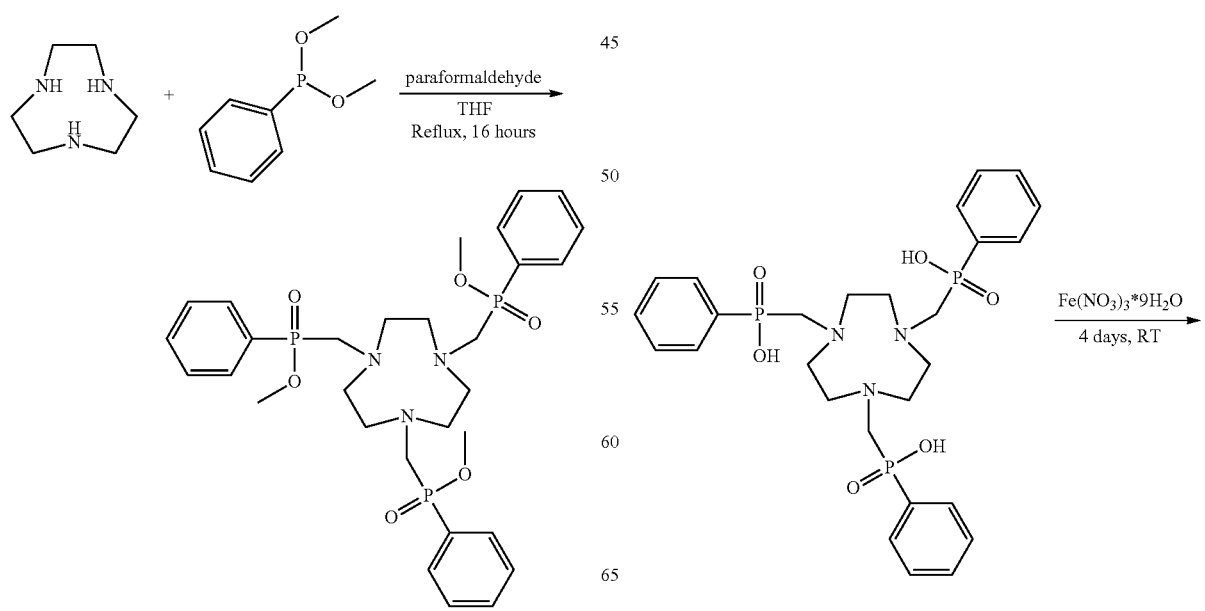

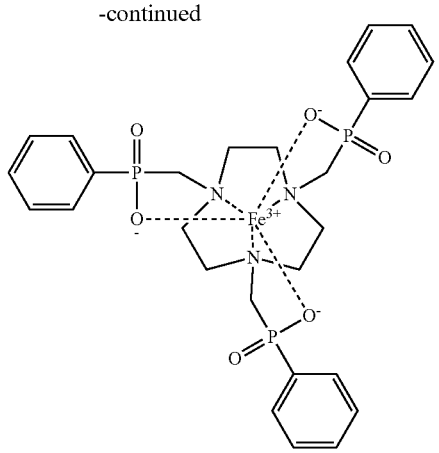

TRAP-Ph-methoxy was synthesized as previously reported. The dried TRAP-Ph-methoxy was dissolved in 4 mL of 50% w/v carbonate-free sodium hydroxide. This solution was allowed to reflux, with vigorous stirring, for 30 minutes, at which time 4 mL of carbonate-free water was added. After the addition of water, the solution was refluxed for an additional 30 minutes. At the end of the second reflux, the solution was heated to reduce solvent volume until two-phases appeared. The solution was allowed to cool to room temperature and the top layer (oil) was removed, dissolved in ethanol, and then evaporated to dryness. The TRAP-Ph was then purified by precipitation. The excess salt was removed by precipitating out the salt using methanol. The methanol was removed under reduced pressure and upon addition of acetone another solid formed which was recrystallized with dichloromethane. MS (ESI) m/z: 590.7 (M–H$^+$). $^1$H NMR (D$_2$O, pD~0.9) 3.02 (12H, multiplet), 3.09 (6H, doublet, J 7.12), 7.31 (9H, multiplet), 7.48 (6H, multiplet) $^{31}$P NMR (D$_2$O, pD-0.9) 29.27. The iron complex was synthesized following a procedure previously published. MS (ESI)+m/z: 645.1 (M+H$^+$), 667.1 (M+Na$^+$). Here M is the neutral ligand.

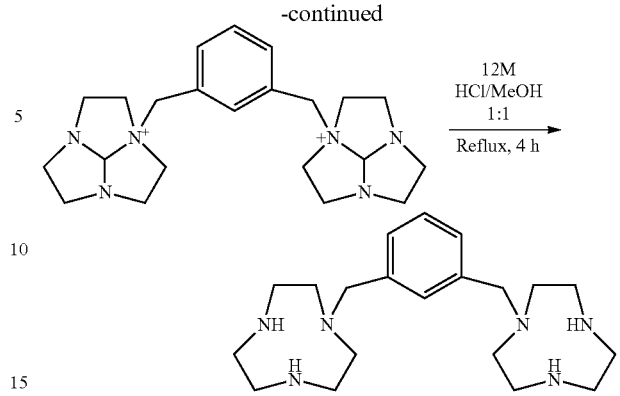

Synthesis of 1,3-bis((1,4,7-triazonan-1-yl)methyl)benzene. To a 25 mL round bottom flask with gas inlet and stir bar was added 0.100 g TACN (0.774 mmol) in 4 mL toluene 1 mL chloroform solution. 0.0920 g N,N-dimethylformamide dimethylacetal (0.774 mmol) was added to the flask. The solution was stirred for 24 hours at room temperature. ESI-MS (m/z) of 1,4,7-triazatricyclo[5.2.1.0$^{4,10}$]decane (TACN orthoamide), calculated: 140.1 [M+H+](100%). The solution was dried by placing flask on a rotoevaporator. The dried TACN orthoamide and 15 mL dry acetonitrile was added in 50 mL 3-necked round bottom flask equipped with a magnet stir bar, reflux condenser, gas inlet tube and addition funnel. 0.100 g α, α'-Dibromo-m-xylene (0.384 mmol) in 10 ml dry acetonitrile solution was added into the flask by dropwise addition with an addition funnel for 30 min. the solution was heated to reflux for 2 hours and was stirred overnight at room temperature. A white-beige color precipitate was collected by suction filtration method and washed with dry acetonitrile (5 mL) and diethyl ether (5 mL). 6 mL methanol and 6 mL 12 M HCl was added to the precipitate in the flask for the deprotection process. The solution was heated to reflux for 4 hours. After the solution was cooled to room temperature, NaOH pellets were added to bring the pH of the solution to 8. Then the solution was filtered to remove NaCl salt precipitate and extracted with chloroform (3×60 mL). ESI-MS (m/z), calculated: 361.4 [M+H+] (100%). Here M is the neutral ligand.

Synthesis of m-diTOPA. 1,3-bis((1,4,7-triazonan-1-yl)methyl)benzene (0.155 mmol) was dissolved in 500 µL of 3.3 M HCl and phosphorous acid (1.86 mmol, 12 equivalents) was added. The solution was attached to a reflux apparatus and upon reaching reflux conditions paraformaldehyde (0.930 mmol, 6 equivalents) was added over the course of one hour. Once all the paraformaldehyde was added the solution was allowed to reflux for an additional hour. MS-ESI$^-$: 735.3 [M–H$^+$]. Here M is the neutral ligand.

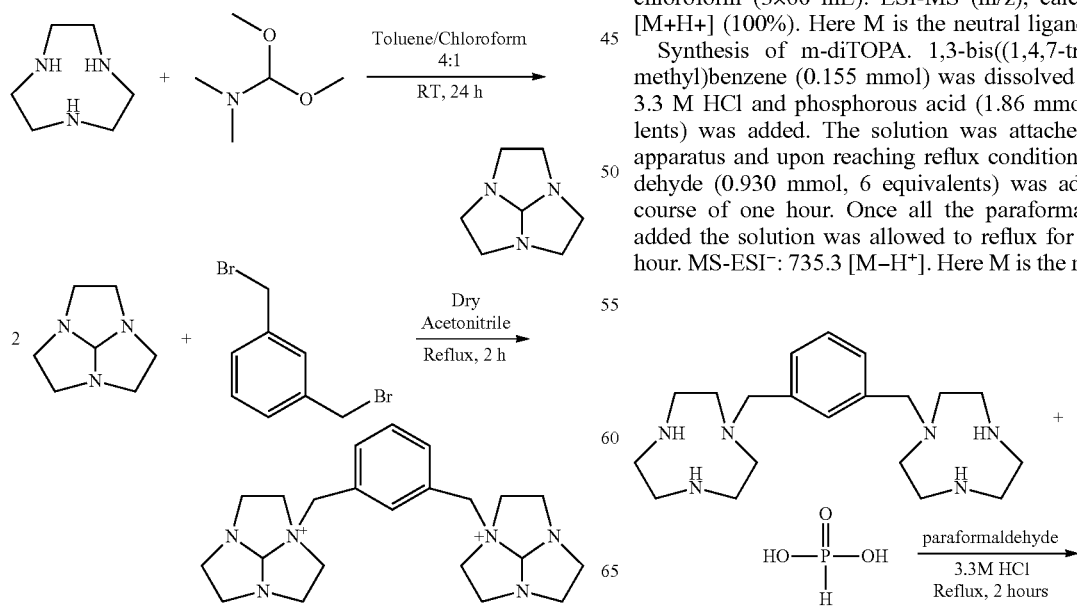

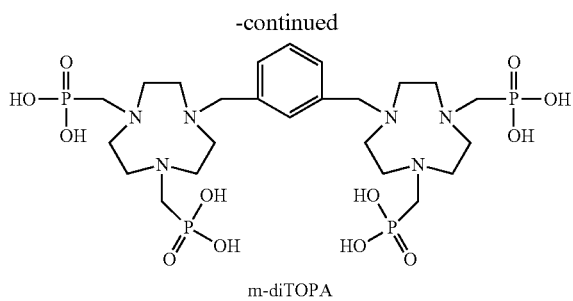

m-diTOPA

Fe(TASO) complex was synthesized using iron(II) chloride tetrahydrate. Product isolated as yellow solid by diethyl ether washing in ethanol solvent. Fe content was calculated through ICP-MS for NaFe(L1)Cl: 11.29%, found: 11.13%±0.17%. LCQ-MS: Found m/z 421.2 (M+H$^+$, 70%), m/z 443.2 (M+Na$^+$, 30%), m/z 841.0 (2M+H$^+$, 100%) and m/z 863.0 (2M+Na$^+$, 18%). Here M is the neutral Fe(TASO) complex. Effective magnetic moment was 5.68.

Figure 12:
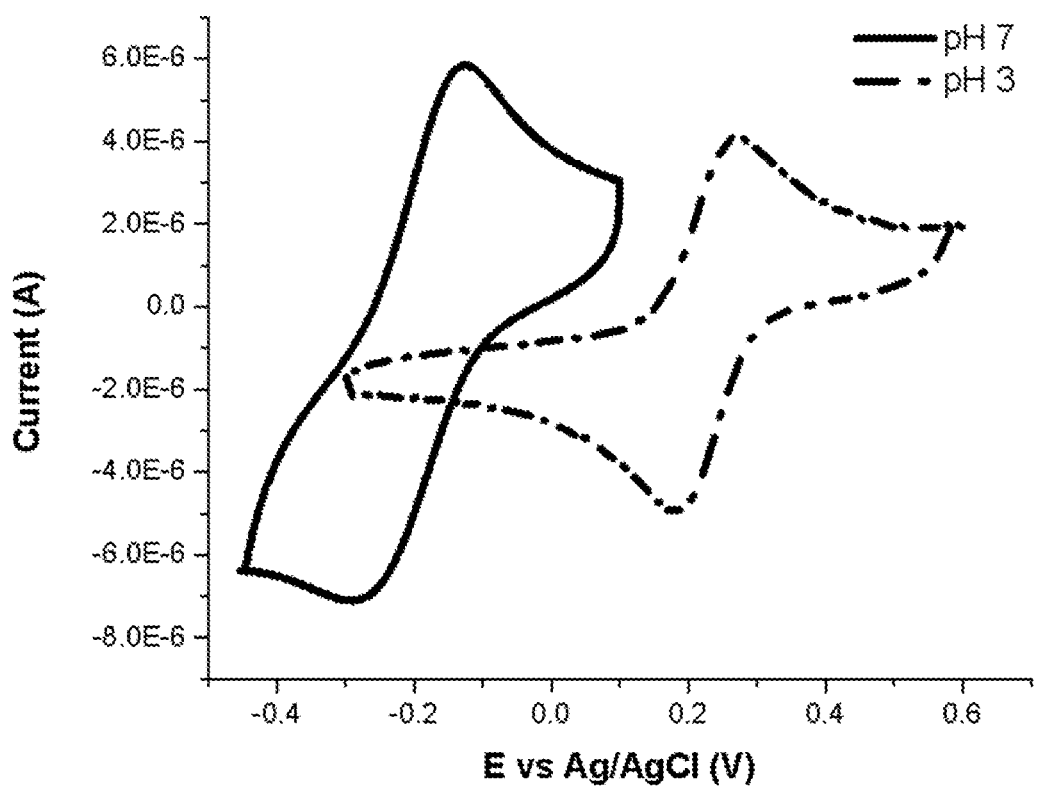
FIG. 12 shows cyclic voltammograms of 1.0 mM solutions of Fe(TASO) at variable pHs in water with potassium chloride (100 mM) as the supporting electrolyte and HEPES buffer. Full sweep widths were taken between −1.5V and 1.5V, at a scan rate of 100 mV/s for Fe(TASO) $E_{1/2}$ at pH 7 was found as −204 mV and at pH 3 was found as 513 mV, corrected against NHE.

Fe(TASO) was characterized by cyclic voltammetry as shown in FIG. 12. Cyclic voltammograms of 1.0 mM solutions of Fe(TASO) were obtained at variable pHs in water with potassium chloride (100 mM) as the supporting electrolyte and HEPES buffer.

Figure 14:
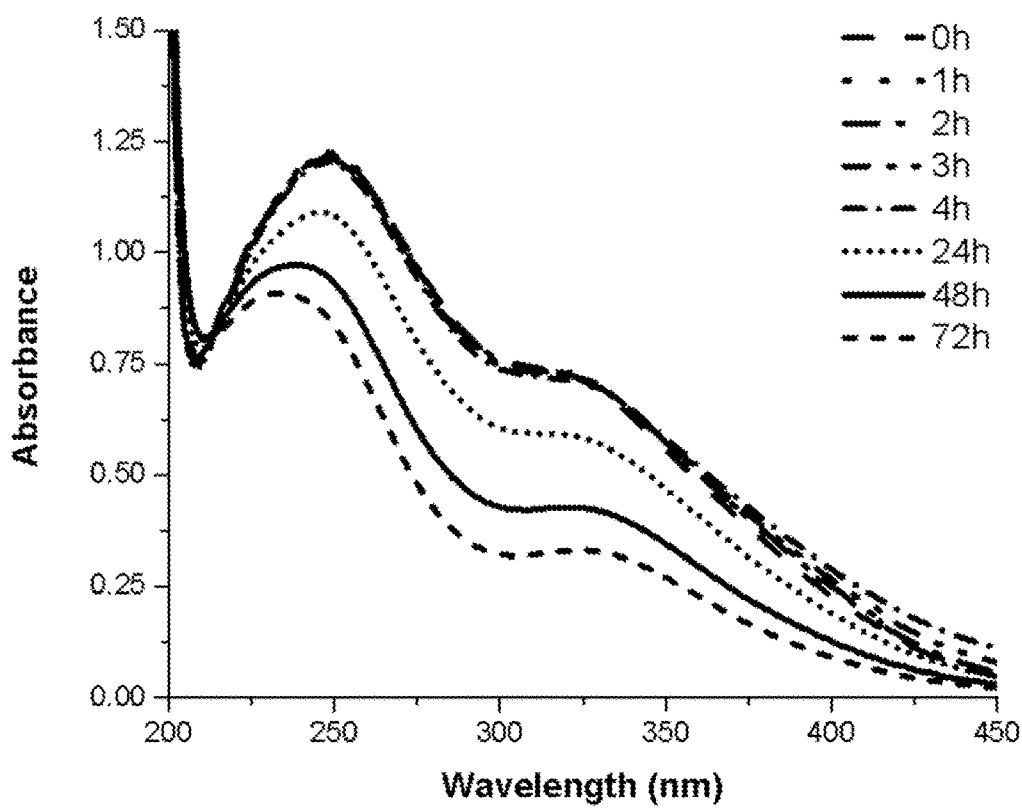
FIG. 14 shows UV-vis absorbance spectra of Fe(TASO) obtained over 72 hours at 37° C. Aqueous solutions contained 0.2 mM Fe(TASO) dissolved in 0.1M HCl. Ɛ (250 nm)=6097 M-cm-, Ɛ (325 nm)=3557 M$^{-1}$ cm$^{-1}$. Dissociation after 24 h was 18.1%. Dissociation after 72 h was 53.6%.
Figure 15:
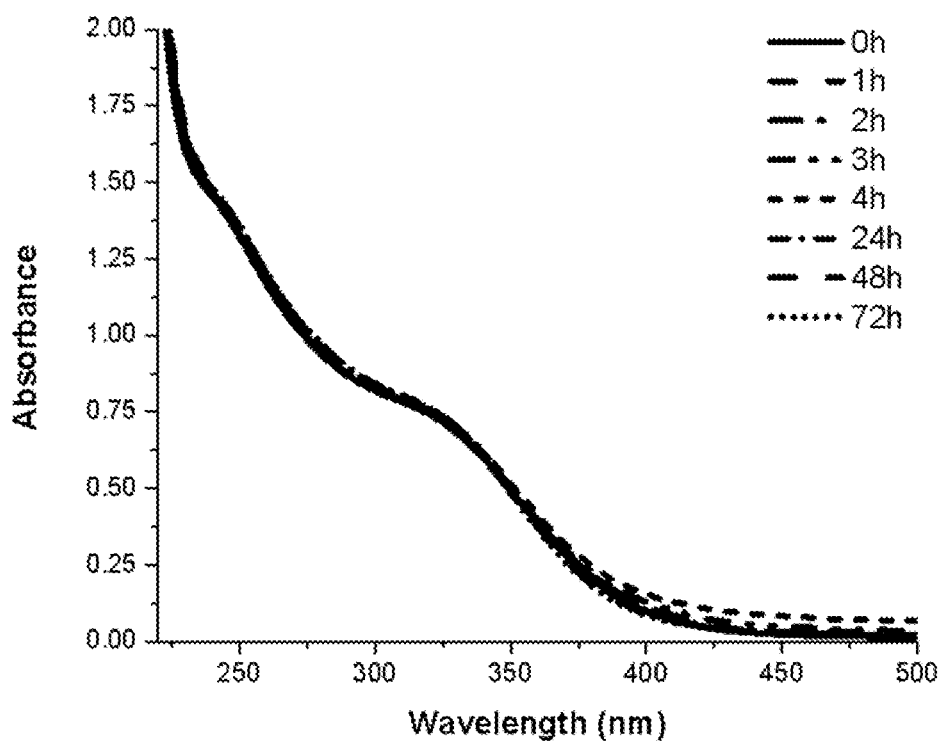
FIG. 15 shows UV-vis absorbance spectra of Fe(TASO) obtained over 72 hours at 37° C. using aqueous solutions containing 0.2 mM Fe(TASO) dissolved in 25 mM $NaHCO_3$, 0.50 mM $Na_2HPO_4$, 10 mM HEPES buffer at 7.1 pH. Ɛ (245 nm)=6960 M-cm-, Ɛ (325 nm)=3571 M$^{-1}$ cm$^{-1}$.
Figure 16:
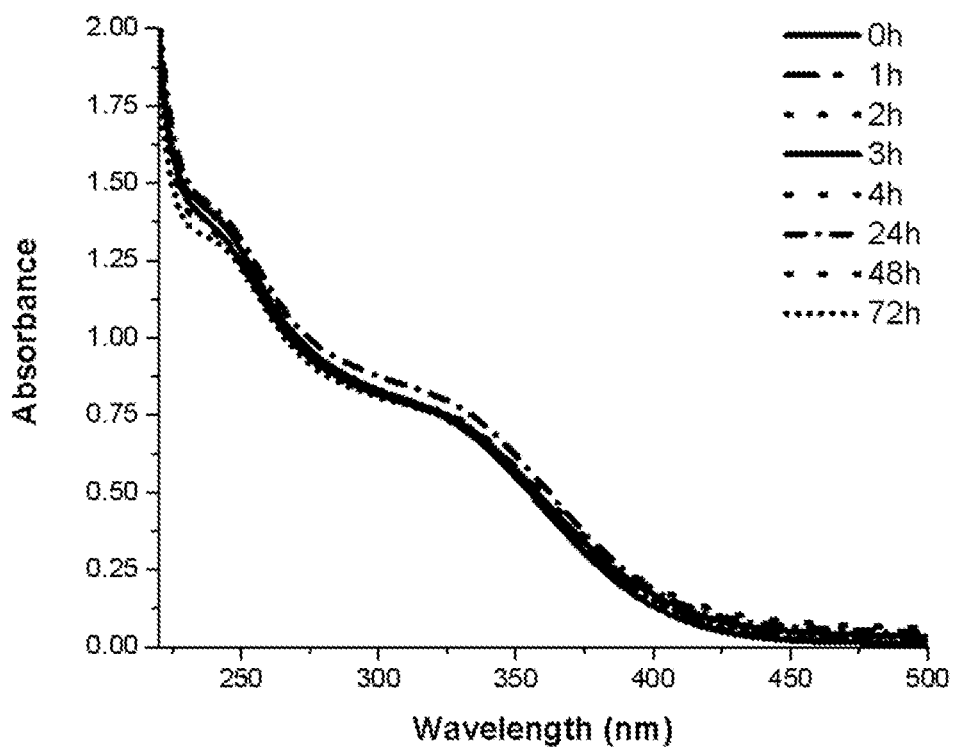
FIG. 16. UV-vis absorbance spectra of Fe(TASO) were obtained over 72 hours at 37° C. Aqueous solutions contained 0.2 mM Fe(TASO) dissolved in 10 mM HEPES buffer at 7.1 pH. Ɛ (245 nm)=6762 M-cm-, Ɛ (325 nm)=3687 M$^{-1}$ cm$^{-1}$.

Fe(TASO) was characterized by UV-vis absorbance. The data are shown in FIGS. 14-16.

TBzC ester. Bis(2-hydroxypropyl)-1,4,7-triazacyclononane (0.245 g, 1.0 mmol) was dissolved in acetonitrile (5.0 mL) and heated to 60° C. Then, anhydrous potassium carbonate (0.207 g, 1.5 mmol) was added to the solution, followed by addition of ethyl 4-(bromomethyl)benzoate (0.304 g, 1.2 mmol). The reaction was stirred for 8-12 h until completion (monitored through ESI-MS). Then, solvent was removed under vacuum and crude product was purified on alumina with 0/100 to 5/95 methanol/dichloromethane with product eluting at about 1/99 methanol/dichloromethane as a faint yellow oil (0.288 g, 71%). $^1$H NMR (500 MHz, DCM-d$_2$) δ 7.98 (d, J=10 Hz, 2H), 7.49 (d, J=10 Hz, 2H), 4.35 (dd, J=15 Hz, 2H), 3.89 (s, 2H), 3.72-3.68 (m, 2H), 2.88-2.76 (m, 6H), 2.67-2.45 (m, 10H), 2.25 (dd, J=10 Hz, 2H), 1.39 (t, J=5 Hz, 3H), 1.05 (d, J=10 Hz, 6H). $^{13}$C NMR (75 MHz, CHCl$_3$-d) δ 167.0, 144.8, 129.5, 129.4, 128.9, 66.5, 63.9, 62.5, 60.8, 55.7, 55.4, 54.6, 19.8, 14.3. ESI-MS: m/z 408.3 (M$^+$, 100%), 430.3 (M+Na$^+$, 10%).

TBZC synthesis. The TBZC ester (0.408 g, 1.0 mmol) was dissolved in ethanol (10.0 mL) and heated to 90° C. Then, NaOH (0.120 g, 3.0 mmol) was added to the solution and reaction stirred for 12-24 h until completion as monitored by ESI-MS. The solution was washed with dichloromethane (3×25 mL) and the aqueous layer was collected. Solvent was removed under vacuum. The ligand was obtained through addition of 12M HCl until solution was pH 3 and product (7) extracted into dichloromethane (3×25 mL). Then, organic layers were combined, dried over anhydrous sodium sulfate and solvent removed under vacuum. Product was isolated as a pale yellow oil (0.278 g, 73%). $^1$H NMR (500 MHz, D$_2$O) δ 7.77 (d, J=5 Hz, 2H), 7.40 (d, J=5 Hz, 2H), 3.82 (q, J=15 Hz, 2H), 3.00 (d, J=10 Hz, 2H), 2.87-2.58 (m, 16H), 1.04 (d, J=5 Hz, 6H). $^{13}$C NMR (75 MHz, D$_2$O) δ 171.0, 140.4, 135.8, 129.7, 129.0, 63.6, 63.0, 60.2, 51.0, 49.7, 48.8, 19.7. ESI-MS: m/z 380.3 (M$^+$, 100%).

Fe(TBZC). The complex was synthesized using ferrous chloride tetrahydrate and the product was isolated as a yellow solid (45.7 mg, 52%). Fe content through ICP-MS calculated for [Fe(H$_2$-L4)Cl]Cl: 9.56%, found: 9.52%±0.10%. FT-ICR-MS: Calculated m/z 514.198541, Found m/z 514.198394 (M$^+$, 100%). Here M is the neutral Fe(TZBC) complex.

Transverse $^{17}$O NMR relaxivity, ln(1/T$_{2r}$) as a function of temperature for Fe(L2) measured at pH 3.5 was measured for various examples of macrocyclic compounds of the present disclosure. The data are shown in FIG. 13.

Relaxivity values for Fe(TASO) with and without HSA measured at 4.7 T and 9.4 T, pH 7.2 and 37° C. compared to Gd(DTPA). The data are shown in Tables 2 and 3.

TABLE 2

Relaxivity values for Fe(TASO) with and without HSA measured at 4.7 T and 9.4 T, pH 7.2 and 37° C. compared to Gd(DTPA).

| Complex | r$_1$ (mM$^{-1}$sec$^{-1}$) 4.7 T | r$_1$ (mM$^{-1}$sec$^{-1}$) 9.4 T | r$_2$ (mM$^{-1}$sec$^{-1}$) 4.7 T | r$_1$ (mM$^{-1}$sec$^{-1}$) in HSA 4.7 T | r$_2$ (mM$^{-1}$sec$^{-1}$) in HSA 4.7 T |
|---|---|---|---|---|---|
| Fe(TASO) | 1.9 ± 0.14 | 1.99/1.64 | 5.8 ± 0.48 | 3.1 | 6.4 |
| Gd(DTPA) | 3.1 ± 0.31 | | 3.9 ± 0.39 | 3.2 ± 0.32 | 4.0 ± 0.40 |

TABLE 3

Log P octanol/water partition coefficients for Fe(TASO) and Fe(TZBC).

| Complex | Log P |
|---|---|
| Fe(TASO) | −1.67 |
| Fe(TZBC) | −1.87 |

Figure 19:
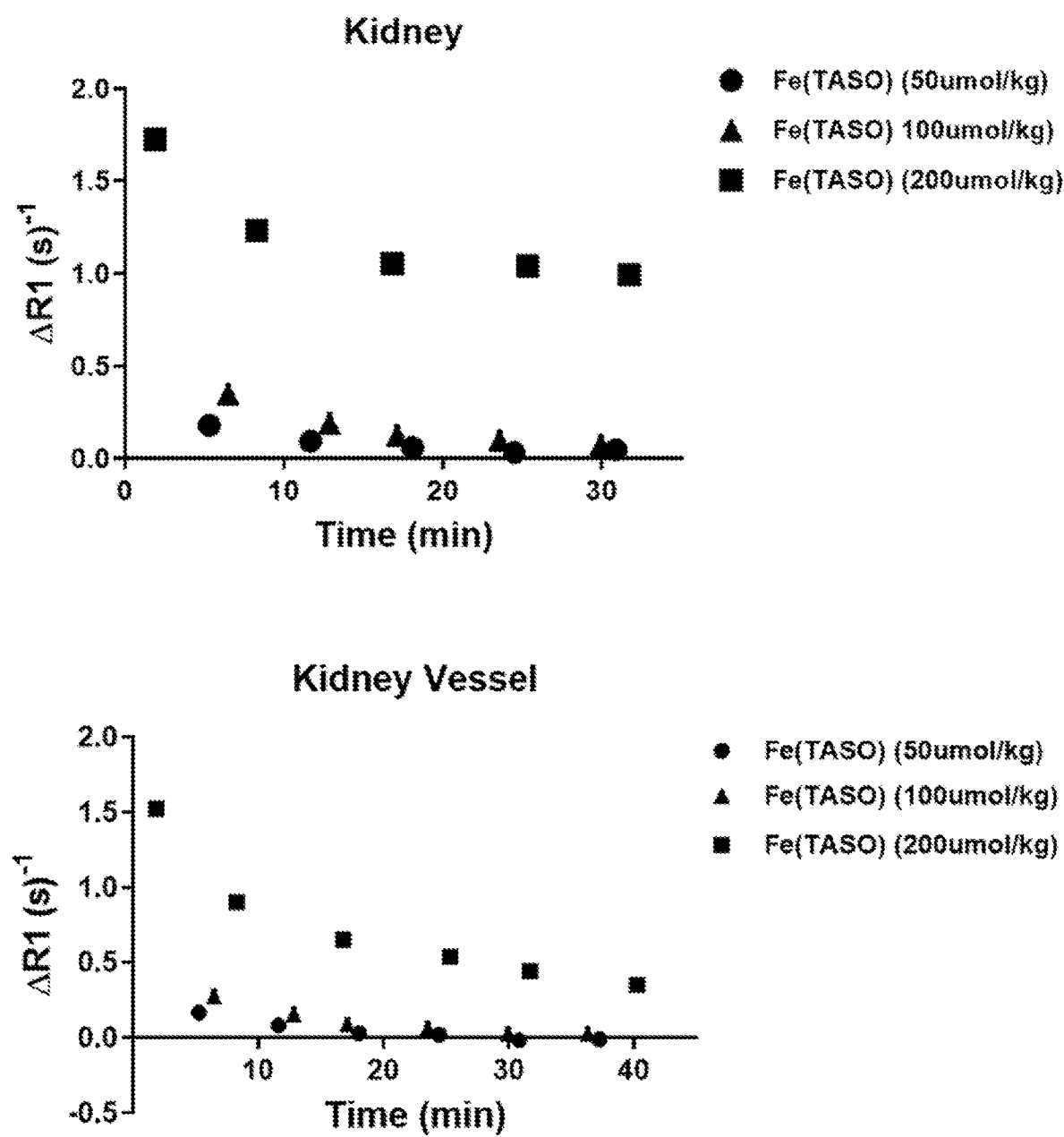
FIG. 19 shows pharmacokinetic data in mice for Fe(TASO).

Fe(TASO) was used as a T$_1$ imaging agent. T$_1$-weighted MRI of a healthy Balb/C mouse at 4.7 T at a dose of 0.2 mmol/kg of Fe(TASO) are shown in FIG. 17. T$_1$-weighted MRI of a healthy Balb/C mouse at 4.7 T at a dose of 0.05 mmol/kg Fe(TASO) are shown in FIG. 18. Fe(TBZC) was used as an imaging agent and the T$_1$ weighted MRI are shown in FIG. 19.

Figure 20:
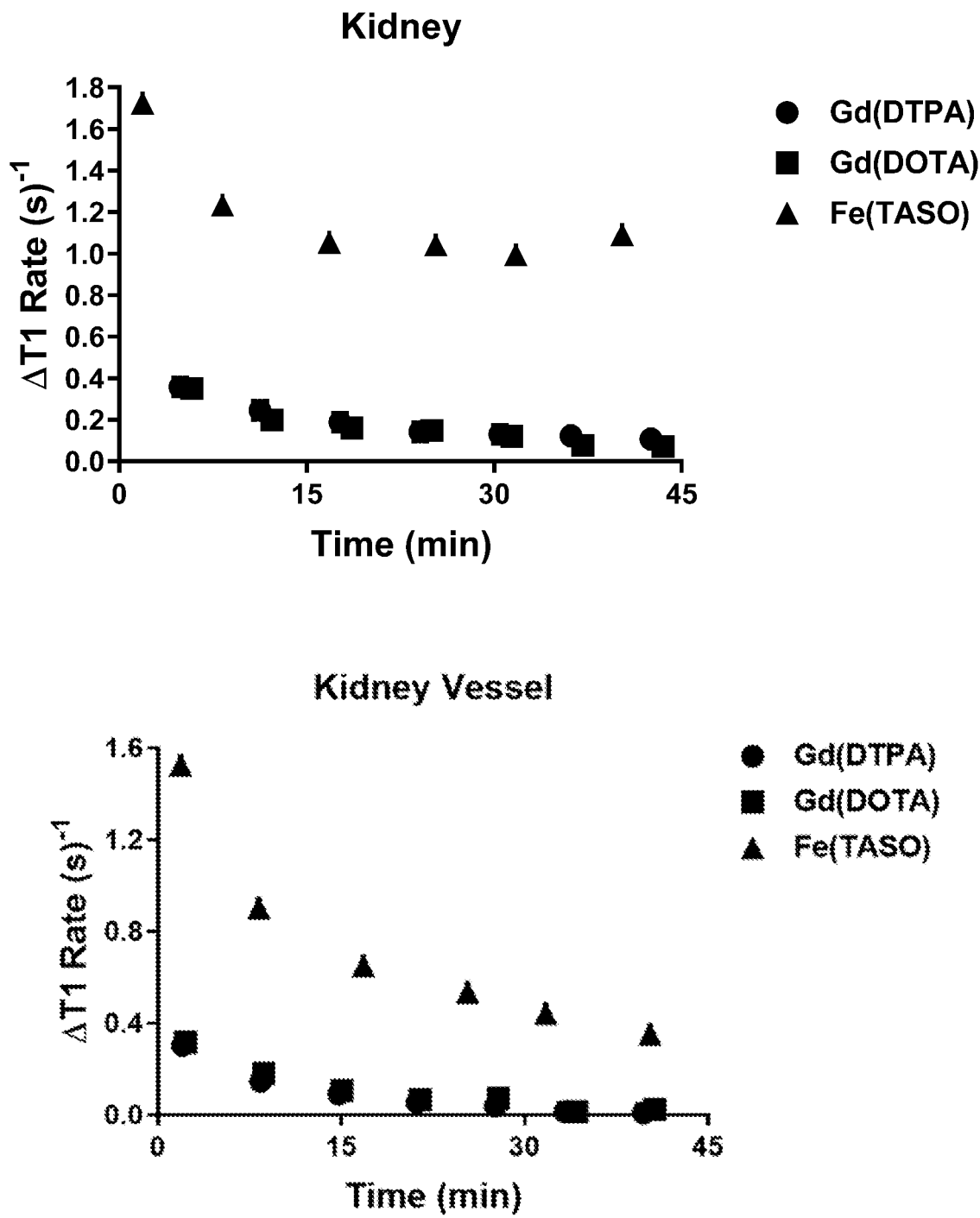
FIG. 20 shows pharmacokinetic data in mice for Fe(TASO) compared to Gd complexes that are used clinically.
Figure 21:
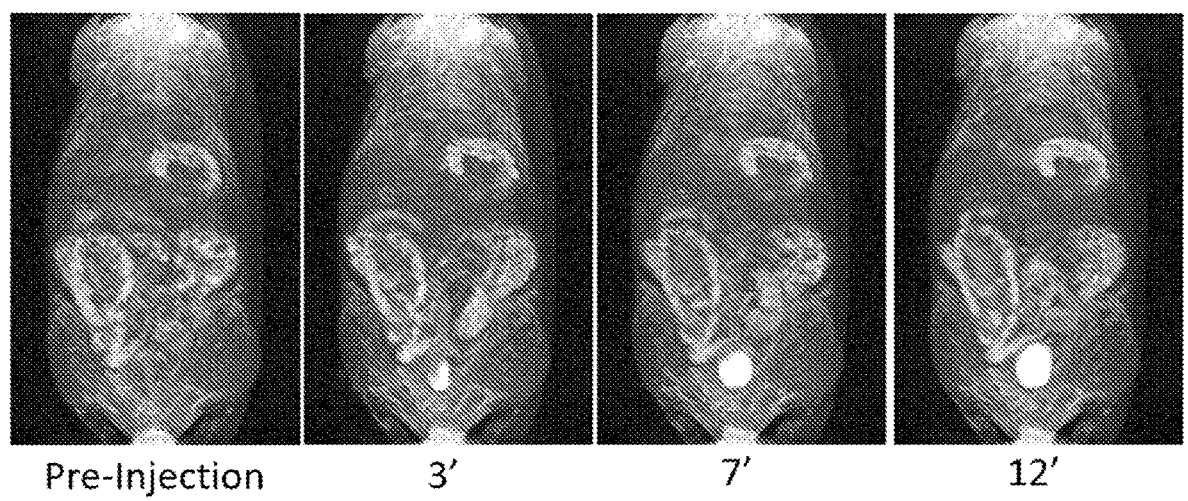
FIG. 21 shows $T_1$-weighted MR images of a healthy Balb/C mouse at 4.7 T of Fe(L4) at a dose of 0.05 mmol/kg at 3, 7, and 12 minutes. Enhancement is shown in the urinary bladder.

Pharmacokinetic studies of Fe(TASO) were carried out. Pharmacokinetic data in mice for Fe(TASO) are shown in FIGS. 19 and 20. T$_1$-weighted MR images were obtained of a healthy Balb/C mouse at 4.7 T at a dose of 0.05 mmol/kg of Fe(L3) Changes in T$_1$ rate constants for Fe(TASO), Gd(DOTA) and Gd-DTPA over time in the kidneys, liver, and blood in a healthy Balb/C mouse at 4.7 T at 0.05 mmol/kg. Signal intensities were normalized to the phantoms, signal increase in each organ was measured and the increase in contrast-to-noise ratios were compared to muscle.

Although the present disclosure has been described with respect to one or more particular embodiments and/or examples, it will be understood that other embodiments and/or examples of the present disclosure may be made without departing from the scope of the present disclosure.

The invention claimed is:

1. A macrocyclic complex comprising:
a 1,4,7-triazacyclononane (TACN) moiety or an O-substituted TACN moiety having a structure:

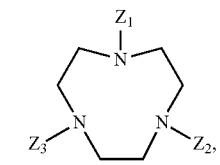
(I)

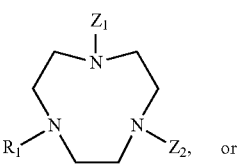
(II)
or

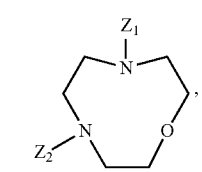
(III)

wherein $R_1$, $Z_1$, $Z_2$, and $Z_3$ are anionic pendent groups independently chosen from:

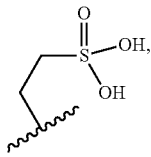 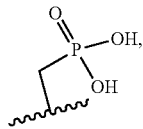 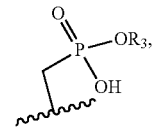

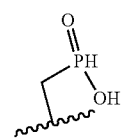 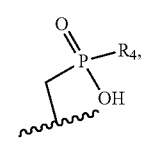

deprotonated analogs thereof, and combinations thereof, wherein $R_3$ is a substituted or unsubstituted alkyl or a substituted or unsubstituted aryl group and $R_4$ is a substituted alkyl or unsubstituted alkyl or a substituted or unsubstituted aryl group; and
a high-spin Fe(III) cation complexed to the TACN moiety and at least one anionic pendent group substituent of the TACN moiety, or a high-spin Fe(III) cation complexed to the O-substituted TACN moiety and at least one anionic pendent group substituent of the O-substituted TACN moiety,
wherein:
when the macrocyclic complex is:

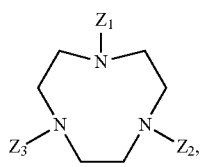

$Z_1$ and $Z_2$ are

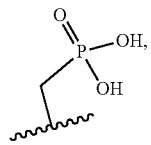 [SMILES: *CP(=O)(O)O]

and $Z_3$ is not

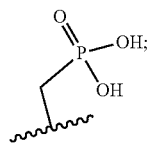

and
when the macrocyclic complex is:

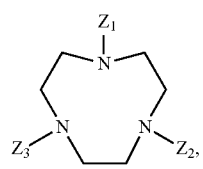

$Z_1$ and $Z_2$ are

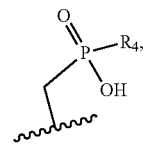

wherein $R^4$ is an unsubstituted aryl, and $Z_3$ is not

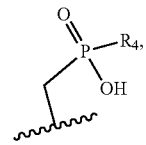

wherein $R^4$ is an unsubstituted aryl.

2. The macrocyclic complex of claim 1, wherein at least one or all of the one or more pendent groups is covalently bound to a nitrogen atom on the TACN moiety or an O-substituted TACN moiety.

3. The macrocyclic complex of claim 1, wherein the macrocyclic complex has at least one open coordination site.

4. The macrocyclic complex of claim 1, wherein the macrocyclic complex has at least one water complexed to the high-spin Fe(III) cation.

5. A macrocyclic complex comprising:
a 1,4,7-triazacyclononane (TACN) moiety having a structure:

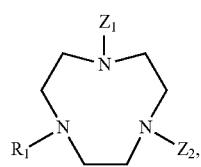
(II)

wherein $Z_1$ and $Z_2$ are anionic pendent groups independently chosen from:

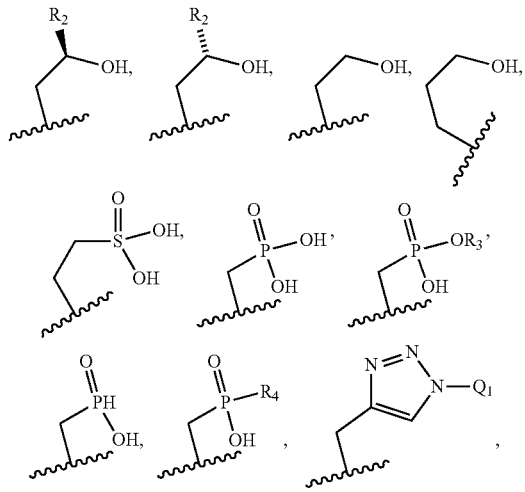

deprotonated analogs thereof, and combinations thereof,
$R_1$ is an anionic pendent groups independently chosen from:

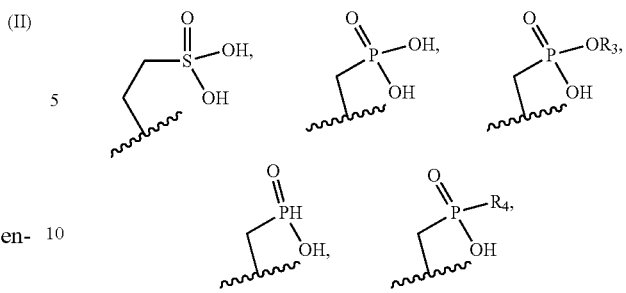

deprotonated analogs thereof, and combinations thereof,
wherein $R_2$ is a substituted or unsubstituted alkyl group, a substituted or unsubstituted aromatic group or a substituted ether; $R_3$ is a substituted or unsubstituted alkyl or a substituted or unsubstituted aryl group; $R_4$ is a substituted alkyl or unsubstituted alkyl or a substituted or unsubstituted aryl group; and $Q_1$ is aryl substituted with an anionic group, an alkyl group substituted with an anionic group or an aralkyl group substituted with an anionic group; and a high-spin Fe(III) cation complexed to the TACN moiety and at least one anionic pendent group substituent of the TACN moiety.

6. The macrocyclic complex of claim 5, wherein at least one or all of the one or more pendent groups is covalently bound to a nitrogen atom on the TACN moiety.

7. The macrocyclic complex of claim 5, wherein the macrocyclic complex has at least one open coordination site.

8. The macrocyclic complex of claim 5, wherein the macrocyclic complex has at least one water and/or at least one hydroxide complexed to the high-spin Fe(III) cation.

* * * * *